(12) United States Patent
Wong et al.

(10) Patent No.: US 9,011,915 B2
(45) Date of Patent: Apr. 21, 2015

(54) CONVENIENTLY IMPLANTABLE SUSTAINED RELEASE DRUG COMPOSITIONS

(75) Inventors: Vernon G. Wong, Menlo Park, CA (US); Louis L. Wood, Potomac, MD (US)

(73) Assignee: Ramscor, Inc., Menlo Park, CA (US)

( * ) Notice: Subject to any disclaimer, the term of this patent is extended or adjusted under 35 U.S.C. 154(b) by 269 days.

(21) Appl. No.: 13/006,801

(22) Filed: Jan. 14, 2011

(65) Prior Publication Data

US 2011/0111006 A1 May 12, 2011

Related U.S. Application Data

(60) Division of application No. 11/826,833, filed on Jul. 18, 2007, now abandoned, and a continuation-in-part of application No. 11/236,426, filed on Sep. 27, 2005, now Pat. No. 7,906,136.

(60) Provisional application No. 60/614,484, filed on Oct. 1, 2004, provisional application No. 60/709,665, filed on Aug. 19, 2005, provisional application No. 60/831,991, filed on Jul. 19, 2006.

(51) Int. Cl.
| | |
|---|---|
| *A61K 9/14* | (2006.01) |
| *A61K 31/355* | (2006.01) |
| *A61K 47/00* | (2006.01) |
| *A01N 43/16* | (2006.01) |
| *A01N 25/00* | (2006.01) |
| *A61K 9/00* | (2006.01) |
| *A61K 47/06* | (2006.01) |

(52) U.S. Cl.
CPC .............. *A61K 31/355* (2013.01); *A61K 9/0048* (2013.01); *A61K 47/06* (2013.01); *A61K 9/0024* (2013.01)

(58) Field of Classification Search
None
See application file for complete search history.

(56) References Cited

U.S. PATENT DOCUMENTS

| | | |
|---|---|---|
| 4,096,271 A | 6/1978 | de lis Masilungan |
| 4,304,765 A | 12/1981 | Shell et al. |
| 4,309,996 A | 1/1982 | Theeuwes |
| 4,568,547 A | 2/1986 | Herschler |
| 4,728,721 A | 3/1988 | Yamamoto et al. |
| 4,849,228 A | 7/1989 | Yamamoto et al. |
| 4,853,224 A | 8/1989 | Wong |
| 4,997,652 A | 3/1991 | Wong |
| 5,164,188 A | 11/1992 | Wong |
| 5,371,078 A | 12/1994 | Clark et al. |
| 5,443,505 A | 8/1995 | Wong et al. |
| 5,620,700 A | 4/1997 | Berggren et al. |
| 5,632,984 A | 5/1997 | Wong et al. |
| 5,653,992 A | 8/1997 | Bezwada et al. |
| 5,760,075 A | 6/1998 | St. Jernschantz et al. |
| 5,766,242 A | 6/1998 | Wong et al. |
| 5,770,589 A | 6/1998 | Billson et al. |
| 5,824,072 A | 10/1998 | Wong |
| 5,869,079 A | 2/1999 | Wong et al. |
| 5,886,030 A | 3/1999 | Maniar |
| 5,945,115 A | 8/1999 | Dunn et al. |
| 6,001,368 A * | 12/1999 | Jenks .............................. 62/646 |
| 6,130,200 A | 10/2000 | Brodbeck et al. |
| 6,174,540 B1 | 1/2001 | Williams et al. |
| 6,214,838 B1 | 4/2001 | Sohda et al. |
| 6,331,311 B1 | 12/2001 | Brodbeck et al. |
| 6,331,313 B1 | 12/2001 | Wong et al. |
| 6,369,116 B1 | 4/2002 | Wong et al. |
| 6,468,961 B1 | 10/2002 | Brodbeck et al. |
| 6,537,566 B1 | 3/2003 | Copeland et al. |
| 6,653,288 B1 | 11/2003 | Beuvry et al. |
| 6,699,493 B2 | 3/2004 | Wong |
| 6,726,918 B1 | 4/2004 | Wong et al. |
| 6,733,786 B1 | 5/2004 | Kim et al. |
| 6,827,931 B1 | 12/2004 | Donovan |
| 6,855,340 B2 | 2/2005 | Brewer |
| 7,074,426 B2 | 7/2006 | Kochinke |
| 7,449,491 B2 * | 11/2008 | Naguib et al. ................ 514/458 |
| 2002/0064547 A1 | 5/2002 | Chern et al. |
| 2003/0044467 A1 | 3/2003 | Brodbeck et al. |
| 2003/0104015 A1 | 6/2003 | Lambert et al. |
| 2003/0105156 A1 | 6/2003 | Palepu et al. |
| 2003/0211123 A1 | 11/2003 | Shukla et al. |
| 2003/0216303 A1 | 11/2003 | Ambuhl et al. |
| 2004/0092435 A1 | 5/2004 | Peyman |
| 2004/0106914 A1 | 6/2004 | Coppeta et al. |
| 2004/0151753 A1 | 8/2004 | Chen et al. |
| 2004/0151754 A1 | 8/2004 | Ashton |
| 2004/0258769 A1* | 12/2004 | Barker et al. .................. 424/638 |
| 2005/0101517 A1 | 5/2005 | De Nijs et al. |
| 2005/0118206 A1 | 6/2005 | Luke et al. |
| 2005/0143363 A1 | 6/2005 | De Juan et al. |
| 2005/0171193 A1 | 8/2005 | Chen et al. |
| 2005/0244469 A1 | 11/2005 | Whitcut et al. |
| 2006/0024360 A1 | 2/2006 | Chen |
| 2006/0141049 A1* | 6/2006 | Lyons et al. .................. 424/489 |
| 2008/0118547 A1* | 5/2008 | Huang et al. .................. 424/428 |

FOREIGN PATENT DOCUMENTS

| | | |
|---|---|---|
| CA | 2 436 361 A1 | 8/2002 |
| CN | 1240346 A | 1/2000 |

(Continued)

OTHER PUBLICATIONS

Monolithic."Merriam-Webster Online Dictionary". 2013. Merriam-Webster Online. May 21, 2013 www.merriam-webster.com/dictionary/monolithic>.*

(Continued)

*Primary Examiner* — Juliet Switzer
*Assistant Examiner* — Caralynne Helm
(74) *Attorney, Agent, or Firm* — Wiley Rein LLP

(57) ABSTRACT

This invention provides for biocompatible and biodegradable syringeable liquid, implantable solid, and injectable gel pharmaceutical formulations useful for the treatment of systemic and local disease states.

3 Claims, 19 Drawing Sheets

(56) References Cited

FOREIGN PATENT DOCUMENTS

| | | |
|---|---|---|
| CN | 1684663 A | 10/2005 |
| RU | 1769826 A1 | 10/1992 |
| WO | 99/65916 A1 | 12/1999 |
| WO | 00/02553 A1 | 1/2000 |
| WO | 00/02554 A1 | 1/2000 |
| WO | 00/59488 A2 | 10/2000 |
| WO | WO 0071163 A1 | 11/2000 |
| WO | 01/70256 A1 | 9/2001 |
| WO | WO 0170256 A1 | 9/2001 |
| wo | 03/061566 A2 | 7/2003 |
| WO | 03/099223 A1 | 12/2003 |
| WO | WO 2004011054 A2 | 2/2004 |
| WO | 2004/058272 A1 | 7/2004 |
| WO | WO 2004081196 A2 | 9/2004 |

OTHER PUBLICATIONS

Jain et al. European Journal of Pharmaceutics and Biopharmaceutics 2000 50:257-262.*
Coleman et al., 37(12) J. Pharm. Phamacol. 878-83 (1985).
Fishman et al., 27(7) Invest. Ophthalomol. Vis. Sci. 1103-06 (1986).
Migally, 2(4) Arch. Androl. 365-69 (1979).
Wang et al., 90 J. Cont. Release 345-54 (2003).
Supplementary European Search Report dated Aug. 13, 2009.
Office Action issued by the Canadian Intellectual Property Office, on Jun. 6, 2012, in related Canadian patent application No. 2,582,096, filed Sep. 27, 2005.
Benghuzzi, H. A. et al, "The effect of sustained delivery of danazol and antioxidants on lipoprotein profiles of adult female mice," Biomedical Sciences Instrumentation, 1995, vol. 31, pp. 171-176.

* cited by examiner

CONVENIENTLY IMPLANTABLE SUSTAINED RELEASE DRUG COMPOSITIONS

RELATED APPLICATIONS

This application is related to and claims the benefit under 35 U.S.C. §119(e) of U.S. Patent Application Ser. No. 60/831,991, filed Jul. 19, 2006, and is a continuation-in-part and claims the benefit under 35 U.S.C. §120 of U.S. patent application Ser. No. 11/236,426, filed Sep. 27, 2005, which is related to and claims the benefit under 35 U.S.C. §119(e) of U.S. Patent Application Ser. No. 60/709,665, filed Aug. 19, 2005, and Ser. No. 60/614,484, filed Oct. 1, 2004, each entitled Conveniently Implantable Sustained Release Drug Compositions, by Vernon G. Wong and Louis L. Wood. Each of the foregoing applications is incorporated in its entirety herein.

FIELD OF THE INVENTION

This invention provides for biocompatible and biodegradable syringeable liquid, implantable solid, and injectable gel pharmaceutical formulations useful for the treatment of systemic and local diseases.

BACKGROUND OF THE INVENTION

Present modes of drug delivery such as topical application, oral delivery, and intramuscular, intravenous and subcutaneous injection may result in high and low blood concentrations and/or shortened half-life in the blood. In some cases, achieving therapeutic efficacy with these standard administrations requires large doses of medications that may result in toxic side effects. The technologies relating to controlled drug release have been attempted in an effort to circumvent some of the pitfalls of conventional therapy. Their aims are to deliver medications on a continuous and sustained manner. Additionally, local control drug release applications are site or organ specific.

In response to these issues, reservoir delivery systems have been explored. Non-biodegradable drug delivery systems include, for example, Vitrasert® (Bausch & Lomb Inc.), a surgical implant that delivers ganciclovir intraocularly; Duros® (Alza Corp.), surgically implanted osmotic pump that delivers leuprolide actetate to treat advanced prostate cancer; and Implanon™ (Organon USA Inc.), a type of subdermal contraceptive implant.

Biodegradable implants include, for example, Lupron Depot® (leuprolide acetate, TAP Pharm. Prods., Inc.), a sustained-release microsphere-suspension injection of luteinizing hormone-releasing hormone (LH-RH) analog for the treatment of prostate cancer; and the Posurdex® dexamethasone anterior segment drug delivery system (Allergan, Inc.) (commercial licensure pending FDA approval).

Additionally, polyethylene glycol conjugations (pegylation) to reduce the frequency of administration are now in use. One example is Macugen® (pegaptanib sodium injection, (OSI) Eyetech, Inc./Pfizer Inc.), a pegylated anti-VEGF aptamer, for use in treating wet macular degeneration.

There remains a need for a more economical, practical, and efficient way of producing and manufacturing drug delivery systems that could be used locally or systemically, in solid, semi-solid, or liquid formulations.

SUMMARY OF THE INVENTION

An object of the present invention provides for economical, practical, and efficient drug delivery systems. According to the present invention, this drug delivery system is produced easily, delivered easily to the site of indication, and is both biocompatible and biodegradable. More specifically, the formulations of the present invention provide for novel therapies that are easily manipulated and injected or implanted by qualified medical practitioners. The formulations deliver therapeutic and non-toxic levels of active agents over the desired extended time frame, primarily at the site of implantation. The formulations are both biocompatible and biodegradable, and disappear harmlessly after delivering active agent to the desired site.

One embodiment of the present invention provides for a pharmaceutical formulation for implantation into a patient for the sustained release of an active agent comprising a biocompatible, biodegradable excipient and an active agent or pharmaceutically acceptable salt thereof. In an aspect of the invention, the formulation is capable of being implanted by injection.

Another embodiment of the invention provides for a pharmaceutical formulation for implantation into a patient for the sustained release of an active agent comprising a biocompatible, biodegradable excipient and an active agent or pharmaceutically acceptable salt thereof, wherein said formulation exhibits an in vitro dissolution profile wherein about 2% to about 100% of the active agent is released over a period ranging from about 1 day to at least 365 days.

Yet another embodiment provides for a pharmaceutical formulation for implantation into a patient for the sustained release of an active agent comprising a biocompatible, biodegradable excipient and an active agent or pharmaceutically acceptable salt thereof, wherein about 2% to about 60% of the active agent is released over a period ranging from about 1 day to about 105 days. Alternatively, about 2% to about 100% of the active agent may be released over a period of about 25 days. Or about 2% to about 85% of the active agent may be released over a period of about 30 days to about 60 days. In another embodiment, about 2% to about 60% of the active agent is released over a period ranging from about 80 days to about 100 days.

In another aspect of the invention, the formulation comprises an active agent at a concentration from about 5% to about 50% of the implant and includes a biodegradable, biocompatible excipient at a concentration of at least about 5% percent of the implant.

In another embodiment, the biocompatible, biodegradable excipient may be chosen from tocopherol isomers and/or their esters, tocotrienols and/or their esters, benzyl benzoate, esters of benzoic acid with straight, branched, or cyclic chain aliphatic alcohols having one to twenty carbon atoms wherein one of the hydrogen atoms on the aliphatic chain is replaced with a hydroxyl group, tocopherol isomer acetates, succinates and nicotinates, tocotrienol isomer acetates, succinates and nicotinates, the mono, di, and tri esters of O-acetylcitric acid or O-propionylcitric acid or O-butyrylcitric acid with $C_1$ to $C_{10}$ straight and branched chain aliphatic alcohols, the mono, di, and tri esters of citric acid with $C_1$ to $C_{10}$ straight and branched chain aliphatic alcohols, dibenzoate esters of poly (oxyethylene)diols having low water solubility, poly(oxypropylene)diols having low water solubility, dimethyl sulfone, liquid and semisolid polycarbonate oligomers, or mixtures of two or more these. In an aspect of the invention, the liquid to semisolid polycarbonate oligomers includes those prepared by the polymerization of trimethylene carbonate[poly(1,3-propanediol carbonate)], the ester exchange polymerization of diethylene carbonate with aliphatic diols or polyoxyalkane diols[poly(di-1,2-propylene glycol carbonate), and poly(tri-1,2-propylene glycol carbonate)].

An aspect of the invention provides for a controlled and sustained drug delivery system for the posterior segment of the eye, comprised of a biodegradable and biocompatible liquid matrix for direct injection. A particular aspect of the invention provides for compositions comprising either dexamethasone or triamcinolone acetonide and benzyl benzoate. In another aspect of this embodiment, dexamethasone or triamcinolone acetonide is released into the vitreous of the eye in an amount ranging from about 20 µg/ml to less than about 1.0 µg/ml over a period of about sixty days to about ninety days.

Another embodiment of the present invention provides for a biocompatible, biodegradable, syringeable liquid, implantable solid, and injectable gel sustained release formulations of therapeutic agents for brain tumors that may be inserted directly into brain tumors. These formulations comprise novel biocompatible and biodegradable syringeable liquid, implantable cohesive solids, and injectable gel formulations conveniently placed inside brain tumors for the sustained release of beneficial agents are obtained by admixing one or more of the excipients of the present invention with one or more of established and new agents for the treatment of brain tumors, including anti-neovascularization steroids.

The active agent envisioned in an embodiment of the present invention is one selected from one or more of the group consisting of analgesics, anesthetics, narcotics, angiostatic steroids, anti-inflammatory steroids, angiogenesis inhibitors, nonsteroidal anti-inflammatories, anti-infective agents, antibiotics, antifungals, antimalarials, antitublerculosis agents, antivirals, alpha androgenergic agonists, beta adrenergic blocking agents, carbonic anhydrase inhibitors, mast cell stabilizers, miotics, prostaglandins, antihistamines, antimicrotubule agents, antineoplastic agents, antipoptotics, aldose reductase inhibitors, antihypertensives, antioxidants, growth hormone agonists and antagonists, vitrectomy agents, adenosine receptor antagonists, adenosine deaminase inhibitors, glycosylation antagonists, anti-aging peptides, topoisemerase inhibitors, anti-metabolites, alkylating agents, antiandrigens, anti-oestogens, oncogene activation inhibitors, telomerase inhibitors, antibodies or portions thereof, antisense oligonucleotides, fusion proteins, luteinizing hormone releasing hormones agonists, gonadotropin releasing hormone agonists, tyrosine kinase inhibitors, epidermal growth factor inhibitors, ribonucleotide reductase inhibitors, cytotoxins, IL2 therapeutics, neurotensin antagonists, peripheral sigma ligands, endothelin ETA/receptor antagonists, antihyperglycemics, anti-glaucoma agents, anti-chromatin modifying enzymes, insulins, glucagon-like-peptides, obesity management agents, anemia therapeutics, emesis therapeutics, neutropaenia therapeutics, tumor-induced hypercalcaemia therapeutics, blood anticoagulants, immunosuppressive agents, tissue repair agents, psychotherapeutic agents, botulinum toxins, essential fatty acids, and nucleic acids such as siRNA and RNAi.

In another embodiment of the invention, the active agent or excipient may be an omega-3 fatty acid or an ester thereof. Another embodiment of the present invention provides for a formulation comprising a nonpolymeric, biodegradable, bioabsorbable excipient and the active agent is one or more antioxidants, either alone or included with one or more steroids and/or quinolone anti-infectives. Still another embodiment provides for the transdermal delivery of active agents, for example, insulin.

DETAILED DESCRIPTION OF THE INVENTION

Figure 1:
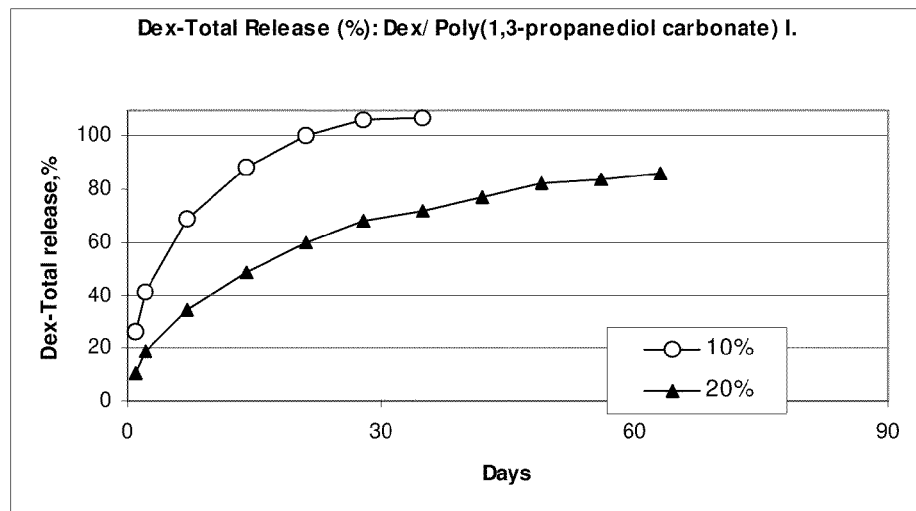
FIG. 1 presents dissolution profiles of dexamethasone (Dex) from two formulations of Dex/poly(1,3-propanediol carbonate)I.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. Thus, for example, the reference to an excipient is a reference to one or more such excipients, including equivalents thereof known to those skilled in the art. Other than in the operating examples, or where otherwise indicated, all numbers expressing quantities of ingredients or reaction conditions used herein should be understood as modified in all instances by the term "about." The term "about" when used in connection with percentages may mean±1%.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

Unless defined otherwise, all technical and scientific terms used herein have the same meaning as those commonly understood to one of ordinary skill in the art to which this invention pertains.

The present invention relates to novel biocompatible, biodegradable sustained release formulations. In various aspects of the invention, these formulations are syringeable liquids, mechanically cohesive solids, injectable gels, or emulsified micells (oil in water or water in oil). A desirable feature of these liquid, solid, and gel formulations is that they maintain a single bolus or pellet shape at the site of their placement. That is, they do not break up as a multitude of smaller droplets or particles that migrate away from their intended point of placement and/or by virtue of a resultant increase in surface area greatly alter the intended release rate of their drug content.

The formulations of the present invention provide for novel therapies that are easily manipulated and injected or implanted by qualified medical practitioners. The formulations deliver therapeutic and non-toxic levels of active agents over the desired extended time frame, primarily at the site of implantation. The formulations are both biocompatible and biodegradable, and disappear harmlessly after delivering active agent to the desired site.

The present invention relates generally, but not totally, to the use of formulations that are of limited solubility, biocompatible, and biodegradable (LSBB), which may also be syringeable, for controlled and sustained release of an active agent or a combination of active agents. Solid, gel or injectable, controlled-sustained release systems can be fabricated by combining LSBB and an active agent. Systems can combine more than one biodegradable component as well as more than one active agent. Solid forms for implantation can be produced by tableting, injection molding or by extrusion. Gels can be produced by vortex or mechanical mixing. Injectable formulations can be made by pre-mixing in a syringe or mixing of the LSBB and the active agent before or at the time of administration. Formulations may serve as coating for stents or other implants by, for example, dipping the stent in a liquid form of the formulation and then drying it.

In an aspect of the present invention, novel biocompatible and biodegradable syringeable liquid, implantable cohesive solids, and injectable gel formulations conveniently placed on or within the human or animal body for the sustained release of active agents, are obtained by admixing one or more excipients, such as, for example: benzyl benzoate, esters of benzoic acid with straight, branched, or cyclic chain aliphatic alcohols having one to twenty carbon atoms wherein one of the hydrogen atoms on the aliphatic chain is replaced with a hydroxyl group (e.g., such alcohols as methanol, ethanol, n-propanol, i-propanol, n-butanol, i-butanol, s-butanol, t-butanol, n-pentanol, i-pentanol, neo-pentanol, n-hexanol, cyclohexanol, n-heptanol, n-octonol, n-nonanol, n-decanol, and the like), tocopherol isomer acetates, succinates and nicotinates, tocotrienol isomer acetates, succinates and nicotinates, the mono, di, and tri esters of O-acetylcitric acid or O-propionylcitric acid or O-butyrylcitric acid with $C_1$ to $C_{10}$ straight and branched chain aliphatic alcohols, the mono, di, and tri esters of citric acid with $C_1$ to $C_{10}$ straight and branched chain aliphatic alcohols, omega-3 fatty acids and their esters of $C_1$ to $C_8$ straight and branched chain aliphatic alcohols, dibenzoate esters of poly(oxyethylene)diols having low water solubility, poly(oxypropylene)diols having low water solubility, dimethyl sulfone, liquid and semisolid polycarbonate oligomers, with a large number of established and new active agents. In an aspect of the invention, the liquid to semisolid polycarbonate oligomers include those prepared by the polymerization of trimethylene carbonate[poly(1,3-propanediol carbonate)], the ester exchange polymerization of diethylene carbonate with aliphatic diols or polyoxyalkane diols[poly(di-1,2-propylene glycol carbonate), and poly(tri-1,2-propylene glycol carbonate)].

In another aspect of the invention, the solid form generally contains about 1% to about 60% of an LSBB, the gel form generally contains about 20% to about 80% of an LSBB, and an injectable form (which may be a gel or liquid form) generally contains about 30% to about 99.9% of an LSBB.

Liquid and solid LSBB formulations can be implanted, for example, surgically, by trocar, or by needle introduction. The formulations can be placed into body cavities such as joints by methods well-known in the art (typically using the procedures outlined by Cardone & Tallia, Am. Family Physician, 66(2), 283-92 (2002); 66(11), 2097-100 (2002); 67(10), 2147-52 (2003); 68(7), 1356-62 (2003); 67(4), 745-50 (2003)); intraocular (chambers such as the anterior chamber and posterior segment of the eye); intratumoral injection into the prostate tumor (typically using a procedure similar to that described by Jackson et al., 60(5) Cancer Res., 4146-51 (2000)); intratumoral injection into inoperable tumors (such as gliomas) in the brain (typically using a procedure similar to that described by Emerich et al., 17(7) Pharm Res, 767-75 (2000)); injection or insertion into an intravertebral disc or disc space; injection into peritoneal cavity, or intranasal, intrathecal, subcutaneous or intramuscular injection, injection into the epidural, subdural and/or subarachnoid space; or the formulation may be injected or inserted directly into the cerebral spinal fluid through the spinal canal or into the CNS ventricular system.

Additionally, for localized active agent delivery, the system of the present invention may be surgically implanted at or near the site of action. This may be useful when it is used, for example, in treating ocular conditions, primary tumors, rheumatic and arthritic conditions, and chronic pain.

It is contemplated that these LSBB/active agent compositions can be applied to the following, but not limited to, systems of the human or animal body: muscular, skeletal, nervous, autonomic nervous, vascular, lymphatic, digestive, respiratory, urinary, female reproductive, male reproductive, endocrine or intraparenchymal, to provide a wide variety of sustained therapies.

Specific areas of the human or animal body to be targeted for injection or implantation or topical applications of these LSBB/active agents compositions include, but are not limited to: heart, brain, spinal nerves, vertebral column, skull, neck, head, eye, ear organs of hearing and balance, nose, throat, skin, viscera, hair, shoulder, elbow, hand, wrist, hip, knee, ankle, foot, teeth, gums, liver, kidney, pancreas, prostate, testicles, ovaries, thymus, adrenal glands, pharynx, larynx, bones, bone marrow, stomach, bowel, upper and lower intestines, bladder, lungs, mammaries. Surgical implantation into the eye, for example, is known in the art as described in U.S. Pat. No. 6,699,493; No. 6,726,918; No. 6,331,313; No. 5,824,072; No. 5,766,242; No. 5,443,505; No. 5,164,188; No. 4,997,652; and No. 4,853,224.

Solid LSBB formulations, for example, may be implanted directly into parenchymal tissues such as the brain, spinal cord, or any part of the CNS system, into the kidney, liver, spleen, pancreas, lymph nodes as well as tumors. Gel LSBB systems may be applied to surface tissues such as the skin, or as coating on surfaces of parenchymal organs to be absorbed, or be applied directly on the cornea, conjunctiva and on the sclera for delivery of active agent onto the surface of and intraocularly to the eye. Injectable LSBB formulations are less invasive and can be delivered, for example, through a 30 gauge needle into the eye, or through larger needles into cavities such as joints.

The system according to the present invention has particular applicability in providing a controlled and sustained release of active agents effective in obtaining a desired local or systemic physiological or pharmacological effect relating at least to the following areas: treatment of cancerous primary tumors, chronic pain, arthritis, rheumatic conditions, hormonal deficiencies such as diabetes and dwarfism, modification of the immune response such as in the prevention and treatment of transplant rejection and in cancer therapy. The system is also suitable for use in treating HIV and HIV related opportunistic infections such as CMV, toxoplasmosis, *Pneumocystis carinii*, and *Mycobacterium avium*-intercellulare. The system may be used to delivery an active agent effective in treating fungal infection of the mouth. If such a use is desired, the system may be designed to have a shape suitable for implanting into a tooth.

LSBB formulations are also useful for treating ocular conditions such as glaucoma, PVR, diabetic retinopathy, uveitis, retinal edema, vein occlusion, macular degeneration, Irvine-Gass Syndrome and CMV retinitis, corneal diseases such as keratitis, and corneal transplantation rejection. The formulations may also be prepared as control-release eye drops for dry-eye or for controlling the immune response. Regarding control of immune responses, the formulations may contain one or more of cyclosporine, sirolimus, or tacrolimus. Other intraocular uses include glaucoma treatments (e.g., formulations including timolol), antibiotic delivery, antibody delivery, and antiproliferatives delivery (e.g., paclitaxel).

Other uses of the formulations include, for example, mediating homograft rejection with formulations comprising sirolimus or cyclosporine. Local cancer therapy may be delivered to, for example, the kidney or liver, using in formulations comprising, for example, adriamycin or small epidermal growth factors. Prostate cancer may be treated with formulations including fenasteride. Cardiac stents implants, central nervous system implants (e.g., spinal implants), orthopedic implants, etc., may be coated with formulations including growth or differentiation factors, anti-inflammatory agents, or antibiotics.

Additionally, the pharmaceutical formulations herein provide for methods for the management of skin wrinkles, or bladder, prostatic and pelvic floor disorders by implanting, by injection, a pharmaceutical formulation comprising a biodegradable, biocompatible excipient and botulinum toxins into a strategic position in the skin or bladder, prostate or pelvic floor region to provide controlled and sustained release of a therapeutically effective but non-toxic level of the botulinum toxins within the effected areas. The pharmaceutical formulations herein also provide methods for the management of uterine fibroids by implanting, by injection, a pharmaceutical formulation comprising a biodegradable, biocompatible excipient and suitable therapeutic agent, such as pirfenidone, human interferin-alpha, GnRH antagonists, Redoxifene and estrogen-receptor modulators, into strategic positions inside the fibroids to provide controlled and sustained release of therapeutically effective, but non-toxic levels, of the therapeutic agents within the fibroids.

The technology of the present application is useful in overcoming the difficulties reported in some cases of achieving therapeutic efficacy, as experienced in current administrations requiring large doses of medications that may result in toxic side effects. An important example of this problem is the current clinical practice of intravitreal injections of microcrystalline triamcinolone acetonide (TA) for the treatment of intraocular neovascular, oedematous, or inflammatory diseases. See Jonas et al., 24(5) Prog Retin Eye Res. 587-611 (2005), and references therein. The therapy requires the presence of a solution of the proper TA concentration in the vitreous chamber for periods of six months to a year and possibly longer. The therapeutic vitreal concentrations of TA seem to be at 1.0 µg/ml or below (Matsuda et al., 46 Invest Ophthalmol Vis Sci. 1062-1068 (2005)) whereas harmful complications (glaucoma, cataracts, cytotoxicity) can arise when TA concentrations continuously exceed 10 µg/ml over an extended period of time. See Gillies et al., 122(3) Arch Ophthalmol. 336-340 (2004); Jonas et al., 15(4) Eur J Ophthalmol. 462-4 (2005); Yeung et al, 44 Invest Ophthalmol Vis Sci. 5293-5300 (2003). The desire to limit TA administration to one or two injections per year (because of patient discomfort coupled with the possibility of endophthalmitis (see Bucher et al., 123(5) Arch Ophthalmol. 649-53 (2005)), conflicts with the ability of supplying enough TA crystals without excursions into toxic concentrations. The novel compositions of this invention solve this problem by encompassing the desired amounts of TA in an injectable, biocompatible, bioerodable medium that continuously regulates the release of safe, therapeutic levels of intravitreal TA for periods of six months or more.

Further regarding ocular conditions, metabolic and inflammation conditions in the posterior segment of the eye have been extremely difficult to treat. Such conditions as proliferative vitreoretinopathy (PVR), uveitis, cystoid macular edema (CME), diabetes, and macular degeneration are major causes of blindness. Conventional methods of drug delivery, including topical, periocular, subconjunctival or systemic administration, have had limited success due in large part to poor drug penetration (due to the blood-eye barrier) and toxic side effects. One efficient way of delivering a drug to the posterior segment is to place it directly into the vitreous cavity. Intravitreal drug injections have shown promising results in animals and in humans, but repeated and frequent injections have had to be performed to maintain therapeutic levels.

For example, direct injection of corticosteroids, particularly triamcinolone acetonide, has been effective particularly in selected wet macular degeration and in diabetic retinal edemas. Because of the drugs' short half-life in the eye, frequent injections are required. Moreover, because the drug is being given in a bolus, uncontrolled high and then low drug concentration levels are encountered. As a consequence, adverse reactions such as infection, glaucoma, cataract formation, retinal detachment and intraocular bleeding have been common adverse occurrences. Vitrasert® (Bausch & Lomb) is a six- to eight-month reservoir system to treat CMV retinitis with the antiviral gancyclovir. This is a non-biodegradable system and must be both inserted and removed surgically. Similarly, Posurdex® (Allergan, Inc.) is a one-month biodegradable delivery system that must be implanted surgically into the eye, and contains dexamethasone and poly (lactic-co-glycolic acid) (PLGA) for the treatment of posterior segment pathologies.

Hence, one embodiment of the present invention provides for an intraocular controlled and sustained drug delivery system for the posterior segment of the eye. It is comprised of a biodegradable and biocompatible liquid matrix containing a microdispersed drug or mixture of drugs, and can be injected directly into the posterior segment with a relatively small needle. The duration of drug delivery can be as short as a few days to many months and up to one year or longer, and the matrix gradually and safely dissipates over time so that there is no need to remove it. An example embodiment comprises dexamethasone and benzyl benzoate. In this system, intravitreal levels of dexamethasone with a 25% formulation in 50 µl delivers a mean vitreous level of approximately 8.0 µg/ml over a three-month period. In comparison, a 25 µl injection delivers a mean vitreous level of approximately 4.0 µg/ml over a sixty day period. This composition is biocompatible, biodegradable, non-toxic, easy to manufacture, easy to deliver, and flexible in terms of therapeutic dose and duration of delivery.

Another aspect of the invention provides for a formulation for limiting tissue rejection following corneal transplant. Corneal transplant, also known as a corneal graft, or as a penetrating keratoplasty, involves the removal of the central portion (called a button) of the diseased cornea and replacing it with a matched donor button of cornea. Corneal grafts are performed on patients with damaged or scarred corneas that prevent acceptable vision. This may be due to corneal scarring from disease or trauma. Formulations of the present invention useful in corneal transplant contexts may include rapamycin, cyclosporin, or a combination of these active agents.

Further regarding cyclosporin and rapamycin, these active agents may be used in the anterior segment and/or the posterior segment of the eye. These are antiimmune drugs that have antiinflammatory properties, antirejections properties, antifibrosis activities, and antineogenesis properties. As provided for herein, formulations of these agents either alone or in combination may be prepared for use in the used in the anterior segment for corneal rejection (organ rejection) or any inflammatory conditions. Formulations may also be prepared for use in the posterior segment or back of the eye for indications such as macular degeneration, antineogenesis which occurs in macular degeneration, or for cellular transplants or stem cell transplants for repair or in maintaining the health of the retina, choroid etc.

A wide variety of other disease states are known by those of ordinary skill in the art, such as those described in Goodman & Gilman, THE PHARMACOLOGICAL BASIS OF THERAPEUTICS (McGraw Hill, 2001), and REMINGTON'S PHARMACEUTICAL SCIENCES (Lippincott Williams & Wilkins; 20th ed., 2000). Those to which the present invention may be applied may be determined by those with ordinary skill in the art without undue experimentation.

Suitable classes of active agents for use in the system of the present invention include, but are not limited to the following:

Peptides and proteins such as cyclosporin, insulins, glucagon-like-peptides, growth hormones, insulin related growth factor, botulinum toxins (Botox, Allergan), antibodies, and heat shock proteins;

Anesthetics and pain killing agents such as lidocaine and related compounds, and benzodiazepam and related compounds;

Anti-cancer agents such as 5-fluorouracil, methotrexate and related compounds;

Anti-inflammatory agents such as 6-mannose phosphate;

Anti-fungal agents such as fluconazole and related compounds;

Antiviral agents such as trisodium phosphomonoformate, trifluorothymidine, acyclovir, cidofovir, ganciclovir, ddI, and AZT;

Cell transport/mobility impending agents such as colchicines, vincristine, cytochalasin B, and related compounds;

Anti-glaucoma drugs such as beta-blockers: timolol, betaxolol, and atenolol;

Immunological response modifiers such as muramyl dipeptide and related compounds;

Steroidal compounds such as dexamethasone, prednisolone, triamcinolone and related compounds; and Carbonic anhydrase inhibitors such as acetazolamide, brinzolamide, dorzolamide, and timolol maleate.

In addition to the above agents, other active agents which are suitable for administration, especially to the eye and its surrounding tissues, to produce a local or a systemic physiologic or pharmacologic effect can be used in the system of the present invention. Examples of such agents include antibiotics such as tetracycline, chloramphenicol, ciprofloxacin, ampicillin and the like.

Any pharmaceutically acceptable form of the active agents of the present invention may be employed in the practice of the present invention, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate, and the like.

The active agents may also be used in combination with pharmaceutically acceptable carriers in additional ingredients such as antioxidants, stabilizing agents, and diffusion enhancers. For example, where water uptake by the active agent is undesired, the active agent can be formulated in a hydrophobic carrier, such as a wax or an oil, that would allow sufficient diffusion of the active agent from the system. Such carriers are well known in the art.

In another aspect of the invention, a low solubility active agent may be combined with a biodegradable, biocompatible excipient of higher solubility to result in an LSBB formulation. For example, dimethyl sulfone may be used as a binder in an LSBB formulation of a limited solubility active agent. Hence, the use of a soluble excipient in an LSBB formulation is within the scope of the present invention.

In one embodiment, the active agents, e.g., proteins, may be formulated in a glassy matrix of sugar which tends to protect the active agent from hydrolytic degradation and extend their shelf life and eliminate the need for cold storage. See, for example, Franks, *Long-Term Stabilization of Biologicals,* 12 Bio/Technology 253-56 (1994), the contents of which are hereby incorporated by reference.

Proteins may be formulated in a glass matrix by removing water from a homogeneous solution thereof. The water can be removed either by evaporation or by rapidly cold quenching the solution. The process is commonly referred to as vitrification. As water is removed from the solution, it becomes increasingly viscous until a "solidified" liquid containing the proteins is obtained. The "solidified" liquid is generically called glass.

Glasses have a number of unique physical and chemical properties which make them ideal for active agent formulation. Among them, the most important is that the solidified liquid retains the molecular disorder of the original solution. This disorder contributes to the glasses' long-term stability by preventing crystallization and chemical reactions of the proteins encased therein.

Sugars can also play an important part in stabilizing protein formulations. In solution, they are known to shift the denaturation equilibrium of proteins toward the native state. Most sugars, particularly low molecular weight carbohydrates, are also known to vitrify easily and to provide a glassy matrix that retards inactivating reactions of the proteins.

For illustrative purposes, the glassy sugar matrix for use in the system according to the present invention can be made by compressing a lyophilized mix of a protein with sugar and a buffer, and optionally, binders.

Examples of proteins and proteinaceous compounds which may be formulated and employed in the delivery system according to the present invention include those proteins which have biological activity or which may be used to treat a disease or other pathological condition. They include, but are not limited to antibodies, growth hormone, Factor VIII, Factor IX and other coagulation factors, chymotrypsin, trysinogen, alpha-interferon, beta-galactosidase, lactate dehydrogenase, growth factors, clotting factors, enzymes, immune response stimulators, cytokines, lymphokines, interferons, immunoglobulins, retroviruses, interleukins, peptides, somatostatin, somatotropin analogues, somatomedin-C, Gonadotropic releasing hormone, follicle stimulating hormone, luteinizing hormone, LHRH, LHRH analogues such as leuprolide, nafarelin and geserelin, LHRH agonists and antagonists, growth hormone releasing factor, callcitonin, colchicines, gonadotropins such as chorionic gonadotropin, oxytocin, octreotide, somatotropin plus and amino acid, vasopressin, adrenocorticotrophic hormone, epidermal growth factor, prolactin, somatotropin plus a protein, cosyntropin, lypressin, polypeptides such as thyrotropin releasing hormone, thyroid stimulation hormone, secretin, pancreozymin, enkephalin, glucagons, and endocrine agents secreted internally and distributed by way of the bloodstream.

Other agents, such as $\alpha_1$ antitrypsin, insulin, glucagon-like-peptides, and other peptide hormones, botulinum toxins (Botox®, Allergan, Inc.), adrenal cortical stimulating hormone, thyroid stimulating hormone, and other pituitary hormones, interferons such as $\alpha$, $\beta$, and $\delta$ interferon, erythropoietin, growth factors such as GCSFm GM-CSF, insulin-like growth factor 1, tissue plasminogen activator, CF4, dDAVP, tumor necrosis factor receptor, pancreatic enzymes, lactase, interleukin-1 receptor antagonist, interleukin-2, tumor suppresser proteins, cytotoxic proteins, viruses, viral proteins, recombinant antibodies, portions of antibodies, and antibody fragments and the like may be used. Analogs, derivatives, antagonists, agonists, and pharmaceutically acceptable salts of the above may also be used.

Other active agents encompassed in the present invention include prodrugs. Because prodrugs are known to enhance numerous desirable qualities of pharmaceuticals (e.g., solubility, bioavailability, manufacturing, etc.) the pharmaceutical dosage forms of the present invention may contain compounds in prodrug form. Thus, the present invention is intended to cover prodrugs of the presently claimed active agents, methods of delivering the same, and compositions containing the same.

Analogs, such as a compound that comprises a chemically modified form of a specific compound or class thereof, and that maintains the pharmaceutical and/or pharmacological activities characteristic of said compound or class, are also encompassed in the present invention. Similarly, derivatives such as a chemically modified compound wherein the modification is considered routine by the ordinary skilled chemist, such as an ester or an amide of an acid, protecting groups, such as a benzyl group for an alcohol or thiol, and tert-butoxycarbonyl group for an amine, are also encompassed by the present invention.

The active agents are useful for the treatment or prevention of a variety of conditions including, but not limited to hemophilia and other blood disorders, growth disorders, diabetes, obesity, leukemia, hepatitis, renal failure, HIV infection, hereditary diseases such as cerebrosidase deficiency and adenoine deaminase deficiency, hypertension, septic shock, autoimmune disease such as multiple sclerosis, Graves disease, systemic lupus erythematosus and rheumatoid arthritis, shock and wasting disorders, cystic fibrosis, lactose intolerance, Crohn's disease, inflammatory bowel disease, gastrointestinal and other cancers, cancerous or benign tumors, and management of bladder, prostatic, and pelvic floor disorders, and uterine fibroid (submucosal, subserosal, intramural, parasitic myomas, and seedling myomas) management (using for example but not limited to pirfenidone, human interferin-alpha, GnRH antagonists, Redoxifene, estrogen-receptor modulators). Additionally, the formulations of the present invention may be used to treat intracranial aneurysms by, for example, introducing fibrogen or plasmin.

It is further contemplated that topical formulations of these LSBBs with active agents can be applied for the transdermal administration of contraceptives, insulin or GLP-1, transdermal application for alopecia treatment or delivery of aspirin or other small molecules, smoking cessation agents, anti-obesity agents, antivirals (herpes therapies), agents for psoriasis therapies, agents for alopecia therapies, agents for acne therapies, agents for erectile disfunction and antiparasitic agents, to name a few.

The protein compounds useful in the formulations of the present invention can be used in the form of a salt, preferably a pharmaceutically acceptable salt. Useful salts are known to those skilled in the art and include salts with inorganic acids, organic acids, inorganic bases, or organic bases.

Sugars useful for preparing the glassy matrix discussed previously include, but are not limited to, glucose, sucrose, trehalose, lactose, maltose, raffinose, stachyose, maltodextrins, cyclodextrins, sugar polymers such as dextrans and their derivatives, ficoll, and starch.

Buffers useful for formulating the glassy matrix include, but not limited to MES, HEPES, citrate, lactate, acetate, and amino acid buffers known in the art.

The LSBB system comprising the glassy sugar matrix may be constructed of a bioerodible polymer with low water permeability. Such polymers include poly(glycolic acid), poly(lactic acid), copolymers of lactic/glycolic acid, polyorthoesters, polyanhydrides, polyphosphazones, polycaprolactone. These polymers may be advantageous because of their slow erosion properties and low water uptake; thus, they should not undergo undue changes during the course of the active agent delivery.

Naturally occurring or synthetic materials that are biologically compatible with body fluids suitable for use in the present invention generally include polymers such as polyethylene, polypropylene, polyethylene terephthalate, crosslinked polyester, polcarbonate, polysulfone, poly(2-pentene), poly(methylmethacrylate), poly(1,4-phenylene), polytetrafluoroethylene, and poly-ethylene-vinylacetate (EVA).

In an aspect of the present invention, the excipient is also biodegradable or bioerodible. As used herein, the terms "bioerodible" and "biodegradable" are equivalent and are used interchangeably. Biodegradable excipients are those which degrade in vivo, and wherein erosion of the excipient over time is required to achieve the agent release kinetics according to the invention. Suitable biodegradable excipients may include but are not limited to, for example, poly(glycolic acid), poly(lactic acid), copolymers of lactic/glycolic acid, polyorthoesters, polyanhydrides, polyphosphazones, polycarbonates, and polycaprolactone. The use of polylactic polyglycolic acid is described in, for example, U.S. Pat. No. 6,699,493. See also U.S. Pat. No. 5,869,079.

In another aspect of the invention, the excipient is biocompatible, meaning that it does not have undue toxicity or cause either physiologically or pharmacologically harmful effects. In another aspect of the invention, the excipient is biodegradable.

Examples of excipients that may be useful as biocompatible, biodegradable and/or bioerodible excipients in the present invention, as determined by one of ordinary skill in the art in light of this specification, without undue experimentation, include, but are not limited to d-α-tocopherol; d,l-α-tocopherol; d-β-tocopherol; d,l-β-tocopherol; d-η-tocopherol; and d,l-η-tocopherol (including acetate, hemisuccinate, nicotinate, and succinate-PEG ester forms of each of the foregoing, including a succinic-PEG ester such as tocophersolan); tocotrienol isomers, and their esters; benzyl benzoate, esters of benzoic acid with straight, branched, or cyclic chain aliphatic alcohols having one to twenty carbon atoms wherein one of the hydrogen atoms on the aliphatic chain is replaced with a hydroxyl group (e.g., such alcohols as methanol, ethanol, n-propanol, i-propanol, n-butanol, i-butanol, s-butanol, t-butanol, n-pentanol, i-pentanol, neo-pentanol, n-hexanol, cyclohexanol, n-heptanol, n-octonol, n-nonanol, n-decanol, and the like), tocotrienol isomer succinates and nicotinates; the mono, di, and tri esters of O-acetylcitric acid or O-propionylcitric acid or O-butyrylcitric acid with $C_1$ to $C_{10}$ straight and branched chain aliphatic alcohols, the mono, di, and tri esters of citric acid with $C_1$ to $C_{10}$ straight and branched chain aliphatic alcohols, dibenzoate esters of poly(oxyethylene)diols having low water solubility, poly(oxypropylene)diols having low water solubility, liquid and semisolid polycarbonate oligomers, and dimethyl sulfone. The liquid to semisolid polycarbonate oligomers may be those polycarbonate oligomers prepared by the polymerization of trimethylene carbonate[poly(1,3-propanediol carbonate)], the ester exchange polymerization of diethylene carbonate with aliphatic diols or polyoxyalkane diols[poly(di-1,2-propylene glycol carbonate), or poly(tri-1,2-propylene glycol carbonate)].

Another example of biodegradable/biocompatible excipients useful in the present invention are "tocols": a family of tocopherols and tocotrienols and derivatives thereof. Tocopherols and tocotrienols are derivatives of the simplest tocopherol, 6-hydroxy-2-methyl-2-phytylchroman. Tocopherols are also known as a family of natural or synthetic compounds commonly called Vitamin E. Alpha-tocopherol is the most abundant and active form of this class of compounds. Other members of this class include β-, γ-, and δ-tocopherols and α-tocopherol derivatives such as tocopheryl acetate, succinate, nicotinate, and linoleate. Useful tocotrienols include d-δ-tocotreinols, and d-β-, d-γ-tocotrienols, and their esters.

In addition to the excipients listed above, the following excipients having very low viscosities are valued not only by themselves as carriers of drugs for injectable sustained release (ISR) formulations, but also as additives to the ISR formulations of the excipients listed above to reduce their viscosities and thereby improve syringeability. These include: perfluorodecalin; perfluorooctane; perfluorohexyloctane; the cyclomethicones, especially octamethylcyclotetrasiloxane; decamethylcyclopentasiloxane, and dodecamethylcyclohexasiloxane polydimethylsiloxanes of viscosities below about 1000 cSt; diethyl carbonate; and dipropylcarbonate.

It is also contemplated that these liquid and solid LSBBs/active agent formulations can be coatings on implanted surfaces, such as but not limited to, those on catheters, stents (cardiac, CNS, urinary, etc.), prothesis (artificial joints, cosmetic reconstructions, and the like), tissue growth scaffolding fabrics, or bones and teeth to provide a wide variety of therapeutic properties (such as but not limited to, anti-infection, anti-coagulation, anti-inflammation, improved adhesion, improved tissue growth, improved biocompatibilty). These surfaces can be from a wide variety of materials, such as but not limited to, natural rubbers, wood, ceramics, glasses, metals, polyethylene, polypropylene, polyurethanes, polycarbonates, polyesters, poly(vinyl acetates), poly(vinyl alcohols), poly(oxyethylenes), poly(oxypropylenes), cellulosics, polypeptides, polyacrylates, polymethacrylates, polycarbonates, and the like.

Active agents, or active ingredients, that may be useful in the present invention singly or in combination, as determined by one of ordinary skill in the art in light of this specification without undue experimentation, include but are not limited to:

Analgesics, Anesthetics, Narcotics such as acetaminophen; clonidine (Duraclon®, Roxane Labs.) and its hydrochloride, sulfate and phosphate salts; oxycodene (Percolone™, Endo Pharm. Inc.) and its hydrochloride, sulfate, phosphate salts; benzodiazepine; benzodiazepine antagonist, flumazenil (Romazicon®, Roche U.S. Pharm.); lidocaine; tramadol; carbamazepine (Tegretol®, Novartis Pharm.); meperidine (Demerol®, Sanofi-Synthelabo, Inc.) and its hydrochloride, sulfate, phosphate salts; zaleplon (Sonata®, Wyeth-Ayerst Labs.); trimipramine maleate (Surmontil®, Wyeth-Ayerst Labs.); buprenorphine (Buprenex®, Reckitt Benckiser Pharm.); nalbuphine (Nubain®, Endo Pharm. Inc.) and its hydrochloride, sulfate, phosphate salts; pentazocain and hydrochloride, sulfate, phosphate salts thereof; fentanyl and its citrate, hydrochloride, sulfate, phosphate salts; propoxyphene or dextroporpoxyphene and its hydrochloride and napsylate salts (Darvocet®, Eli Lilly & Co.); hydromorphone (Dilaudid®, Abbott Labs.) and its hydrochloride, sulfate, and phosphate salts; methadone (Dolophine®, Roxane Labs.) and its hydrochloride, sulfate, phosphate salts; morphine and its hydrochloride, sulfate, phosphate salts; levorphanol (Levo-Dromoran®, ICN Pharm., Inc.) and its tartrate, hydrochloride, sulfate, and phosphate salts; hydrocodone and its bitartrate, hydrochloride, sulfate, phosphate salts;

Angiostatic and/or Anti-inflammatory Steroids such as anecortive acetate (Retaane®, Alcon); tetrahydrocortisol; 4,9 (11)-pregnadien-17α,21-diol-3,20-dione and its -21-acetate salt; 11-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its 21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide (Diamox®, American Cyanamid Co.);

Nonsteroidal Anti-inflammatories such as naproxin; diclofenac; celecoxib (Celebrex®, Pfizer); sulindac; diflunisal; piroxicam; indomethacin; etodolac; meloxicam; ibuprofen; ketoprofen; r-flurbiprofen (Myriad Genetics, Inc.); mefenamic; nabumetone; tolmetin, and sodium salts of each of the foregoing; ketorolac bromethamine; ketorolac tromethamine (Acular®, Allergan, Inc.); choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, l, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; and phenylbutazone;

Angiogenesis Inhibitors such as squalamine, squalamine lactate (Evizon™, Genaear Corp.) and curcumin; Vascular endothelial growth factor (VEGF) inhibitors including pegaptanib (Macugen®, Eyetech/Pfizer), bevacizumab (Avastin®, Genentech, Inc.), concentrated shark cartilage extract (Neovastat®, IEterna Zentaris), PTK 787 (vatalanib, Schering AG/Novartis), ribozyme anti-angiogenic (Angiozyme®, Sirma Therapeutics, Inc./Chiron Corp.); AZD 6474 (Zactima®, AstraZeneca AB Ltd.), anti-angiogenesis chimeric monoclonal antibody specific VEGF receptor 2 (IMC-1C11, ImClone Sys. Inc.), isocoumarin 2-(8-hydroxy-6-methoxy-1-oxo-1H-2-benzopyran-3-yl) propionic acid (NM-3, Ilex Oncology Inc.), SU668 (Pfizer), isopropoxymethyl-12-(3-hydroxypropyl)ideno[2,1-a]pyrro[3,4-c]carbazole-5-one (CEP-5214, Cephalon), CEP-7055 (the N,N-dimethyl glycine ester prodrug of CEP-5214, Cephalon), and PTC299 (PTC Therapeutics); Integrin antagonists such as anti-$\alpha_v\beta_3$ antibody (Vitaxin®, Medimmune Inc.); RDG peptide mimetics such as S137 and S247 (Pfizer), conformationally constrained bicyclic lactam Arg-Gly-Asp-containing pseudopeptides such as ST1646 (Sigma Tau S.p.A.); DPC A803350 (Bristol-Myers Squibb), and o-guanidines (3D Pharmaceuticals Inc.); matrix metalloproteinase inhibitors such as prinomastat (AG 3340, Pfizer), (ISV-616, InSite Vision), (TIMP-3, NIH); S3304 (Shionogi); BMS 275291 (Celltech/Bristol-Myers Squibb); SC 77964 (Pfizer); ranibizumab (Lucentis®, Genentech, Inc.); ABT 518 (Abbott Labs.); CV 247 (Ivy Medical); NX-278-L anti-VEGF aptamer (EyeTech Pharm.); 2'-O-methoxyethyl antisense C-raf oncogene inhibitor (ISIS-13650, Isis Pharm., Inc./iCo Therapeuticals, Inc.); vitronectin and osteopontin antagonists (3D Pharm.); combretstatin A-4 phosphate (CA4P, OxiGene, Inc.); fab fragment α-V/β-1 integrin antagonist (Eos-200-F, Protein Design Labs); α-v/β-3 integrin antagonist (Abbott Labs.); urokinase plasminogen activator fragment (A6, Angstrom Pharm.); VEGF antagonist (AAV-PEDF, Chiron Corp.); kdr tyrosine kinase inhibitor (EG-3306, Ark Therapeutics); cytochalasin E (NIH); kallikrinin-binding protein (Med. Univ. SC); combretastatin analog (MV-5-40, Tulane); pigment-epithelium derived growth factor (Med. Univ. SC); pigment-epithelium derived growth factor (AdPEDF, GenVec, Inc.); plasminogen kringle (Med. Univ. SC); rapamycin; cytokine synthesis inhibitor/p38 mitogen-activated protein kinase inhibitor (SB-220025, GlaxoSmithKline); vascular endothelial growth factor antagonist (SP-(V5.2)C, Supratek); vascular endothelial growth factor antagonist (SU10944, Sugen/Pfizer); vascular endothelial growth factor antagonist (VEGF-R, Johnson & Johnson/Celltech); vascular endothelial growth factor antagonist (VEGF-TRAP, Regeneron); FGF1 receptor antagonist/tyrosine kinase inhibitor (Pfizer/Sugen); endostatin, vascular endothelial growth factor antagonist (EntreMed, Inc., Rockville, Md.); bradykinin B1 receptor antagonist (B-9858, Cortech, Inc.); bactericidal/permeability-increasing protein (Neuprex®, Xoma Ltd.); protein kinase C inhibitor (Hypericin, Sigma-Aldrich, St. Louis, Mo.); ruboxistaurinn mesylate (LY-333531, Eli Lilly & Co.); polysulphonic acid derivatives (Fuji Photo Film); growth factor antagonists (TBC-2653, TBC-3685, Texas Biotech. Corp.); Tunica internal endothelial cell kinase (Amgen Inc.);

Anti-bacterials including aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt;

cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof; clindamycin; clindamycin hydrochloride, sulfate, or phosphate salt; lincomycin and hydrochloride, sulfate, or phosphate salt thereof; tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; rifampin; dapsone; atovaquone; rifabutin; linezolide; polymyxin B and its hydrochloride, sulfate, or phosphate salt; sulfacetamide and its sodium salt; minocycline; and clarithromycin;

Anti-infective Agents such as 2,4-diaminopyrimidines (e.g., brodimoprim, tetroxoprim, trimethoprim); nitrofurans (e.g., furaltadone, furazolium chloride, nifuradene, nifuratel, nifurfoline, nifurpirinol, nifurprazine, nifurtoinol, nitrofuirantoin); quinolones and analogs (e.g., cinoxacin, ciprofloxacin, clinafloxacin, difloxacin, enoxacin, fleroxacin, flumequine, gatifloxacin, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin); sulfonamides (e.g., acetyl sulfamethoxypyrazine, benzylsulfamide, chloramine-b, chloramine-t, dichloramine t, n²-formylsulfisomidine, n⁴-β-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, n⁴-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole); sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone); and others (e.g., clofoctol, hexedine, methenamine, methenamine anhydromethylene-citrate, methenamine hippurate, methenamine mandelate, methenamine sulfosalicylate, nitroxoline, taurolidine, and xibomol); moxifloxacin; and gatifloxacin;

Antifungals such as amphotericin B; pyrimethamine; flucytosine; caspofungin acetate; fluconazole; griseofulvin; terbinafin and its hydrochloride, sulfate, or phosphate salt; ketoconazole; micronazole; clotrimazole; econazole; ciclopirox; naftifine; and itraconazole;

Antimalarials such as chloroquine and its hydrochloride, sulfate or phosphate salt; hydroxychloroquine and its hydrochloride, sulfate or phosphate salt; mefloquine and its hydrochloride, sulfate, or phosphate salt; atovaquone; proguanil and its hydrochloride, sulfate, or phosphate salt forms;

Antituberculosis Agents such as ethambutol and its hydrochloride, sulfate, or phosphate salt forms; aminosalicylic acid; isoniazid; pyrazinamide; ethionamide;

Antivirals such as amprenavir; interferon alfa-n3; interferon alfa-2b; interferon alfacon-1; peginterferon alfa-2b; interferon alfa-2a; lamivudine; zidovudine; amadine (Symmetrel®, Endo Pharm. Inc.) and its hydrochloride, sulfate, and phosphate salts; indinavir and its hydrochloride, sulfate, or phosphate salt; ganciclovir; ganciclovir sodium salt; famciclovir; rimantadine and its hydrochloride, sulfate, or phosphate salt; saquinavir mesylate; foscarnet; zalcitabine; ritonavir; ribavirin; zanamivir; delavirdine mesylate; efavirenz; amantadine and its hydrochloride, sulfate, or phosphate salt; palivizumab; oseltamivir and its hydrochloride, sulfate, or phosphate salt; abacavir and its hydrochloride, sulfate, or phosphate salt; valganciclovir and its hydrochloride, sulfate, or phosphate salt; valacyclovir and its hydrochloride, sulfate, or phosphate salt; didanosine; nelfinavir mesylate; nevirapine; cidofovir; acyclovir; trifluridine; penciclovir; zinc oxide; zinc salicylate; zinc salts of all isomers of tocopherol hemisuccnic acid; zinc salts of straight, branched, saturated, and unsaturated chain $C_2$ to $C_{20}$ aliphatic carboxylic acids; zinc pyruvate; zinc lactate; zinc ester complexes; and zinc acetoacetonate or zinc acetoacetic ester complexes;

Anti HIV/AIDS agents including stavudine, reverset (Pharmasset, Inc./Incyte Corp.), ACH-126443 (also known as Elvucitabine or Beta-L-Fd4C, Achillion Pharm., Inc.), MIV-310 (Boehringer Ingelheim), Zerit® (stavudine, d4T, Bristol-Meyers Squibb), Ziagen® (abacavir sulfate, GlaxoSmithKline), Viread® (tenofovir disoprixil fumerate, Gilead Sci., Inc.), hivid (Roche), Emtriva (emtricitabine, Gilead Sci., Inc.), delavirdine (Rescriptor®, Pfizer), AG-1549 (Pfizer), DPC-083 (Bristol-Myers Squibb), NSC-675451 (Advanced Life Sciences), IMC-125 (Tibitec), azidicarbonamide, modified tripeptide glycyl-prolyl-glycine-amide (GPG-NH2, Tripep AB), Immunitin™ (Hollis-Eden Pharm.), Cytolin® (Amerimmune Pharm. Inc.), PEHRG214 (Virionyx Corp.), MDX-010 (Gilead Sci., Inc.), TXU-PAP (Wayne Hughes Inst), Proleukin® (aldesleukin, Chiron Corp.), BAY 50-4798 (Bayer), BG-777 (Virocell), Crixivan® (Indinovir sulfate, Merck & Co., Inc.), Fuzeon® (enfuvirtide, Roche Labs. Inc.), WF-10 (Oxo Chemie), Ad5 Gag vaccine (Merck), APL400-003 and 047 (Wyeth), Remune® (Orchestra Therapeutics, Inc.), MVA-BN Nef (Bavarian Nordic), GTU® MultiHIV vaccine (FIT Biotech Oyj Plc.);

Insulins such as Novolog® (insulin aspart [rDNA origin]) and Novolin® products (Novo Nordisk Inc.); Humalog® (insulin lispro [rDNA origin]), Humalog® 75/25 and 50/50 (mixtures of insulin lispro protamine suspension and insulin lispro), and Humulin® products (regular human insulin

[rDNA origin], Eli Lilly & Co.); Lantus® (insulin glargine [rDNA origin], Sanofi Aventis U.S. LLC); porcine and bovine insulins;

Glucagon-like Peptide-1 (Glp1) and analogs (for diabetes therapy and appetite suppression, cardiac protection) (see Keiffer et al., 20 Endocr Rev., 876-913 (1999) such as liraglutide (Novo Nordisk Inc.); Glp1 receptor stimulators such as such as Byetta® products (exenatide, and incretin mimetic, Amylin Pharm., Inc./Eli Lilly & Co.) and ZP-10 (Zealand Pharma A/S); Glp-1-albumin (ConjuChem Inc.); and Dpp-IV inhibitors (which inhibit enzyme attack on Glp-1) such as Galvus® (vildagliptin, formerly LAF237, Novartis), Januvia® sitagliptin, formerly MK-0431, Merck & Co.); saxagliptin (formerly BMS-477188, Bristol-Myers Squibb), and GSK23A (GlaxoSmithKline);

Alpha Androgenergic Agonist such as brimonidine tartrate; Beta Adrenergic Blocking Agents such as betaxolol and its hydrochloride, sulfate, or phosphate salt; levobetaxolol and its hydrochloride, sulfate, or phosphate salt; and timolol maleate;

Carbonic Anhydrase Inhibitors such as brinzolamide; dorzolamide and its drochloride, sulfate, or phosphate salt; and dichlorphenamid;

Mast Cell Stabilizers such as pemirolast and its potassium salt; nedocromil and its sodium salt; cromolyn and its sodium salt;

Miotics (Cholinesterase Inhibitors) such as demecarium bromide;

Prostaglandins such as bimatoprost; travoprost; and latanoprost;

Antihistamines such as olopatadine and its hydrochloride, sulfate, or phosphate salt forms; fexofenadine and its hydrochloride, sulfate, or phosphate salt; azelastine and its hydrochloride, sulfate, or phosphate forms; diphenhydramine and its hydrochloride, sulfate, or phosphate forms; and promethazine and its hydrochloride, sulfate, or phosphate forms;

Antimicrotubule Agents such as Taxoids including paclitaxel (Taxol®, Bristol-Myers Squibb); vincristine (Oncovin®, Eli Lilly & Co.) and its hydrochloride, sulfate, or phosphate salt forms; vinblastine (Velbe®, Eli Lilly & Co.) and its hydrochloride, sulfate, or phosphate salt; vinorelbine (Navelbine®, Fabre Pharm. Inc.); colchicines; docetaxel (Taxotere®, Sanofi-Aventis U.S. LLC); RPR-109881 (Sanofi-Aventis); LIT 976 (Sanofi-Aventis); BMS 188797 and BMS 184476 (Bristol-Myers Squibb); DJ 927 (Daiichi Pharm. Inc.); DHA-paclitaxel (Taxoprexin®, Protarga, Inc.); Epothilones including epothiloneB such as patupilone (EPO 906, Novartis/generic), BMS 247550 and BMS-310705 (Bristol-Myers Squibb), epothilone D (KOS 862, Kosan Biosci. Inc.), and ZK EPO (Schering AG);

Antineoplastic agents such as doxorubicin and its hydrochloride, sulfate, or phosphate salt; idarubicin and its hydrochloride, sulfate, or phosphate salt; daunorubicin and its hydrochloride, sulfate, or phosphate salt; dactinomycin; epirubicin and its hydrochloride, sulfate, or phosphate salt; dacarbazine; plicamycin; mitoxantrone (Novantrone®, EMD Serono Inc.) and its hydrochloride, sulfate, or phosphate salt; valrubicin; cytarabine; nilutamide; bicalutamide; flutamide; anastrozole; exemestane; toremifene; femara; tamoxifen and tamoxifen citrate; temozolomide (Temador, Schering-Plough Corp.); gemcitabine and its hydrochloride, sulfate, or phosphate salt; topotecan and its hydrochloride, sulfate, or phosphate salt; vincristine and its hydrochloride, sulfate, or phosphate salt; liposomal vincristine (Teva Pharm.); methotrexate and methotrexate sodium salt; cyclophosphamide; estramustine sodium phosphate; leuprolide and leuprolide acetate; goserelin and goserelin acetate; estradiol; ethinyl estradiol; Menest® esterified estrogens (Monarch Pharm., Inc.); Premarin® conjugated estrogens (Wyeth Pharm. Inc.); 5-flurouracil; bortezamib (Velcade®, Millenium Pharm., Inc.);

Antiapoptotics such as desmethyldeprenyl (DES, RetinaPharma);

Aldose Reductase Inhibitors such as GP-1447 (Grelan); NZ-314 (parabanic acid derivative, Nippon Zoki); SG-210 (Mitsubishi Pharma/Senju); and SJA-7059 (Senju);

Antihypertensives such as candesartan cilexetil (Atacand®, Takeda Pharm.Co./AstraZeneca AB); losartan (Cozaar® and Hyzaar®, Merck & Co.); and lisinopril (Zestril®, AstraZeneca AB and Prinivil®, Merck & Co.);

Antioxidants such as benfotiamine (Albert Einstein Col. Of Med./WorWag Pharma); ascorbic acid and its esters; tocopherol isomers and their esters; and raxofelast (IRFI 016, metabolized to IRFI 005, Biomedica Foscama);

Growth Hormone Antagonists such as octreotide (Sandostatin®, Novartis); and pegvisomant (Somavert®, Pfizer);

Vitrectomy Agents such as hyaluronidase (Vitrase®, ISTA Pharm., Inc.);

Adenosine Receptor Antagonist such as A2B adenosine receptor antagonist (ATL-754, Adenosine Therapeutics, LLC);

Adenosine Deaminase Inhibitor such s pentostatin (Nipent®, SuperGen Inc.);

Glycosylation Antagonists such as pyridoxamine (Pyridorin™, NephroGenex Inc.);

Anti-Ageing Peptides, such as Ala-Glu-Asp-Gly (Epitalon, Geron Corp.);

Topoisomerase Inhibitors such as doxorubicin (Adriamycin®, Pfizer; Caelyx™ Schering-Plough Pharm.; Doxil®, Johnson & JohnsonPharmacia/generics); daunorubicin (DaunoXome®, Gilead Sci.); etoposide (Vepesid® and Etopophos®, Bristol-Myers Squibb); idarubicin (Idamycin PFS®, Pfizer); irinotecan (Camptosar®, Pfizer); topotecan (Hycamtin®, GlaxoSmithKline); epirubicin (Ellence®, Pfizer); and raltitrexed (Tomudex®, AstraZeneca);

Anti-metabolites such as methotrexate (generic) and its sodium salt; 5-fluorouracil (Adrucil®, Teva Pharm. U.S.A.); cytarabine (Cytosar®, Upjohn Co.); fludarabine (Fludara®, Bayer HealthCare Pharm.) and its forms as salts with acids; gemcitabine (Gemzar®, Eli Lilly & Co.); capecitabine (Xeloda®, Roche Labs. Inc.); and perillyl alcohol (POH, Endorex);

Alkylating Agents such as chlorambucil (Leukeran®, GlaxoSmithKline); cyclophosphamide (Cytoxan®, Bristol-Meyers Squibb); methchlorethanine (generic); cisplatin (Platinol®, Bristol-Meyers Squibb); carboplatin (Paraplatin®, Bristol-Myers Squibb); temozolominde (Temodar®, Schering Corp.) and oxaliplatin (Eloxatin® Sanofi-Synthelabo, Inc.);

Anti-androgens such as flutamide (Eulexin®, Schering-Plough); nilutamide (Nilandron®, Sanofi-Aventis); bicalutamide (Casodex®, AstraZeneca);

Anti-oestrogens such as tamoxifen (Nolvadex®, AstraZeneca); toremofine (Fareston, Orion/Shire); fulvestrant (Faslodex®, AstraZeneca); arzoxifene (Eli Lilly & Co.); anastrozole (Arimidex™, AstraZeneca); letrozole (Femera™, Novartis); formestan (Lentaron®, Novartis); exemestane (Aromasin®, Pfizer); goserelin acetate (Zoladex®, AstraZeneca); lasoxifene (Pfizer); ERA-923 (Ligand Pharm. Inc./Wyeth); DCP 974 (DuPont/Bristol-Myers Squibb); ZK 235253, ZK 911703, and ZK 230211 (Schering AG);

Oncogene Activation Inhibitors, including for example, Bcr-Abl Kinase Inhibition such as imatinib mesylate (Gleevec™, Novartis); Her2 Inhibition such as trastuzumab (Herceptin®, Genentech, Inc.); MDX 210 (Medarex, Inc.);

E1A (Targeted Genetics Corp.); ME 103 and ME 104 (Pharmexa); rhuMAb-2C4 (Omnitarg, Genentech, Inc.); Cl-1033 (Pfizer); PKl 166 (Novartis Pharma AG); GW572016 (GlaxoSmithKline); EGFr Inhibitors such as cetuximab (Erbitux™ Imclone Sys. Inc.); EGFr Tyrosine Kinase Inhibitors such as gefitinib (Iressa®, formerly ZD 1839, AstraZeneca); erlotinib (Tarceva, Genentech, Inc./OSI Pharm., Inc.); ABX-EGF (Abgenix/Amgen); erbB receptor inhibitor (Cl-1033, Pfizer); EMD 72000 (Merck KgaA); lapatinib (GW572016, GlaxoSmithKline); EKB 569 (Wyeth); PKI 166 (Novartis); and BIBX 1382 (Boehringer Ingleheim); Farnesyl Transferase Inhibitors such as tipifamib (Zarnestra®, Johnson & Johnson); lonafarnib (Sarasar™, Schering-Plough); BMS-214,662 (Bristol-Myers Squibb); AZ3409 (AstraZeneca); CP-609754 and CP-663427 (OSI Pharmaceuticals/Pfizer); Arglabin (NuOncology Labs Inc.); RPR-130401 (Aventis Pharm.); A-176120 (Abbott Labs.); BIM 46228 (Biomeasure, Inc.); LB 42708 and LB 42909 (LG Chem, Ltd.); PD 169451 (Pfizer); and SCH226374 (Schering-Plough); Bcl-2 Inhibitors such as BCL-X (Isis Pharm., Inc.); ODN 2009 (Novartis Pharm.); GX 011 (Gemin X Biotech. Inc.); and TAS 301 (Taiho Pharm. Co.); Cyclin Dependent Kinase Inhibitors such as flavopiridol (generic, Aventis Oncol.); CYC202 (R-roscovitine, Cyclacel Ltd.); BMS 387032, BMS 239091 and BMS 250904 (Bristol-Myers Squibb); CGP 79807 (Novartis Pharm.); NP102 (Nicholas Piramal India Ltd.); and NU 6102 (AstraZeneca); Protein Kinase C Inhibitors such as Affinitac™ (Isis Pharm., Inc./Eli Lilly & Co.); midostaurin (PKC 412, Novartis/generic); bryostatin (Aphios Corp.); KW 2401 (Kyowa Hakko Kogyo/Keryx Biopharm.); LY 317615 (Eli Lilly & Co.); perifosine (Keryx Biopharm); and balanol (SPC 100840, Sphinx Pharm./Eli Lilly & Co.)

Telomerase Inhibitors such as GRN163 (Geron Corp./Kyowa Hakko Kogyo) and G4T 405 (Aventis);

Antibody Therapy including Herceptin® (trastuzumab Genentech, Inc.); MDX-H210 (Medarex, Inc.); SGN-15 (Seattle Genetics); H11 (Viventia); Therex (Antisoma); rituximan (Rituxan®, Genentech); Campath (ILEX Oncology/Millennium/Shering); Mylotarg (Celltech/Wyeth); Zevalin (IDEC Pharmaceuticals/Schering); tositumomab (Bexxar, Corixa/SmithKline Beecham/Coulter); epratuzumab (Lymphocide, Immunomedics/Amgen); Oncolym (Techniclone/Schering AG); Mab Hu1D10 antibody (Protein Design Laboratories); ABX-EGF (Abgenix); infleximab (Remicade®, Centocor) and etanercept (Enbrel, Wyeth-Ayerst);

Antisense Oligonucleotides such as Affinitac (Isis Pharmaceuticals/Eli Lilly & Co.); and Genasence (Genta/Aventis);

Fusion Proteins such as denileukin diftitox (Ontak, Ligand);

Luteineizing Hormone Releasing Hormone (LHRH) Agonists aka Gonadotropin Releasing Hormone (GnRH) Agonists such as goserelin (Zoladex, AstraZeneca); leuporelin (Lupron, Abbott/Takeda); leuporelin acetate implant (Viadur, ALZA/Bayer and Atigrel/Eligard, Atrix/Sanofi-Synthelabo); and triptorelin (Trelstar, Pharmaceuticals);

Tyrosine Kinase Inhibitors/Epidermal Growth Factor Receptor Inhibitors such as gefitinib (Iressa, AstraZeneca, ZD 1839); trastuzumab (Herceptin, Genentech); erlotinib (Tarceva, OSI Phanmaceuticals, OSI 774); cetuximab (Erbitux, Imclone Systems, IMC 225); and pertuzumab (Omnitarg, Genentech, 2C4);

Ribonucleotide Reductase Inhibitors such as gallium maltolate (Titan);

Cytotoxins such as Irofulven (MGI 114, MGI Pharma);

IL2 Therapeutics such as Leuvectin (Vical);

Neurotensin Antagonist such as SR 48692 (Sanofi-Synthelabo);

Peripheral Sigma Ligands such as SR 31747 (Sanofi-Synthelabo);

Endothelin ETA/Receptor Antagonists such as YM-598 (Yamanouchi); and atrasentan (ABT-627, Abbott);

Antihyperglycemics such as metformin (Glucophage, Bristol-Myers Squibb) and its hydrochloride, sulfate, phosphate salts; and miglitol (Glyset, Pharmacia/Upjohn);

Anti-glaucoma Agents such as dorzolamide (Cosopt, Merck); timolol; betaxolol and its hydrochloride, sulfate, phosphate salts; atenolol; and clorthalidone;

Anti-(Chromatin Modifying Enzymes) such as suberoylanilide hyroxaxamic acid (Aton/Merck);

Agents for Obesity Management, such as glucagon-like-peptides, phendimettrazine and its tartrate, hydrochloride, sulfate, phosphate salts; methamphetamine and its hydrochloride, sulfate, phosphate salts; and sibutramine (Meridia, Abbott) and its hydochloride, sulfate, phosphate salts;

Treatments for Anemia such as epoetin alpha (Epogen, Amgen); epoetin alpha (Eprex/Procrit, Johnson & Johnson); epoetin alpha (ESPO, Sankyo and Kirin); and darbepoetin alpha (Aranesp, Amgen); epoetin beta (NeoRecormon, Roche); epoetin beta (Epogen, Chugai); GA-EPO (Dynepo, TKT/Aventis); epoetin omega (Elanex/Baxter); R 744 (Roche); and thrombopoetin (Genetech/Pharmacia);

Treatments for Emesis such as promethazine (Phenergan, Wyeth); prochlorperazine; metoclopramide (Reglan, Wyeth); droperidol; haloperidol; dronabinol (Roxane); ondasetron (Zofran, GlaxoSmithKline); ganisetron (Kytril, Roche); dolasetron (Anzemet, Aventis); indisetron (NN-3389, Nisshin Flour/Kyorin); aprepitant (MK-869, Merck); palonosetron (Roche/Helsinn/MGI Pharma); lerisetron (FAES); nolpitantium (SR 14033, Sanofi-Synthelabo); R1124 (Roche); VML 670 (Vernalis, Eli Lilly & Co.); and CP 122721 (Pfizer);

Neutropaenia Treatments such as filgrastim (Neupogen, Amgen); leukine (Immunex/Schering AG); filgrastim-PEG (Neulasta, Amgen); PT 100 (Point Therapeutics); and SB 251353 (GlaxoSmithKline);

Tumor-induced Hypercalcaemia Treatments such as Bonviva (GlaxoSmithKline); ibandronate (Bondronat, Roche); pamidronate (Aredia, Novartis); zolendronate (Zometa, Novartis); clodronate (Bonefos, generic); incadronate (Bisphonal, Yamanouchi); calcitonin (Miacalcitonon, Novartis); minodronate (YM 529/Ono 5920, Yamanouchi/Ono); and anti-PTHrP (CAL, Chugai);

Blood Anticoagulants such as Argathroban (GlaxoSmithKline); warfarin (Coumadin, duPont); heparin (Fragmin, Pharmacia/Upjohn); heparin (Wyeth-Ayerst); tirofiban (Aggrastat, Merck) and its hydrochloride, sulfate, phosphate salts; dipyridamole (Aggrenox, Boehringer Ingelheim); anagrelide (Agrylin, Shire US) and its hydrochloride, sulfate, phosphate salts; epoprostenol (Flolan, GlaxoSmithKline) and its hydrochloride, sulfate, phosphate salts; eptifibatide (Integrilin, COR Therapeutics); clopidogrel (Plavix, Bristol-Myers Squibb) and its hydrochloride, sulfate, or phosphate salts; cilostazol (Pletal, Pharmacia/Upjohn); abciximab (Reopro, Eli Lilly & Co.); and ticlopidine (Ticlid, Roche);

Immunsuppressive Agents such as sirolimus (rapamycin, Rapamune®, Wyeth-Ayerst); tacrolimus (Prograf, FK506); and cyclosporins;

Tissue Repair Agents such as Chrysalin (TRAP-508, Orthologic-Chrysalis Biotechnology);

Anti-psoriasis Agents such as anthralin; vitamin D3; cyclosporine; methotrexate; etretinate, salicylic acid; isotretinoin; and corticosteroids;

Anti-acne Agents such as retinoic acid; benzoyl peroxide; sulfur-resorcinol; azelaic acid; clendamycin; erythromycin; isotretinoin; tetracycline; minocycline;

Anti-skin parasitic Agents such as permethrin and thiabendazole;

Treatments for Alopecia such as minoxidil and finasteride;

Contraceptives such as medroxyprogesterone; norgestimol; desogestrel; levonorgestrel; norethindrone; norethindrone; ethynodiol; and ethinyl estradiol;

Treatments for Smoking Cessation including nicotine; bupropion; and buspirone;

Treatments for Erectile Disfunction such as alprostadil; and Sildenafil;

DNA-alkyltranferase Agonist including temozolomide;

Metalloproteinase Inhibitor such as marimastat;

Agents for management of wrinkles, bladder, pro static and pelvic floor disorders such as botulinum toxin;

Agents for management of uterine fibroids such as pirfenidone, human interferin-alpha, GnRH antagonists, Redoxifene, estrogen-receptor modulators;

Transferrin Agonist including TransMID™ (modified diphtheria toxin conjugated to transferrin, Tf-CRM107, Xenova Group Ltd.);

Interleukin-13 Receptor Agonist such as IL-13-PE38QQR (Neopharm);

Nucleic acids such as small interfering RNAs (siRNA) or RNA interference (RNAi), particularly, for example siRNAs that interfere with VEGF expression;

and Psychotherapeutic Agents including Anti-anxiety drugs such as chlordiazepoxide; diazepam; chlorazepate; flurazepam; halazepam; prazepam; clorazepam; quarzepam; alprazolam; lorazepam; orazepam; temazepam; and triazolam; and Anti-psychotic drugs such as chlorpromazine; thioridazine; mesoridazine; trifluorperazine; fluphenazine; loxapine; molindone; thiothixene; haloperidol; pimozide; and clozapine.

Those of ordinary skill in the art will appreciate that any of the foregoing disclosed active agents may be used in combination or mixture in the pharmaceutical formulations of the present invention. Such mixtures or combinations may be delivered in a single formulation, or may be embodied as different formulations delivered either simultaneously or a distinct time points to affect the desired therapeutic outcome. Additionally, many of the foregoing agents may have more than one activity or have more than one therapeutic use, hence the particular category to which they have been ascribed herein is not limiting in any way. Similarly, various biodegradable, biocompatible excipients may be used in combination or in mixtures in single or multiple formulations as required for a particular indication. These mixtures and combinations of active agents and excipients may be determined without undue experimentation by those of ordinary skill in the art in light of this disclosure.

The formulations of the present invention may be sterilized for use by methods known to those of ordinary skill in the art. Autoclaving and e-beam have been used in informal studies of several embodiments and have not appeared to have significant impact. Similarly, informal stability studies indicate acceptable stability of several embodiments. Additionally, reproducibility between aliquots and lots is very good, with a standard deviation of less than five percent or better. Hence, standard pharmaceutical manufacturing techniques are readily applied to the technologies described herein.

An example embodiment of the present invention comprises the active agent dexamethasone and the excipient benzyl benzoate. Dexamethasone is a glucocorticoid and typically used in the form of the acetate or disodium phosphate ester. Glucocorticoids are adrenocortical steroids suppressing the inflammatory response to a variety of agents that can be of mechanical, chemical or immunological nature. Administration of dexamethasone can be topical, periocular, systemic (oral) and intravitreal. Doses vary depending on the condition treated and on the individual patient response. In ophthalmology, dexamethasone sodium phosphate (Decadron®, Merck & Co.) as a 0.1% solution has been widely used since its introduction in 1957. The ophthalmic dose depends on the condition treated. For control of anterior chamber inflammation, the-topical dose is usually 1 drop, 4 times a day for up to a month following surgery (around 0.5 mg per day). For control of posterior segment inflammation, periocular injections of 4 mg of dexamethasone, or daily oral administration of 0.75 mg to 9 mg of dexamnethasone in divided doses are not uncommon. Intravitreal injections of 0.4 mg of dexamethasone have been administered in conjunction with antibiotics for the treatment of endophthalmitis.

Regarding benzyl benzoate (CAS 120-51-4, FW 212.3), previously the oral administration of benzyl benzoate was claimed to be efficacious in the treatment of intestinal, bronchial, and urinary ailments, but its use has been superseded by more effective drugs. Presently, it is topically applied as a treatment for scabies and pediculosis. Goodman & Gilman's THE PHARMACOLOGICAL BASIS OF THERAPEUTICS 1630 (6th ed., 1980); FDA approval, Fed Reg. 310.545(a)(25)(i). Benzyl benzoate is approved in minor amounts in foods as a flavoring (FDA, Title 21, vol. 3, ch I, subch B, part 172(F), §172.515), and as a component in solvents for injectable drug formulations (e.g., Faslodex® and Delestrogen®).

Benzyl benzoate is a relatively nontoxic liquid which when applied topically in the eye results in no damage. Grant, TOXICOLOGY OF THE EYE 185 (2d ed., 1974). Its oral $LD_{50}$ in humans is estimated to be 0.5 g/kg-5.0 g/kg. Gosselin et al., II CLIN TOX OF COMMERCIAL PROD. 137 (4th ed., 1976). In vivo, benzyl benzoate is rapidly hydrolyzed to benzoic acid and benzyl alcohol. The benzyl alcohol is subsequently oxidized to benzoic acid, which is then conjugated with glucuronic acid and excreted in the urine as benzoylglucuronic acid. To a lesser extent, benzoic acid is conjugated with glycine and excreted in the urine as hippuric acid. HANDBOOK OF PESTICIDE TOXICOLOGY 1506 (Hayes & Laws, eds., 1991).

Dexamethasone, when mixed with benzyl benzoate, forms a uniform suspension. A dexamethasone/benzyl benzoate formulation of 25% is easily syringeable. When the suspension is injected slowly into the posterior segment of the eye, for example, a uniform spherical deposit (reservoir) is formed in the vitreous body. The reservoir maintains its integrity and in vivo "breakage" has not been observed ophthalmoscopically. Dexamethasone is then released slowly into the vitreous humor of the posterior segment. Dexamethasone and benzyl benzoate are eventually metabolized to byproducts that are excreted in the urine.

Similarly, triamcinolone acetonide (TA) in benzyl benzoate forms a syringeable suspension that retains its integrity and in vivo. In rabbit studies involving intraocular injection of TA/benzyl benzoate formulations, described below, near zero-order release of TA has been observed in vivo for more than one year. Smaller doses result in more-rapid release profiles, such that the TA is released over a six-month period. Both Dex and TA formulations may be useful in treating the eye following cateract surgery or replacement.

Further regarding cateract surgery and other treatments or diseases of the eye, an aspect of the invention provides for a composition comprising an active agent and the LSBB excipient useful for the treatment of iris neovascularization from cataract surgery, macular edema in central retinal vein occlusion, cellular transplantation (as in retinal pigment cell transplantation), cystiod macular edema, psaudophakic cystoid macular edema, diabetic macular edema, pre-phthisical ocular hypotomy, proliferative vitreoretinopathy, proliferative diabetic retinopathy, exudative age-related macular degeneration, extensive exudative retinal detachment (Coat's disease), diabetic retinal edema, diffuse diabetic macular edema, ischemic ophthalmopathy, chronic focal immunalogic corneal graft reaction, neovascular glaucoma, pars plana vitrectomy (for proliferative diabetic retinopathy), pars plana vitrectomy for proliferatve vitreoretinopathy, sympathetic ophthalmia, intermediate uveitis, chronic uveitis, intraocular infection such as endophthalmitis, and/or Irvine-Gass syndrome.

Another embodiment of the invention provides formulations and uses of the tocopherols and/or tocotrienols and their esters with insulins for the transdermal delivery of the insulins in the management of diabetes. Tocopherols and/or the tocotrienols and their esters possess outstanding capabilities to carry therapeutic agents, especially moderate molecular weight proteins such as the insulins, through the skin into the body. Indeed, it is contemplated that wide variety of other therapeutic agents (such as steroids, NSAIDs, antibiotics, hormones, growth factors, anti-cancer agents, etc.) may be available for effective transdermal delivery formulations with the tocopherols and/or tocotrienols and their esters.

The advantages to bypassing oral drug delivery that allow the enzymatic transformations of the liver and the digestive processes of the gut (and also engender gastric distresses) have inspired research to find alternative methods. A prime example is insulin therapy for diabetes. Several tutorials and reviews of the present state of insulin therapies are: Owens, 1 Nature Reviews/Drug Discovery 529-540 (2002); Cefalu, 113(6A) Am J Med 25S-35S (2002); Nourparvar et al., 25(2) Trends Pharmacol Sci, 86-91 (2004). Avoidance of daily multiple painful subcutaneous injections has led to alternative routes such as buccal/sublingual, rectal, intranasal, pulmonary, and transdermal. Yet no completely acceptable alternatives to injection have been established. Most promising are pulmonary systems (Exubera®, insulin human [rDNA origin]) Inhalation Powder, Pfizer; AERx® iDMS, liquid aerosol insulin formulation, Novo Nordisk) and as disclosed here novel transdermal delivery formulations involving the tocopherols and/or tocotrienols and their esters as penetrating vehicles for therapeutic agents.

The desirability of simple and painless transdermal delivery of insulin and other therapeutic agents has inspired a number of transdermal approaches (iontophoresis [electrical charge]; phonophoresis (ultrasound); photoenhancement (pulsed laser); heat; lipid vesicles; and penetrating agents [DMSO, NMP, etc.]) over the years with incomplete results. Transdermal delivery is considered to be hindered by the skin's relatively impermeability to large hydrophilic polypeptides such as insulin. The present invention, however, provides effective levels of insulin delivered in a sustained release fashion into the bloodstream when applied as intimate mixtures with α-tocopheryl acetate onto the skin. In a mouse model, effective levels of insulin were delivered in a sustained release fashion into the bloodstream of a mouse when applied as intimate mixtures with α-tocopheryl acetate onto the mouse skin.

Because tocopherols have long been ingredients in sunscreen and cosmetic formulations, there are numerous references in the literature to the tocopherols being applied to the skin and demonstrations of their migrating through the skin. See e.g., Zondlo, 21(Suppl 3) Int'l J Toxicol, 51-116 (2002). These reports show the ease and safety with which the tocopherols can penetrate skin, but none disclose any use of the tocopherols as penetration enhancers or carriers of therapeutic agents through the skin into the body. Indeed, a recent review of 102 chemical penetration enhancers for transdermal drug delivery did not mention the tocopherols or tocotrienols. Karande et al., 102(13) Proc Natl Acad Sci USA, 4688-93 (2005).

Tocopherol formulations that allow the facile and effective transport of therapeutic agents through the skin into the body may employ d, l, and dl isomers of alpha, beta, gamma and delta tocopherols and their esters (formates, acetates, propionates, $C_4$ to $C_{20}$ straight and branched chain aliphatic acid esters, maleates, malonates, fumarates, succinates, ascorbates, and nicotinates); d, l, and dl isomers of alpha, beta, gamma, and delta tocotrienols and their esters (formates, acetates, propionates, $C_4$ to $C_{20}$ straight and branched chain aliphatic acid esters, maleates, malonates, fumarates, succinates, ascorbates, and nicotinates).

Another embodiment of the present invention, further related to the tocopherols, provides to formulations of 2-acetyloxy benzoic acid and its aliphatic esters with tocopherols and tocotrienols and licorice extracts. In particular, this aspect provides for injectable, ingestable or topical formulations employing the tocopherols and/or tocotrienols and/or licorice extracts with 2-acetyloxybenzoic acid (2-ABA) and certain of its aliphatic esters, that allow all the well-known medicinal benefits of 2-ABA and its aliphatic esters while substantially avoiding the gastric toxicities normally associated with the ingestion of 2-ABA itself.

Unlike the more recently developed specific COX-2 inhibiting nonsteroidal anti-inflammatories such as celecoxib (Celebrex®, Pfizer), rofecoxib (Vioxx®, Merck), and the like, there is the confidence that decades of pharmaceutical experience with 2-ABA have well defined its benefits and disadvantages. The full benefits and problems of the specific COX-2 inhibitors are still being discovered. In the case of the "traditional" NSAIDs such as 2-ABA, ibuprofen, naproxen, ketoprofen, diclofenac, indimethacin, etc., evidence accumulates on the damage they do to the stomach and small bowel. Although the specific COX-2 inhibitors have demonstrated lower gastrointestinal problems than 2-ABA, serious cardiovascular problems associated with specific COX-2 inhibitors are surfacing. As for 2-ABA, its general analgesic anti-inflammatory benefits are legendary; and as the chemistries of both of its COX-1 and COX-2 inhibitions are revealed the cardioprotective properties associated with its COX-1 inhibition are in striking contrast to the cardiovascular safety problems of the COX-2 only inhibitors. The reason for 2-ABA's gastrointestinal toxicity has been ascribed to its COX-1 inhibition. And indeed the lower order of gastrointestinal problems of celecoxib, rofecoxib, and the like is seen to be due to their COX-2 only inhibition. But, interestingly, the normal intestinal appearances in the COX-1 knockout animals point to more subtle reasons for 2-ABA's gastrointestinal toxicity, in which the concomitant inhibition of both COX-1 and COX-2 enzymes may be the problem.

Whatever the mechanisms for 2-ABA's gastrointestinal toxicity, the well demonstrated benefits of 2-ABA in other areas of the body are incentives to seek ways to get the molecule past the gut without damage. Of course injection or topical applications avoid the gut, but the major mode of current administration remains ingestion. Three distinctly different methods of lowering the gut irritation of ingested 2-ABA have been reported. The first, and most successful, is the discovery in studies in rats and pigs by Rainsford and Whitehouse reported in 1980 (10(5) Agents & Actions, 451-56), that the methyl, ethyl, and phenyl esters of 2-ABA elicit practically no gastric ulcerogenic activity and yet still have nearly all the anti-inflammatory properties of 2-ABA. Surprisingly, the investigation of oral administrations of the esters of 2-ABA has not been pursued further. Topical applications of 2-ABA esters for acne control, sunscreen, and placating insect bites have been reported. See U.S. Pat. No. 4,244,948, No. 4,454,122, No. 3,119,739. The second method of reducing 2-ABA gastric distress recommends diets rich in tocopherols and/or tocotrienols, resulting ing about a 30% to 40% reduction in lesion formation which is not as extensive as that provided by 2-ABA esters. See e.g., Jaarin et al., 13(Suppl) Asia Pac J Clin Nutr, 5170 (2004); Nafeeza et al., 11(4) Asia Pac J Clin Nutr 309-13 (2002); Sugimoto et al., 45(3) Dig Dis Sci, 599-605 (2000); Stickel et al, 66(5) Am J Clin Nutr 1218-23 (1997). The third method of reducing gastric stress is by the concomitant oral administration of licorice extract (glycyrrhizin) with 2-ABA. Rainsford & Whitehouse, 21 Life Sciences 371-78 (1977); Dehpour et al., 46 J Pharm Pharmacol 148-49 (1994). This gave 66% to 80% reduction in ulceration compared to 2-ABA alone. Formulations combining 2-ABA or its esters, the tocopherols (or their acetates) and/or tocotrienols (or their acetates), and licorice extracts in combination have not been tried.

Treatment of inflammatory conditions of the eye or joints by direct injection avoids gastric distress and the inefficient systemic exposure of the ingestion route. Ingestion in humans of the commonly prescribe dosages of 2-ABA (0.650-1.3 g) leads to combined 2-ABA/2-hydroxy benzoic acid (2-HBA) levels in the plasma of about 20-100 µg/ml. Kralinger et al., 35 Ophthalmic Res 107 (2003). Studies in rabbit eyes indicate that at these plasma levels the concentration of 2-ABA/2-HBA in the vitreous is in the range of 5-10 µg/ml. The 2-ABA level is much lower than 2-HBA since within 30 minutes in the plasma about 97% of the 2-ABA is hydrolyzed to 2-HBA. Once remaining 2-ABA reaches the vitreous its rate of hydrolysis in that environment is greatly reduced. There an initial level of 4 µg/ml is halved in 1.5-2 hours, the half-life of 2-HBA is not well defined since its initial concentration is increased by the conversion of 2-ABA to 2-HBA; but the half life is probably twice that of 2-ABA. Valeri et al., 6(3) Lens & Eye Toxicity Res 465-75 (1989). This highlights another advantage of direct injection over oral (systemic) administration: injection avoids the substantial loss of the acetyl group in the hydrolysis of 2-ABA before it reaches its target. It has been shown that the major method of 2-ABA's anti-inflammatory action is its ability deactivate the COX-1 and COC-2 enzymes by irreversibly inserting its acetyl group into these enzymes. Roth & Majerus, 56 J Clin Invest 624-32 (1975). The ID50 for this reaction in the eye has been determined to be in the range of 0.9-9.0 µg/ml. Higgs et al, 6(Suppl) Agents & Actions 167-75 (1979). Kahler et al., 262(3) Eur J Pharmacol 261-269 (1994).

One example of an injectable sustained release (ISR) 2-ABA formulation in the eye is the injection of a 1.0 ml tamponade of silicone oil containing 1.67 mg into rabbit eye vitreous chamber. Only 2-HBA was measured in the study, which observed an initial burst of 640 µg/ml within 6 hours. 2-HBA decreased to 20 µg/ml in 20 hours and 5 µg/ml after 120 hours. Kraling al., 21(5) Retina 513-20 (2001). The use of the ethyl ester of 2-ABA in ISR formulations should give longer half lives (longer sustained deliveries) than 2-ABA since the ester is more hydrophobic. Also, the incorporation of 2-ABA esters or 2-ABA into hydrophobic excipients such as the tocopherols (or their acetates) or the tocotrienols (or their acetates) should lead to longer sustained deliveries.

A study of the distribution of 2-ABA and 2-HBA in the blood and synovial fluid (human knee) from ingested 650 mg doses of 2-ABA showed the maximum plasma levels of 3.3 µg/ml 2-ABA in 7.7 minutes and 23 µg/ml 2-HBA in 10.9 minutes. Maximum synovial fluid levels were 2.5 µg/ml 2-ABA in 19.4 minutes and 14.5 µg/ml 2-HBA in 21.9 minutes. Soren, 6(1) Scand J Rheumatol 17-22 (1977). The 2-ABA was gone in the blood in 75 minutes and gone in the synovial fluid in 2.3 to 2.4 hours. A study of intra-articular injections of 20 µg/ml 2-ABA in the 33 ml of synovial fluid in the adult human knee also revealed that the average half life of combined 2-ABA/2-HBA was 2.4 hours. Owen et al., 38 Brit. J. Clin. Pharma. 347-55 (1994); Wallis et al., 28 Arthritis Rheum 441-49 (1985).

In addition to the references noted above relating to anti-inflammation therapies involving topical applications of 2-ABA ester formulations, there are the references referring to 2-ABA esters (U.S. Pat. No. 3,119,739, U.S. Patent Application Pub. No. 2002-0013300) or 2-ABA (U.S. Pat. No. 4,126,681) as analgesics for skin irritations and wound healing. Other reports, however, reveal poor results with topically applied 2-ABA to relieve pain from insect bites (Balit et al., 41(6) Toxicol Clin Toxicol 801-08 (2003)) or allergic reactions (Thomsen et al., 82 Acta Derm Venereal 30-35 (2002)). Better results were found on dermal applications of chloroform solutions of 2-ABA (Kochar et al., 47(4) J Assoc Physicians India 337-40 (1999)) or slurries of 2-ABA in a commercial skin moisturizer (Balakrishnan et al., 40(8) Int J Dermatol 535-38 (2002)) to alleviate the pain of acute herpetic neuralgia. It is important to note that most of these reported formulations contained water. Thus, unless these formulations were used immediately after their preparation it is very likely significant hydrolysis of the 2-ABAs or their esters removed the acetyl group to give the less potent 2-HBA derivatives. There is the need for non-aqueous or non-alcoholic penetrating excipients in topical 2-ABA and 2-ABA ester formulations for useful shelf life.

Hence, in an embodiment of the invention the components used in the formulations are selected from the following two groups:

Group I: 2-acetyloxy benzoic acid, methyl 2-acetyloxy benzoate, ethyl 2-acetyloxy benzoate, n-propyl 2-actyloxy benzoate, isopropyl 2-acetyloxy benzoate, n-butyl 2-acetyloxy benzoate, isobutyl 2-acetyloxy benzoate.

Group II: d, l and dl isomers of alpha, beta, gamma and delta tocopherols and their acetate esters; d, l and dl isomers of alpha, beta, gamma, and delta cotrienols and their acetate esters; all along with licorice extracts or deglycyrrhized licorice extracts.

Thus, one aspect of this invention involves novel mixtures of compounds selected from group I with compounds selected from group II to give formulations for oral administration having essentially all the beneficial therapeutic properties of 2-ABA but with much less to none of the gastric stress associated with 2-ABA. These novel formulations for ingestion have the general compositions of 350 pts/wt 2-ABA or 400 to 500 pts/wt of 2-ABA esters mixed with 40 to 400 pts/wt tocopherols or their acetates plus 35 to 110 pts/wt tocotrienols or their acetates plus 400 to 1400 pts/wt licorice extract or degglycerrhized licorice extract. A convenient source containing mixture of tocopherols and tocotrienols is either palm seed oil extract (Carotech Inc. among many suppliers) or rice bran oil extract (Eastman Chemicals, among many other suppliers). There is some evidence that the palm seed source is preferred because it has a higher delta tocotrienol content. Theriault et al., 32(5) Clin Biochem 309-19 (1999); Yap et al., 53(1) J Pharm Pharmacol 67-71 (2001).

An example, but non-limiting, formulation would be: 350 mg 2-ABA (or 400 mg ethyl 2-ABA); 200 mg tocopherol/ tocotrienol (palm seed oil extract); and 125 mg licorice extract. Such a formulation might be conveniently contained in a gel capsule with one to eight capsules/day being ingested as needed to alleviate inflammatory conditions throughout the human or animal body.

Another aspect of this invention involves novel sustained release mixtures of 2-ABA or 2-ABA esters with tocopherol or tocopherol acetate for intra-ocular or intra-articular injections as therapies for inflammatory conditions of the eye or joints of animals or humans. The general range of amounts of these components in the formulations is 5 to 95 pts/wt 2-ABA esters or micronized 2-ABA and 95 pts/wt to 5 pts/wt tocopherol or its acetate. An example, but non-limiting, formulation is 250 pts/wt ethyl 2-ABA or micronized 2-ABA; 400 pts/wt α-dl or d-tocopherol acetate. This formulation is amenable to injection through 20 gauge to 30 gauge needles in 10 mg to 100 mg aliquots into the vitreous chamber of the eye to provide sustained release of therapeutic levels of 2-ABA or its ester for periods of ten days to one year. Similarly, 10 mg to 3000 mg of these formulations may be injected into the synovial chambers of human or animal joints to provide anti-inflammatory therapy for periods of ten days to one year.

A further aspect of this invention involves novel formulations of 5 pts/wt to 95 pts/wt 2-ABA or its esters with 95 pts/wt to 5 pts/wt tocopherols, tocopherol acetates and/or tocotrienols, tocotrienol acetates for the topical applications to penetrate the skin of humans or animals to alleviate inflammation and pain in the skin or joints. Again, a convenient source of both the tocopherols and tocotrienols would be palm seed oil or rice bran oil extracts. A specific non-limiting formulation would be: 60 pts/wt ethyl 2-ABA or micronized 2-ABA; 40 pts/wt palm seed oil extract.

Another aspect of the present invention provides formulations useful in treating brain tumors. The incidence of brain tumors is continuing to increase and becomes more marked as the population ages. Thus, for example the average incidence is 1.8/100,000 people 15-24 years of age but about 18.4/100,000 of those 65-79 years of age. The age peak is between 55 and 73 years, although increasing numbers of young patients with glioblastomas have been recorded in recent years. The estimated number of people living in the US with a diagnosis of primary brain and central nervous system tumor is about 360,000. The annual incidence of a primary brain tumor in the U.S. is about 18,500 people, of whom most die within the first year after discovery. Despite surgery, irradiation, or present chemotherapy regimens, patients survive on average for only eleven months. The tumors, by then, become large enough to crush vital portions of the brain.

The tumors which occur most commonly originate from astrocytes, ependymocytes and oligodendrocytes. The prognosis of brain tumors is poor. Malignant gliomas account for 42% of all primary brain/CNS tumors, and of these in turn glioblastoma multiforme (GBM) and anaplastic astrocytoma, which together account for about 80% of all malignant gliomas, and have the poorest prognosis. The GBM is the subject of much research because it is the most common and potentially destructive brain tumor. While many tumors contain a mixture of cell types, GBM is the most mixed of brain tumors. It is this characteristic that makes it difficult to treat. While one cell type may be responsive to a treatment and dies, other types are waiting to take over. Additionally, often only partial tumor resection is possible, leaving remaining and dislodged cancer cells that can stray throughout the brain. The histologic distribution of primary brain and CNS gliomas is: glioblastoma 50.5%, ogliodendrogliomas 9.5%, ependymomas 4.9%, all other gliomas 9.7%, anaplastic astrocytomas 8.2%, pilocytic astrocytomas 4.7%, diffuse astrocytomas 1.8%, all other astrocytomas 9.3%.

The currently available nonsurgical therapeutic options, irradiation and systemic chemotherapy, are all associated with adverse reactions, some of which are severe, which represent limiting factors for an increasingly aging population afflicted with other multiple pathologies. The main problem is the fact that recurrence of these tumors is unavoidable even with, or despite, the use of present day aggressive surgical, radiation, and chemotherapy regimens.

Surgical removal of a tumor though resulting in initial relief of pressure seldom is able to capture all of the malignancy. It has been reported that the recurrence rate and increased growth rate is near 100% after resectioning in GMB patients. Recently it has been demonstrated experimentally using MRI imaging that there is an accelerated growth in brain tumor volume following incomplete surgical resectioning. It is very likely that tissue injury promotes cancer growth by altering the micro-environment and provides a more permissive field for tumor expansion and invasion. Local outpouring of inflammatory cytokines and vascular endothelial growth factors are likely contributors to this environment. In addition to this acceleration of the proliferation of the remaining malignant tissue there is often significant collateral damage to healthy tissue, troublesome bleeding and edema.

Irradiation procedures also lead to considerable collateral damage. In addition to initial edema there are delayed reactions over weeks to months manifested by neuropsycho-logical disorders, dementia, and/or atrophy of the cerebral cortex among others.

The chemical therapeutic regimens which with few exceptions involve systemic administrations with their collateral damage to other areas of the body, also must contend with the blood-brain barrier to penetration of the drug to the desired site. In principle then, primary brain tumors are categorized as tumors for which even now there are no effective, curative therapeutic approaches.

The novel biocompatible, biodegradable sustained release formulations revealed in the present invention are either syringeable liquids, mechanically cohesive solids, injectable gels, or emulsified micells (oil in water or water in oil). A desirable feature of these liquid, solid and gel formulations is that they maintain a single bolus or pellet shape at the site of their placement. That is, they do not break up as a multitude of smaller droplets or particles that migrate away from their intended point of placement and/or by virtue of a resultant increase in surface area greatly alter the intended release rate of their drug content.

The present invention relates generally, but not totally, to the use of compounds that are syringible, of limited solubility, biocompatible and biodegradable for controlled and sustained release of an agent or a combination of agents. Solid, gel, or injectable controlled-sustained release systems can be fabricated by combining an excipient from the list above and a beneficial agent. Systems can combine more than one of these excipients as well as more than one beneficial agent. Solid forms for implantation can be produced by tableting, injection molding or by extrusion. Gel can be produced by vortex or mechanical mixing. Injectable formulations can be made by pre-mixing in a syringe or mixing of the excipient and the beneficial agent at the time of administration.

Solid form generally contains 1-60% of one or more of the excipients, 20-80% for a gel and 50-99% for a liquid. The content of the therapeutic agent/agents can range from 10% to 90% of the formulation. The amount of these excipient/therapeutic agent formulations placed in the tumor can range from about 2 to 20 µl or µg per ml of tumor volume. The sustained release of the therapeutic agent/agents into the tumor can be controlled to last from several days to several years. In a timely fashion the total formulation disappears from the site with little or no after effects.

Solid, liquid or gel excipient/agent formulations can be implanted surgically or implanted by trocar or needle introduction directly into the brain tumor such as inoperable gliomas [typically using a procedure similar to that described by Emerich et al., 17(7) Pharm. Res. 776-78 (2000). For localized beneficial agent delivery, the systems of the present invention may also be surgically implanted in or near the site of the tumor or the cavity left from tumor resection. An especially attractive procedure is contemplated which involves the phacoemulsion techniques commonly used in cataract surgery. In this contemplated procedure the phacoemulsion device adapted for intracranial operation is inserted into the tumor and a portion of the tumor tissue is emulsified for facile removal by irrigation. At this time a sustained release formulation might be administered for immediate therapy (possibly a steroidal anti-inflammatory for example). Removal of portions of tumor tissue allows temporary relief of pressure, and the removed tissue can be assayed to identify cell types. Knowledge of the cell types permits the selection of the best long term therapeutic agent or agents for the subsequent injectable sustained release formulations to eradicate the tumor mass.

More specifically, an embodiment of the present invention provides for a biocompatible, biodegradable, syringeable liquid, implantable solid, and indictable gel sustained release formulations of therapeutic agents for brain tumors that may be inserted directly into brain tumors. These formulations comprise novel biocompatible and biodegradable syringeable liquid, implantable cohesive solids and injectable gel formulations conveniently placed inside brain tumors for the sustained release of beneficial agents are obtained by admixing one or more of the excipients: benzyl benzoate, esters of benzoic acid with straight, branched, or cyclic chain aliphatic alcohols having one to twenty carbon atoms wherein one of the hydrogen atoms on the aliphatic chain is replaced with a hydroxyl group (e.g., such alcohols as methanol, ethanol, n-propanol, i-propanol, n-butanol, i-butanol, s-butanol, t-butanol, n-pentanol, i-pentanol, neo-pentanol, n-hexanol, cyclohexanol, n-heptanol, n-octonol, n-nonanol, n-decanol, and the like), mono, di and tri esters of O-acetylcitric acid, or O-proionylcitric acid, or O-butyrylcitric acid with $C_1$ to $C_{10}$ straight and branched chain aliphatic alcohols, mono, di, and tri easters of citric acid with $C_1$ to $C_{10}$ straight and branched chain aliphatic alcohols, diethylene glycol dibenzoate, triethylene glycol dibenzoate, dibenzoate esters of poly(oxyethylene)diols up to about 400 mwt, propylene glycol dibenzoate, dipropylene glycol dibenzoate, tripropylene glycol dibenzoate, dibenzoate esters of poly(oxypropylene)diols up to about 3000 mwt, poly(oxypropylene)diols up to about 3000 mwt, dimethyl sulfone, and the various isomers of tocopherol, tocopherol acetate, tocopherol succinate, and tocopherol nicotinate; and the various isomers of the tocotrienols and their acetates, succinates and nicotinates, polymeric polycarbonate oligomers; polymers and copolymers of glycolic and lactic acids, with a large number of established and new agents for the treatment of brain tumors.

Such agents include tetrahydrocortisol; 4,9(11)-pregnadien-17α,21-diol-3,20-dione (Anecortave acetate, Retaane, Alcon, Inc.); 4,9(11)-pregnadien-17α,21-diol-3,20-dione-21-acetate; 11-epicortisol; 17α-hydroxyprogesterone; tetrahydrocortexolone; cortisone; cortisone acetate; hydrocortisone; hydrocortisone acetate; fludrocortisones; fludrocortisone acetate; fludrocortisone phosphate; prednisone; prednisolone; prednisolone sodium phosphate; methylprednisolone; methylprednisolone acetate; mehtylprednisolone sodium succinate; triamcinolone; triamcinolone-16,21-diacetate; triamcinolone acetonide; triamcinolone acetonide-21-acetate; triamcinolone acetonide-21-disodium phosphate; triamcinolone acetonide-21-hemisuccinate; triamcinolone benetonide; triamcinolone hexacetonide; fluocinolone; fluocinolone acetate; fluocinolone acetonide; dexamethasone; dexamethasone-21-acetate; dexamethasone-21-(3,3-dimethylbutyrate); dexamethasone-21-phosphate disodium salt; dexamethasone-21-diethylaminoacetate; dexamethasone-21-isonicotinate; dexamethasone-21-dipropionate; dexamethasone-21-palmitate; betamethasone; betamethasone-21-acetate; betamethasone-21-adamantoate; betamethasone-17-benzoate; betamethasone-17,21-dipropionate; betamethasone-17-valerate; betamethasone-21-phosphate disodium salt; beclomethasone; beclomethasone dipropionate; diflorasone; diflorasone diacetate; mometasone furoate; acetazolamide (Diamox); naproxen; naproxin sodium salt; diclofenac; diclofenac sodium salt; celecoxib; rofecoxib; valdecoxib; etoricocib; lumiracoxib; sulindac; sulindac sodium salt; diflunisal; diflunisal sodium salt; piroxicam; indomethacin; indomethacin sodium salt; etodolac; etodolac sodium salt; meloxicam; ibuprofen; ibuprofen sodium salt; ketoprofen; ketoprofen sodium salt; r-flurbiprofen (Myriad Genetics, Inc.); mefenamic; mefenamic sodium salt; nabumetone; tolmetin; tolmetin sodium salt; ketorolac bromethamine; ketorolac tromethamine (Todardol®, Sytex, SA); ketorolac acid; choline magnesium trisalicylate; aspirin; salicylic acid; salicylic acid sodium salt; salicylate esters of alpha, beta, gamma-tocopherols (and all their d, l, and racimic isomers); tenoxicam; aceclofenac; nimesulide; nepafenac; amfenac; bromfenac; flufenamate; phenylbutazone; CV 247 (Ivy Medical Chemicals plc); pegaptanib octasodium; ranibizumab (Lucentis®, Genentech, Inc.); 2-methoxyestradiol; shark cartilage extract (Neovastat, Aeterna); NX-278-L ant-VEGF aptamer (EyeTech); squalamine (MSI-1246, Genaera); 2'-O-methoxyethyl) antisense C-raf oncogene inhibitor (ISIS-13650); vitronectin and osteopontin antagonists (3-D Pharm.); combretstatin A-4 phosphate (CA4P, Oxigene); Fab fragment alpha-V/beta-1 integrin antagonist (Eos-200-F, Protein Design Labs); alpha-v/beta-3 integrin antagonist (Abbott); matrix metalloprotienase inhibitor (ISV-616, InSite Vision); matrix metalloprotienase inhibitor (TIMP-3, NIH); urokinase plasminogen activator fragment (A6, Angstrom Pharm.); vascular endothelial growth factor antagonist (AAV-PEDF, Chiron); kdr tyrosine kinase inhibitor (EG-3306, Ark Therapeutics); cytochalasin E (NIH); kallikrinin-binding protein (Med. Univ. of So. Carolina); combretastatin analog (MV-5-40, Tulane Univ.); pigment-epithelium derived growth factor (Med. Univ. So.Carolina); pigment-epithelium derived growth factor (AdPEDF, GenVec/Diacrin); plasminogen kringle (Med. Univ. So. Carolina); rapamycin; cytokine synthesis inhibitor/p38 mitogen-activated protein kinaseinhibitor (SB-220025, GlaxoSmithKline); vascular endothelial growth factor antagonist (SP-(V5.2)C, Supratek Pharm. Inc.); vascular endothelial growth factor antagonist (SU10944, Sugen/Pfizer); vascular endothelial growth factor antagonist (VEGF-R, Johnson & Johnson/Celltech); vascular endothelial growth factor antagonist (VEGF-TRAP, Regeneron); FGF1 receptor antagonist/tyrosine kinase inhibitor (Pfizer/Sugen); endostatin, vascular endothelial growth factor antagonist (EntreMed); bradykinin B1 receptor antagonist (B-9858, Cortech); bactericidal/permeability-increasing protein (BPI, Xoma); protein kinase C inhibitor (Hypericin, Kansai Med. Univ.); ruboxistaurinn mesylate (LY-333531, Eli Lilly); polysulphonic acid derivatives (Fuji Photo Film); growth factor antagonists (TBC-2653, TBC-3685, Texas Biotechnology); Tunica internal endothelial cell kinase (Amgen); acetylcysteine; mannitol; antineoplaston; human corticotropin-releasing factor; VN40101M (Pediatric Brain Tumor Consortium); everolimus; GW572016 (NCI); thalidomide; temozolomide; tariquidar; doxorubicin; dalteparin; tarceva; CC-5013 (NCI); hCRF (Xerecept, Neurobiological Technologies); bevacizumab (Avastin, Genentech); melphalan; thiotepa; depsipeptide; erlotinib; tamoxifen; bortezomib; lenalidomide; vorinostat; temsirolimus; modifinil; enzastuarin; motexafin gadolinium; F-18-OMFD-PET (Advanced Biochemical Compounds, Redeberg); pemetrexed disodium; ZD6474 (NCI); valproic acid; vincristine; irinotecan; PEG-interferon alpha-2b; procarbazine; lonafarnib; arsenic trioxide; GP96 (Univ. Cal. S.F.); carboplatin; cyclophosphamide; 1311-TM-601 (Trans Molecular); lapatinib; O6-benzylguanine; TP-38 toxin (NCI); cilengitide; poly-ICLC (NCI); FR901228 (NCI); TransMid™ (Xenova); talabostat; ixabepilone; AEE788 (Jonson Comprehensive Cancer Center); sirolimus; alanosine; sorafenib; efaproxiral; carmustine; iodine I 131 monoclonal antibody TNT-1/B (NCI); intratumoral TransMid™; topatecan; lomustine; phosphorus 32; 18F-fluorodeoxyglucose (Alberta Cancer Board); vinblastine; BMS-247550 (NCI); CC-8490 (NCI); IL 13-PE38QQR (Neopharm); imatib mesylate; hydroxyurea; G207 (MediGene); radiolabeled monoclonal antibody; 2-deoxyglucose; talampanel; retinoic acid; gefitinib; tipifarnib; CPT-11 (Kentuckiana Cancer Inst); rituximab; efaproxiral; PS-341 (FDA Office Orphan Product Development); capecitabine; G-CFS (NCI); vinorelbine; DCVax®-Brain (Northwest Biotherapeutics); paclitaxel; patipilone (Norvartis); iressa; methotrexate; ABT-751 (NCI); oxaliplatin; MS-275 (NCI); trastuzumab; pertuzumab; PS-341 (NCI); 17AAG (NCI); lenalidomide; campath-1H; somatostatin analog; resveratrol; CEP-7055 (Cephalon); CEP-5214 (Cephalon); PTC-299 (PTC Therapeutics); inhibitors of hepatocyte growth factor (L2G7mAb, Galaxy Biotech); statins such as atorvastatin (Lipitor®, Pfizer), fluvastatin (Lescor®, Novartis), rosuvastatin (Crestor®, Astra Zeneca), prevastatin (Provacol®, Teva Pharm.), simvastatin Zocar®, Merck & Co., Inc.), lovastatin (Mevorcor®, Merck) or cervastatin (Baycol®, Bayer AG) (HMG-CoA reductase inhibitors); and Receptor tyrosine kinase inhibitors.

Such agents also include Anti-neovascularization steroids such as 21-nor-5β-pregnan-3α,17α,20-triol-3-acetate; 21-nor-5α-pregnan-3α,17α,20-triol-3-phosphate; 21-nor-5β-pregn-17(20)en-3α,16-diol; 21-nor-5β-pregnan-3α,17β, 20-triol; 20-acetamide-21-nor-5β-pregnan-3α,17α-diol-3-acetate; 3β acetamido-5β-pregnan-11β,17α,21-triol-20-one-21-acetate; 21-nor-5α-pregnan-3α,17β,20-triol; 21α-methyl-5β-pregnan-3α,11β,17α,21-tetrol-20-one-21-methyl ether; 20-azido-21-nor-5β-pregnan-3α,17α-diol; 20(carbethoxymethyl)thio-21-nor-5β-pregnan-3α,17α-diol; 20-(4-fluorophenyl)thio-21-nor-5β-pregnan-3α,17α-diol; 16α-(2-hydroxyethyl)-17β-methyl-5β-androstan-3α,17α diol; 20-cyano-21-nor-5β-pregnan-3α,17α-diol; 17α-methyl-5β-androstan-3α,17β-diol; 21-nor-5β-pregn-17(20)en-3α-ol; 21- or -5β-pregn-17(20)en-3α-ol-3-acetate; 21-nor-5-pregn-17(20)-en-3α-ol-16-acetic acid 3-acetate; 3β-azido-5β-pregnan-11β,17α,21-triol-20-one-21-acetate; and 5β-pregnan-11β,17α,21-triol-20-one; 4-androsten-3-one-17β-carboxylic acid; 17α-ethynyl-5(10)-estren-17β-ol-3-one; and 17α-ethynyl-1,3,5(10)-estratrien-3,17β-diol.

Another aspect of the present invention provides for embodiments comprising omega-3 fatty acids. The health benefits of dietary supplements of omega-3 fatty acids and their esters are well known. The particularly important omega-3 fatty acids in human nutrition are α-linolenic acid (ALA, C18H30O2, fw 278.4) eicosapentaenioc acid (EPA, C20H30O2, fw 306.5) and docosahexaenoic acid (DHA, C22H32O2, fw 328.5). The term omega-3 signifies that the first double bond exists between the third and second carbon atoms counting from the terminal methyl at the opposite end of the chain from the carbonyl group.

The human body cannot synthesize EPA or DHA except by using ALA as an intermediate. But the presence of EPA and DHA in almost all tissues of the body indicates the importance of these compounds to the body and thus the judicious injection into the body of their therapeutic formulations will be safe, efficient and effective. These benefits also extend to the simple esters of EPA and DHA of the $C_1$ to $C_8$ straight and branched chain aliphatic alcohols such as ethyl EPA and ethyl DHA. Recently, the FDA has approved ethyl EPA and ethyl DHA for dietary supplements. One important property of these ethyl esters is that they can be fractionally distilled from their readily available but crude source, fish oil. This purification process provides the EPA and DHA esters free from possible heavy metal and PCB contaminants. Thus, there remains a need for the development of these purified esters as liquid excipient vehicles for injectable sustained drug release in various areas of the human or animal body.

The embodiments thus provide for the novel concept of injections of omega-3 fatty acids and their esters by themselves or as novel and therapeutic formulations with active agents directly into strategic areas of the human or animal bodies to provide for the sustained release of the omega-3 compounds and therapeutic but nontoxic levels of the active agents for periods of months to over a year.

Yet another embodiment of the present invention relates generally to novel injectable and topically applied formulations containing both steroids and antioxidants. Specifically, the inclusion of antioxidants with steroids addresses the problem that many steroids have harmful side effects arising from their being initiators of destructive oxidative and photo-oxidative radical chain reactions. These novel steroid-antioxidant formulations are designed to be injected into the eye, joints, organs, or to be applied topically externally for the known steroid therapies of anti-inflammation and regulation of metabolic and immune functions, but also due to the presence of antioxidants to suppress damaging oxidative free radical reactions initiated by the steroids in addition to harmful oxidative chemistries normally present in cells.

Although oxygen is required for many life sustaining metabolic reactions it also has damaging chemistries with cellular components. These harmful chemistries involve the very reactive oxygen components: superoxide radicals, hydrogen peroxide, hydroxyl radicals, and organic peroxides and hydroperoxides. Polyunsaturated lipids are important components of cells, but they are major substrates for oxidative attack leading to cell death. Thus, the dependence of cells on oxygen places them a precarious position between the prolife and toxic chemistries of oxygen. To tip the delicate balance towards life, nature provides cells with protective antioxidant molecules such as tocopherol, ascorbic acid, glutathione, melatonin, carotenes, carnitine and others. The natural level of tocopherol in the human lens is around 2.2 µg/ml (Yeum et al., 19(6) Curr. Eye Res. 502-05 (1999)), and the ascorbate level in tears is 3.52 µg/ml (Choy et al., 80(9) Optom. Vis. Sci. 632-36 (2003)). Unfortunately the exposure of cells to some steroids, even though for very necessary therapeutic reasons, has been found to tip this balance towards the toxic side. For it has been demonstrated that these steroids, especially the glucocorticosteroids such as triamcinolone and dexamethasone, readily interact with oxygen and/or light to become initiators of damaging oxidative chain reactions. Miolo et al., 78(5) Photochemistry & Photobiology, 425-30 (2003); Calza et al., 12(12) J. Am. Soc. Mass. Spectrom., 1286-95 (2001). Although the co-administration of certain antioxidants with certain steroids has been shown to ameliorate the toxic oxidative processes initiated by the steroids (Kosano et al., 76(6) Exp. Eye Res., 643-48 (2001) and references therein), presently most commercial injectable steroid formulations do not include antioxidants. See Fact sheet inserts for Kenalog™, Bristol-Myers Squibb, 2006; Depo Medrol™, Pharmacia, 2003; Decadron™, Merck Sharp & Dohme, 1995, (contains bisulfites, hydroxybenzoate esters which might have antioxidant effects). In formulating compositions containing antioxidant supplements one must be very careful not to add too high a level of antioxidants, however, because it has been demonstrated that at high levels many of these antioxidants actually are pro-oxidants and may increase oxidative damage. Bowry et al., 270 J. Biol. Chem. 5756-63 (1995); Halliwell, 25 Free Rad. Res. 439-54 (1996). Using the naturally occurring antioxidants and mimicking their levels in the cell environment would be good practice.

The areas of therapy of particular interest for applying the formulations of this invention involve intraocular injections (for the indications: cystoid macular edema, exudative age-related macular degeneration, proliferative diabetic retinopathy, diabetic macular edema, choroidal neovascularization, retinal vein occlusion, uveitis); intra-articular injections (for the indications: synovitis of osteoarthritis, rheumatoid arthritis, bursitis, gouty arthritis, epicondylitis, nonspecific tenosynovitis, post-traumatic osteoarthritis); and topical applications on the body exterior. The steroid components and excipients of these novel formulations and their therapeutic effects are well described herein and in U.S. Patent Application Publication No. 2006/0073182. The possible adverse effects of the steroids used in these formulations are in many cases believed to arise from the aforementioned damaging oxidative chemistries initiated by these steroids in the absence of proper antioxidants. The environment of the eye is particularly damaging for it is exposed to both oxygen and light energy. The phenolic or quinone-like structures of the steroid molecules readily absorb UV-A and UV-B radiation to convert these molecules to unpaired electron radical species. These radical species can damage cell components (especially unsaturated lipids in cell membranes) or they can interact with oxygen to instigate damaging peroxy chain reactions leading to cataracts (Nishigori et al., 35(9) Life Sci. 981-85 (1984); Boscia et al., 41(9) Invest. Ophthalmol. Vis. Sci. 2461-65 (2000)), and glaucoma (Sacca et al., 84(3) Exp. Eye Res. 389-99 (2007)). Cataract formation and glaucoma are maladies associated with steroid therapies in the eye. In the case of intra-articular steroid therapies repeated injections are avoided because they lead to cartilage and bone degeneration. Reactive oxygen species have been identified as causative agents. Kim et al., 49(9) Free Radic. Biol. Med. 1483-93 (2006).

Without further elaboration, one skilled in the art having the benefit of the preceding description can utilize the present invention to the fullest extent. The following examples are illustrative only and do not limit the remainder of the disclosure in any way.

EXAMPLES

Example 1

Preparation of a Poly(1,3-propanediol carbonate) I from 1,3-propanediol at 65° C. and 96 Hours To 23.6 g (0.2 mole) diethyl carbonate (b.p. 128° C.) was added 15.2 g (0.2 mole) 1,3-propanediol containing 0.05 g (1.25 mmole) of metallic Na to give two liquid phases. These reactants were placed in an open container in a 65° C. oven and were shaken occasionally. After 12 hours, the reactants were a homogeneous solution weighing 38.0 g. The theoretical weight for the loss of 0.4 moles (18.4 g) of ethanol in a complete reaction would be 20.4 g. The heating and occasional shaking were continued to give 27.0 g at 24 hours, 23.2 g at 48 hours, 21.4 g at 72 hours, and 17.4 g at 96 hours. The product oil was washed with 15 ml 5% aqueous acetic acid to two phases. The top phase was the water soluble phase. The 10.5 ml bottom phase was washed with 15 ml water to give 7.5 ml of a poly(1,3-propylene glycol carbonate) oligomer as a water-insoluble oil.

Example 2

Preparation of Poly(1,3-propanediol carbonate) II from 1,3-propanediol at 110-150° C. and 26 Hours A mixture of 76 g (1.0 mole) 1,3-propanediol containing 0.1 g metallic Na (2.5 mmole) and 118 g (1.0 mole) diethyl carbonate was heated at 110° C. As soon as the reactants reached 60° C. they formed a homogeneous solution. After heating 8 hours, the reactants had lost 48 g (52% of theoretical amount of ethanol). The temperature was then raised to 150° C. After 10 hours, the reactants lost another 46 g. A drop of this product completely dissolved in water. The resultant 97 g of oil was mixed with 6 g (0.05 moles) diethyl carbonate and the resultant solution was heated with occasional stiffing at 150° C.

After 8 hours, the resultant syrup was found to be partially insoluble in water. The product was washed with 100 ml 5% aqueous acetic acid followed by four washings with 100 ml portions of water to give 46.1 g slightly yellow viscous oil (46.1/102=45% yield).

Example 3

Preparation of a Poly(di-1,2-propylene glycol carbonate) from di-1,2-propylene glycol To 59.0 g (0.5 moles) diethyl carbonate was added 67.0 g (0.5 moles) di-1,2-propylene glycol which had been reacted with 0.02 g Na to form a homogeneous solution. The reactants were placed in an open flask at 100° C. After 12 hours, the solution lost 23.4 g (about 50% of the theoretical 46 g ethanol). After another 15 hours at 150° C. the reactants had lost a total of 53.2 g to give a syrup that was partially insoluble in water. The product was washed with 100 ml 5% aqueous acetic acid followed by four washing with 100 ml portions of water to give 25.2 g colorless viscous, water insoluble liquid poly(di-1,2-propylene glycol carbonate) oligomer.

Example 4

Preparation of a Poly(tri-1,2-propylene glycol carbonate) from tri-1,2-propylene glycol To 0.1 g Na metal was added t 96.0 g (0.5 mole) tri-1,2-propylene glycol. After 5 minutes, the Na had reacted leaving a light yellow oil. 59.0 g (0.5 mole) diethyl carbonate was added to this liquid and the resultant homogeneous solution was heated to 110° C. in an open flask. After 6 hours, the reactants lost 28.0 g (61% of theory). The yellow solution was then heated at 125° C. for 8 hours, whereupon the reactants had lost a total of 48 g (104% of theory). Another 6.0 g (0.5 moles) diethyl carbonate were added and the temperature was raised to 150° C. After 6 hours, the viscous yellow-brown product solution was washed with 100 ml 5% aqueous acetic acid followed by 4 washings with 100 ml portions of water to give 48 g of a viscous orange, water insoluble liquid oligomer.

Example 5

The Assay Procedure for Measuring the Release Profiles of dexamethasone or triamcinolone acetonide from their Sustained Release Formulations (SRF)

The vials for the release studies were labeled and the weight of each vial was recorded. To each vial was added 3-4 grams of 0.9% saline solution and the weight was recorded. Then the SRF was injected or placed at the bottom of the vial. The weight of the SRF was recorded. An additional amount of 0.9% saline solution was added to a total of 10 grams of saline. The resulting vial was kept in an incubator or water bath at 37° C. Samples were taken periodically to measure the release profile of dexamethasone or triamcinolone acetonide using a HPLC instrument. Sampling protocol was carried out according to the following procedure: Using a disposable pipette, 8 grams of the saline solution containing dexamethasone or triamcinolone acetonide was withdrawn carefully from each vial. 8 grams of 0.9% saline solution was then added to each vial. The vials were kept at 37° C. after sampling.

The HPLC analysis was carried out using a Beckman Gold Instrument with an autosampler. Calibrators with three different concentrations of dexamethasone or triamcinolone acetonide in water were prepared. Calibrators and samples were injected onto a C18 column (Rainin, 250×4.6 mm) containing a guard column (C18, 4.6 mm×1 cm) and analyzed, respectively. The column was eluted using a mobile phase of 45% (or 50%) acetonitrile/water, flow rate 1.0 mL/min, and 7 (or 6) minute run time at an ambient temperature. The detector wavelength of 238 nm was used. The dexamethasone or triamcinolone acetonide (retention times, 6-4 minutes) concentration of each sample was calculated from the standard curve using the software of the Beckman Gold instrument.

A wash program to clean the HPLC column was set up during the HPLC run. After every three or four injections, a sample containing 20 µL of acetonitrile was injected onto the column, the column was eluted with a mobile phase of 99% acetonitrile/water, flow rate 1 mL/min, and a run time 7 minutes. Then the column was equilibrated back to the original mobile phase by injecting 20 µL of acetonitrile, eluting with 45% (or 50%) acetonitrile/water, flow rate 1 mL/min, and a run time 7 minutes.

The sampling times and the active ingredient (for example dexamethasone or triamcinolone acetonide) concentrations determined from HPLC were recorded and tabulated. The percent drug released and the amount of drug released were each calculated from a Microsoft Excel software program.

Example 6

Preparation of Mixtures of Dexamethasone in poly(1,3-propanediol carbonate) I and their Release Profiles Preparation of 10% dexamethasone in poly(1,3-propanediol carbonate) I: One portion by weight of dexamethasone was mixed with nine portions by weight of the poly(1,3-propanediol carbonate) I prepared in Example 1. The resulting suspension was stirred at an ambient temperature until a homogeneous mixture formed. The mixture was then aliquoted and analyzed for the release profile as shown in FIG. 1.

Preparation of 20% dexamethasone in poly(1,3-propanediol carbonate) I: Two portions by weight of dexamethasone were mixed with eight portions by weight of the poly(1,3-propanediol carbonate) I prepared in Example 1. The resulting suspension was stirred at an ambient temperature until a homogeneous mixture formed. The mixture was then aliquoted and analyzed for the release profile as shown in FIG. 1.

Example 7

Figure 2:
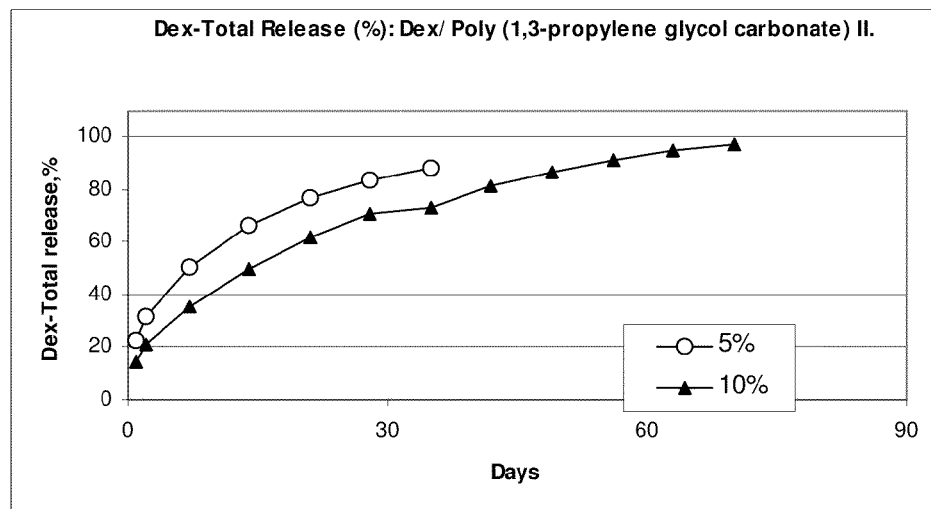
FIG. 2 presents dissolution profiles of Dex from two formulations of Dex/poly(1,3-propanediol carbonate)II.

Preparation of Mixtures of Dexamethasone in poly(1,3-propanediol carbonate) II and their Release Profiles Preparation of 5% dexamethasone in poly(1,3-propanediol carbonate) II: One portion by weight of dexamethasone was mixed with nineteen portions by weight of the poly(1,3-propanediol carbonate) II prepared in Example 2. The resulting suspension was stirred at an ambient temperature until a homogeneous mixture formed. The mixture was then aliquoted and analyzed for the release profile as shown in FIG. 2.

Preparation of 10% dexamethasone in poly(1,3-propanediol carbonate) II: One portion by weight of dexamethasone was mixed with nine portions by weight of the poly(1,3-propanediol carbonate) II prepared in Example 2. The resulting suspension was stirred at an ambient temperature until a homogeneous mixture formed. The mixture was then aliquoted and analyzed for the release profile as shown in FIG. 2.

Example 8

Figure 3:
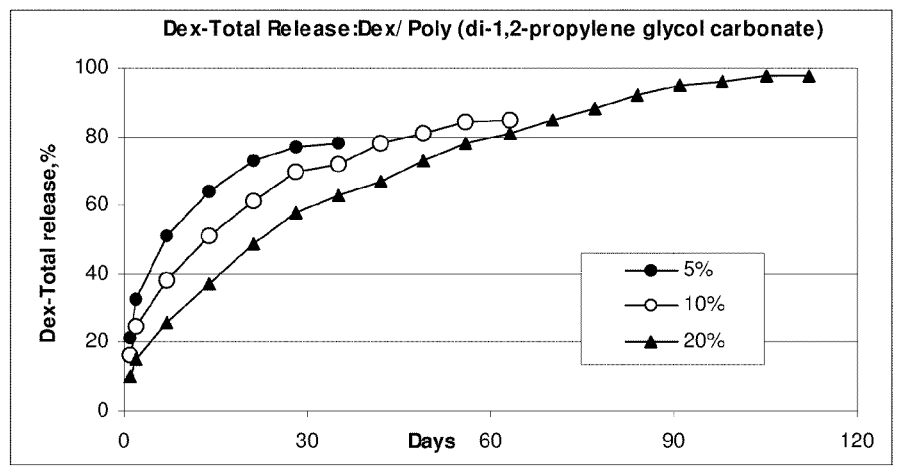
FIG. 3 represents dissolution profiles of Dex from three formulations of Dex/poly(di-1,2 propylene glycol carbonate).

Preparation of Mixtures of dexamethasone in poly(di-1,2-propylene glycol carbonate) and their Release Profiles Preparation of 5% dexamethasone in poly(di-1,2-propylene glycol carbonate): One portion by weight of dexamethasone was mixed with nineteen portions by weight of the poly(di-1,2-propylene glycol carbonate) prepared in Example 3. The resulting suspension was stirred at an ambient temperature until a homogeneous mixture formed. The mixture was then aliquoted and analyzed for the release profile as shown in FIG. 3.

Preparation of 10% dexamethasone in poly(di-1,2-propylene carbonate): One portion by weight of dexamethasone was mixed with nine portions by weight of the poly(di-1,2-propylene glycol carbonate) prepared in Example 3. The resulting suspension was stirred at an ambient temperature until a homogeneous mixture formed. The mixture was then aliquoted and analyzed for the release profile as shown in FIG. 3.

Preparation of 20% dexamethasone in poly(di-1,2-propylene glycol carbonate): Two portions by weight of dexamethasone were mixed with eight portions by weight of the poly(di-1,2-propylene glycol carbonate) prepared in Example 3. The resulting suspension was stirred at an ambient temperature until a homogeneous mixture formed. The mixture was then aliquoted and analyzed for the release profile as shown in FIG. 3.

Example 9

Figure 4:
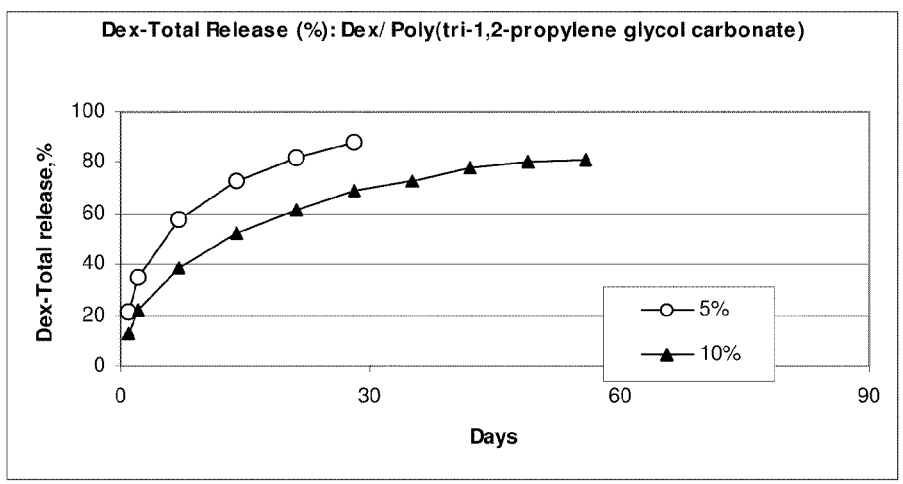
FIG. 4 depicts dissolution profiles of Dex from two formulations of Dex/poly(tri-1,2 propylene glycol carbonate).

Preparation of Mixtures of dexamethasone in poly(tri-1,2-propylene glycol carbonate) and their Release Profiles Preparation of 5% dexamethasone in poly(tri-1,2-propylene glycol carbonate): One portion by weight of dexamethasone was mixed with nineteen portions by weight of the poly(tri-1,2-propyleneglycol carbonate) prepared in Example 4. The resulting suspension was stirred at an ambient temperature until a homogeneous mixture formed. The mixture was then aliquoted and analyzed for the release profile as shown in FIG. 4.

Preparation of 10% dexamethasone in poly(tri-1,2-propylene glycol carbonate): One portion by weight of dexamethasone was mixed with nine portions by weight of the poly(tri-1,2-propylene glycol) carbonate prepared in Example 4. The resulting suspension was stirred at an ambient temperature until the formation of a homogeneous mixture. The mixture was then aliquoted and analyzed for release profile as shown in FIG. 4.

Example 10

Figure 5:
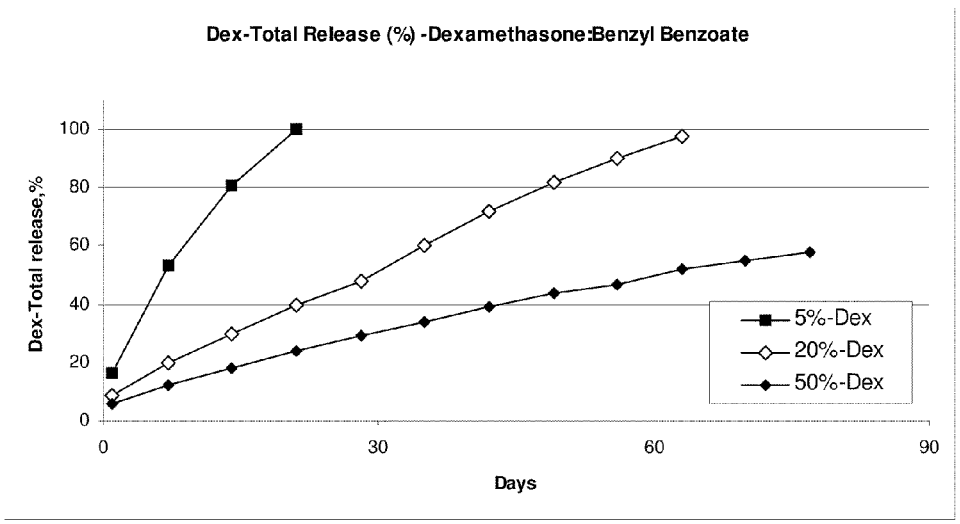
FIG. 5 depicts dissolution profiles of Dex released from three formulations of Dex/benzyl benzoate.

Preparation of Mixtures of dexamethasone in benzyl benzoate and their Release Profiles In preparing 20% dexamethasone in benzyl benzoate, two portions by weight of dexamthasone was mixed with eight portions by weight of benzyl benzoate. The resulting suspension was stirred at an ambient temperature until a homogeneous mixture formed. The mixture was then aliquoted and analyzed for the release profile as shown in FIG. 5.

Formulations containing 5% and 50% dexamethasone in benzyl benzoate were prepared under similar conditions to the 20% formulation, with the exception of the weight ratio of dexamethasone/benzyl benzoate. Mixtures of 5% and 50% dexamethasone in benzyl benzoate were prepared, and the resulting mixtures were aliquoted and small portions were analyzed for the release profiles as shown in FIG. 5.

Dexamethasone in benzyl benzoate forms a uniform suspension. A formulation of 25% is easily syringeable. As the suspension is slowly injected into the eye's posterior segment, a uniform spherical deposit (reservoir) is formed in the vitreous body. Dexamethasone is then released slowly into the vitreous humor of the posterior segment. Dexamethasone and benzyl benzoate are eventually metabolized to byproducts to be excreted in the urine.

Example 11

Figure 6:
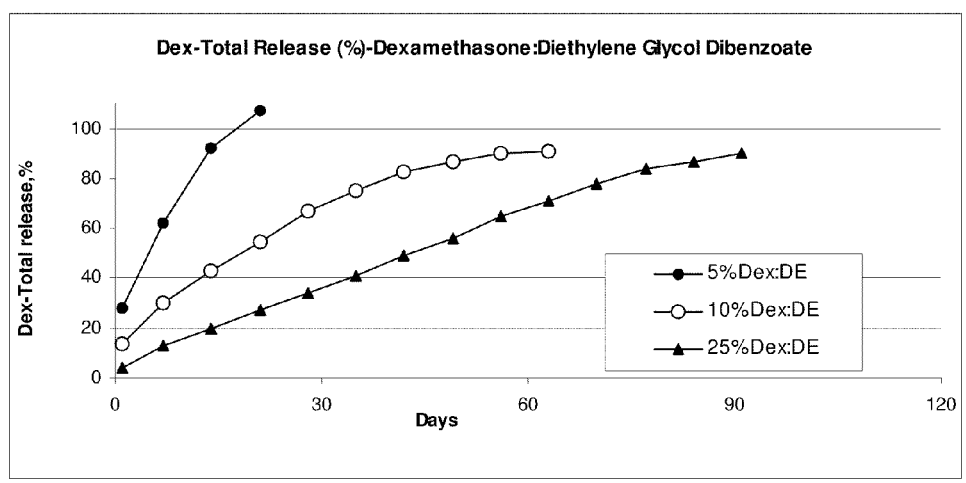
FIG. 6 depicts dissolution profiles of Dex released from three formulations of Dex/diethylene glycol dibenzoate.

Preparation of Mixtures of dexamethasone in diethylene glycol dibenzoate and their Release Profiles Ten percent dexamethasone in diethylene glycol dibenzoate was prepared by mixing one portion by weight of dexamethasone (Dex) with nine portions by weight of diethylene glycol dibenzoate. The resulting suspension was stirred at an ambient temperature until a homogeneous mixture formed. The mixture was then aliquoted and analyzed for the release profile as shown in FIG. 6.

Using conditions similar to that of the 10% Dex/diethylene glycol dibenzoate preparation, with the exception of the weight ratios, mixtures of 5% and 25% Dex/diethylene glycol dibenzoate formulations were prepared. The resulting mixtures were aliquoted and small portions analyzed for the release profiles as described previously. The resulting release profiles are shown in FIG. 6.

Example 12

Figure 7:
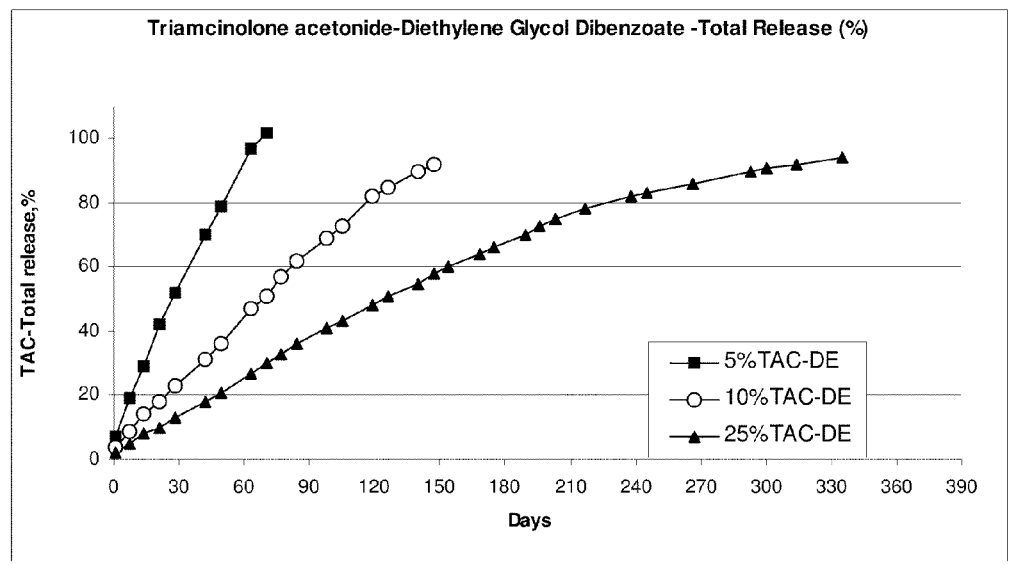
FIG. 7 depicts dissolution profiles of triamcinolone acetonide released from three formulations of triamcinolone acetonide/diethylene glycol dibenzoate.

Preparation of Mixtures of triamcinolone acetonide in diethylene glycol dibenzoate and their Release Profiles Preparations of 5%, 10% and 25% triamcinolone acetonide in diethylene glycol dibenzoate were prepared as follows: a 0.5, 1.0, or 2.5 portion by weight of triamcinolone acetonide was mixed with a 9.5, 9.0 or 7.5 portion by weight, respectively, of diethylene glycol dibenzoate. The resulting suspension was stirred at an ambient temperature until a homogeneous mixture formed. The mixture was then aliquoted and analyzed for the release profile as described previously. The resulting release profiles are shown in FIG. 7.

Example 13

Figure 8:
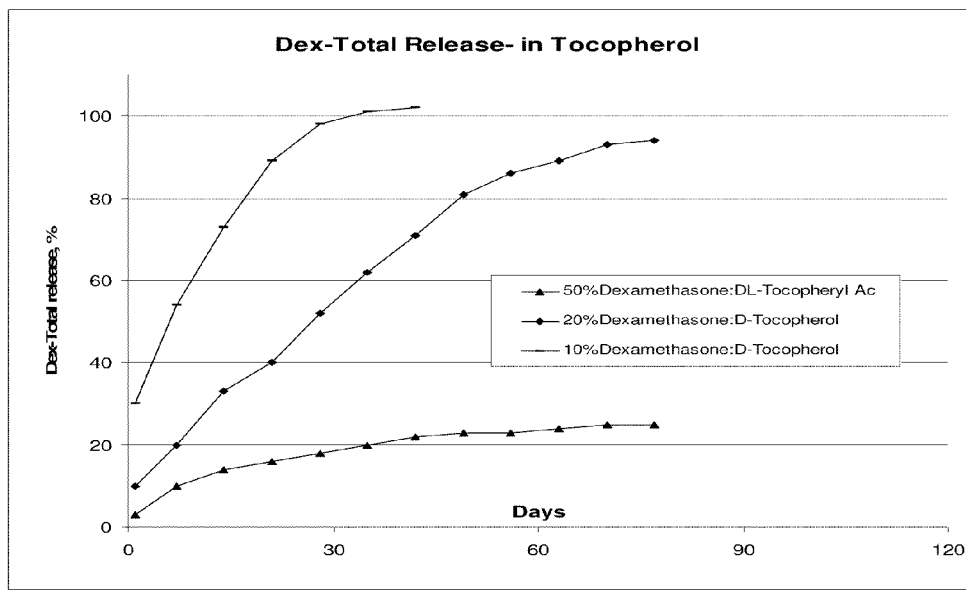
FIG. 8 depicts dissolution profiles of Dex released from three formulations of Dex/d-tocopherol, and dl-tocopheryl acetate.

Preparation of Mixtures of dexamethasone in d-tocopherol or d,l-tocopherol acetate and their Release Profiles For the preparation of 10% Dex in d-tocopherol, one portion by weight of Dex was mixed with nine portions by weight of d-tocopherol. The resulting suspension was stirred at an ambient temperature until a homologous mixture formed. The mixture was then aliquoted and analyzed for release profile as shown in FIG. 8.

For the preparation of 20% Dex in d-tocopherol, two portions by weight of Dex was mixed with eight portions by weight of d-tocopherol. The resulting suspension was stirred at an ambient temperature until the formation of a homologous mixture. The mixture was then aliquoted and analyzed for release profile as shown in FIG. 8.

For the preparation of 50% Dex in dl-tocopherol acetate, five portions by weight of Dex were mixed with five portions by weight of dl-tocopherol acetate. The resulting suspension was stirred at ambient temperature until a homologous mixture formed. The mixture was then aliquoted and analyzed for the release profile as shown in FIG. 8.

Example 14

Figure 9:
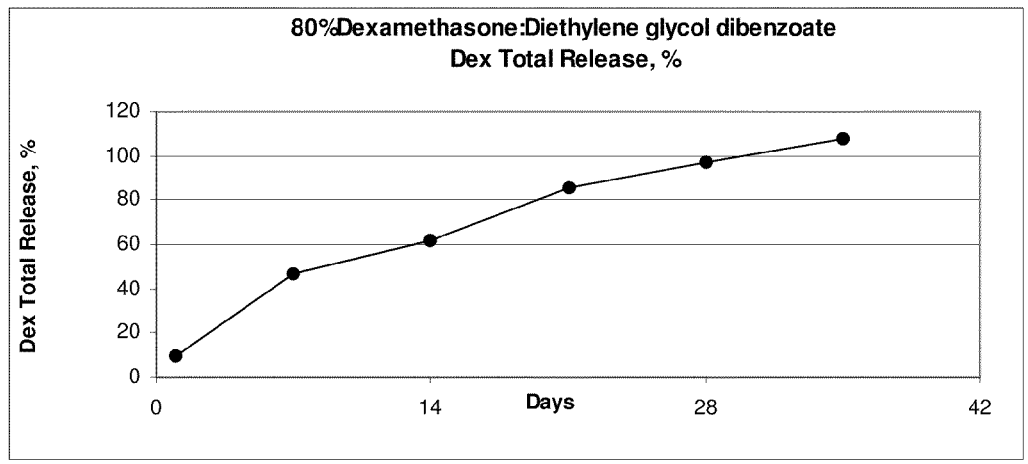
FIG. 9 depicts a dissolution profile of Dex released from a Dex/diethylene glycol dibenzoate formulation.

Manufacturing of a Solid Drug Delivery System with dexamethasone and diethylene glycol dibenzoate and its Release Profile Dexamethasone powder and diethylene glycol dibenzoate by weight were mixed thoroughly by mortar and pestle. The mixture was placed into a Parr pellet press of 2 mm diameter to form a solid pellet at 25° C. suitable for an implant. The newly formed pellet was then weighed in a microbalance before testing for in vitro kinetics as shown in FIG. 9.

Example 15

Figure 10:
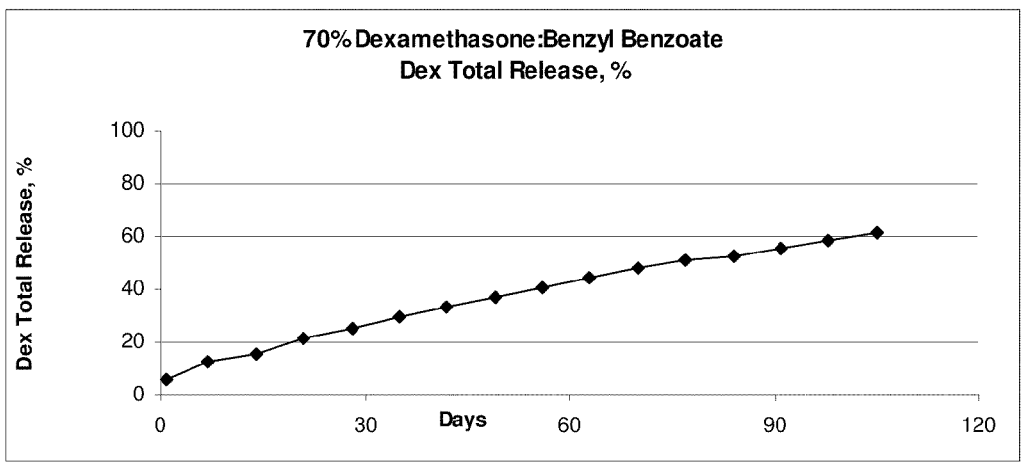
FIG. 10 depicts a dissolution profile of Dex released from a Dex/benzyl benzoate formulation.

Manufacturing of a Solid Drug Delivery System with dexamethasone and benzyl benzoate and its Release Profile Dexamethasone powder and benzyl benzoate by weight were mixed thoroughly by mortar and pestle. The mixture was then placed into a 2 mm diameter Parr pellet press to form a pellet at 25° C. suitable for an implant. The formed pellet was weighed and recorded in a microbalance before testing for in vitro kinetics as shown in FIG. 10.

Example 16

Figure 11:
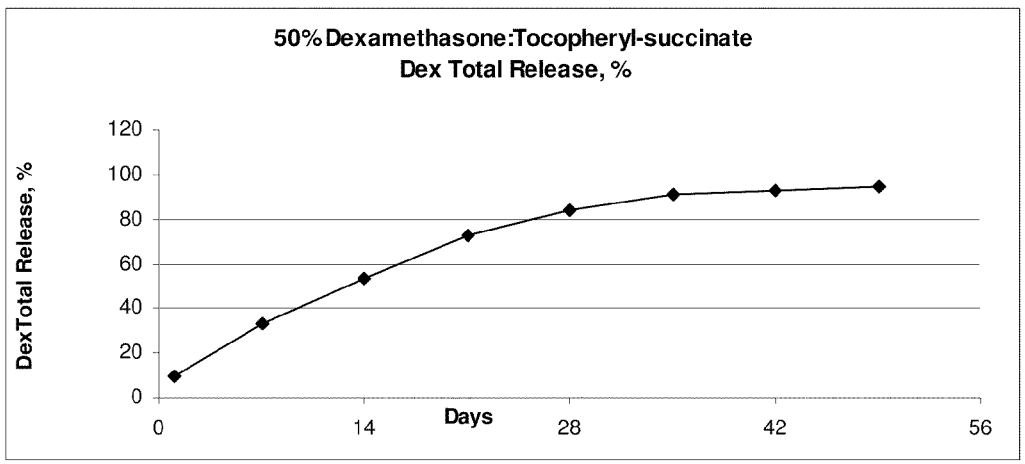
FIG. 11 depicts a dissolution profile of Dex released from a Dex/tocopheryl succinate formulation.

Manufacturing of a Solid Drug Delivery System with dexamethasone and tocopheryl Succinate and its Release Profile Dexamethasone powder and tocopheryl succinate powder were thoroughly mixed at a ratio of 50/50 by weight. The well-mixed powder was filled into a single barrel extruder and heated for 1 hour at 65° C. before extruding through a 1 mm orifice. Micropellets of varying sizes suitable for implants were cut from the extruded filaments for in vitro kinetic testing as shown in FIG. 11.

Example 17

Combination Formulations

Figure 12A:
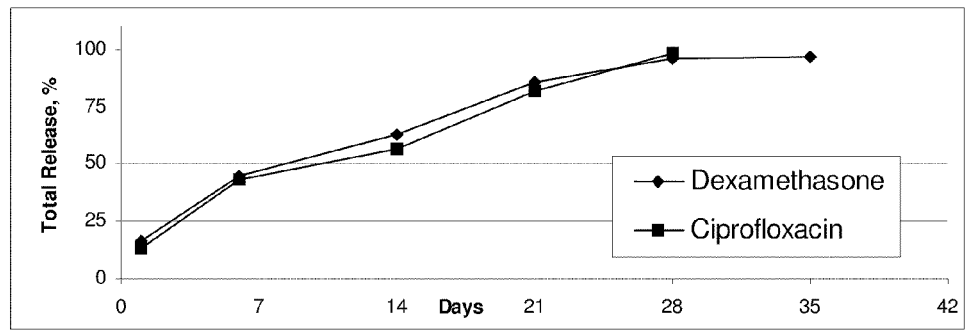
FIG. 12 depicts a dissolution profile of Dex and Ciprofloxacin from a 1:1 formulation of those components in benzyl benzoate (Panel A) and a 3:1 formulation of Dex and Ciprofloxacin in benzyl benzoate (Panel B).

Combination with two or more drugs conveniently formulated with an excipient such as benzyl benzoate provides for sustained and controlled release of the active agents. The variables of volume, concentration and percentages of the ingredients are factors influencing duration and therapeutic concentration of the drug(s) released. As an example, in a 20% (wt) formulation of a 1:1 dexamethasone:ciprofloxacin in benzyl benzoate, the release profile of the two drug is similar and the duration is about twenty-eight to thirty-five days. The release profile of the two drugs is shown in FIG. 12A.

Figure 12B:
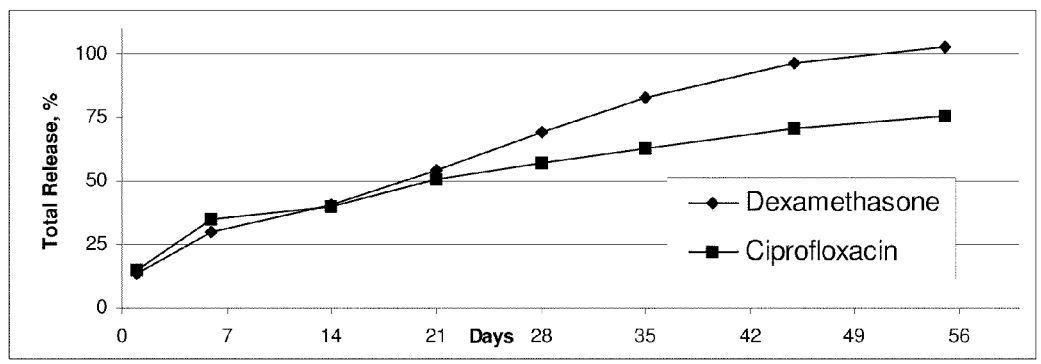

Another useful composition comprises dexamethasone and ciproloxin at a ratio of 3:1 dexamethasone:ciprofloxacin. The duration of release of each drug is prolonged significantly, to about sixty days for dexamethasone and longer for ciprofloxacin, as shown in FIG. 12B.

Example 18

Pharmacokinetics and Metabolism of Injected Formulation Comprising Dex

To examine the in vivo release of dexamethasone in vivo, a composition of 25% dexamethasone by weight in benzyl benzoate (DB) was used: 25 µl (low dose) contained 6 mg dexamethasone, 50 µl (high dose) contained 12 mg dexamethasone. Benzyl benzoate (BB) served as placebo.

The in vivo release of the DB composition was studied in twenty-four rabbits. Twenty-five µl of 25% DB was injected into the posterior segment of one eye of twelve animals and the contralateral eye received a placebo. Another twelve animals received 50 µl of the DB in one eye and 50 µl of the BB placebo in the second eye. Animals were euthanized at the appropriate time points and vitreous humor samples were removed surgically. Dexamethasone concentration was determined by high pressure liquid chromatography (HPLC) as described in Example 5.

Figure 13:
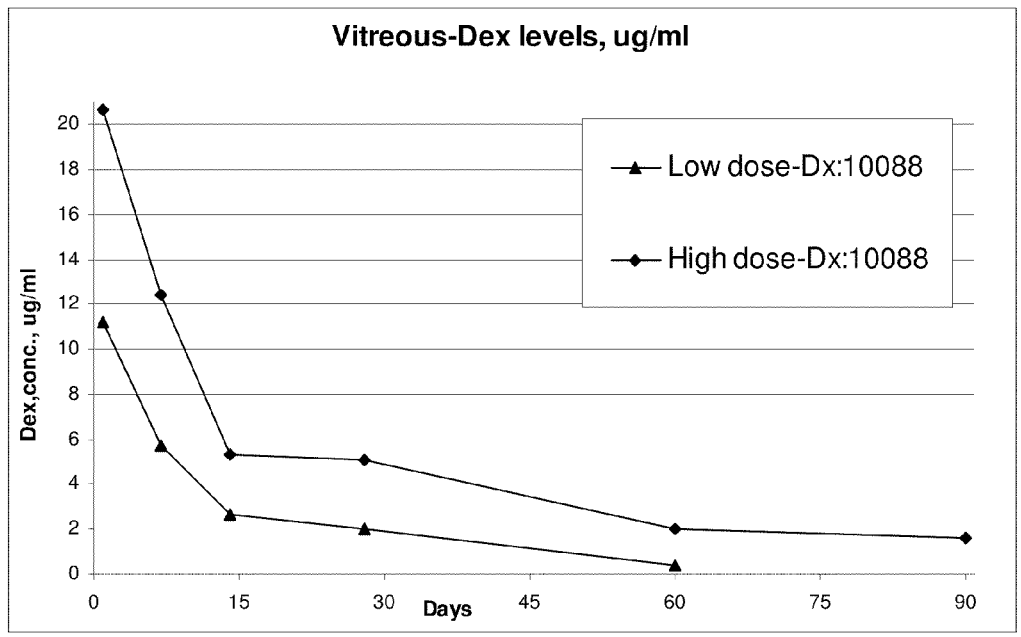
FIG. 13 depicts the concentration of Dex released into the vitreous humor from two formulation of Dex in benzyl benzoate.

For the high dose, the concentration of released dexamethasone was maximal during the first week after insertion, with a mean of 5.56 µg/ml from Day 7 to Day 90, declining to a mean level of 1.85 µg/ml by Day 90. With the low dose, the mean level of dexamethason was 2.8 µg/ml from Day 7 to Day 60, declining to a mean level of 0.8 µg/ml. See FIG. 13. Dexamethasone was not detected in any of the control eyes.

Clinically, the 24 animals receiving the placebo or low or high doses of the DB showed no evidence of inflammation or infection for the entire study. Animals were examined twice weekly both by slit-lamp ophthalmoscopy and fundoscopic examination. No evidence of cataracts, vitreous, or retinal abnormality was observed.

Figure 14:
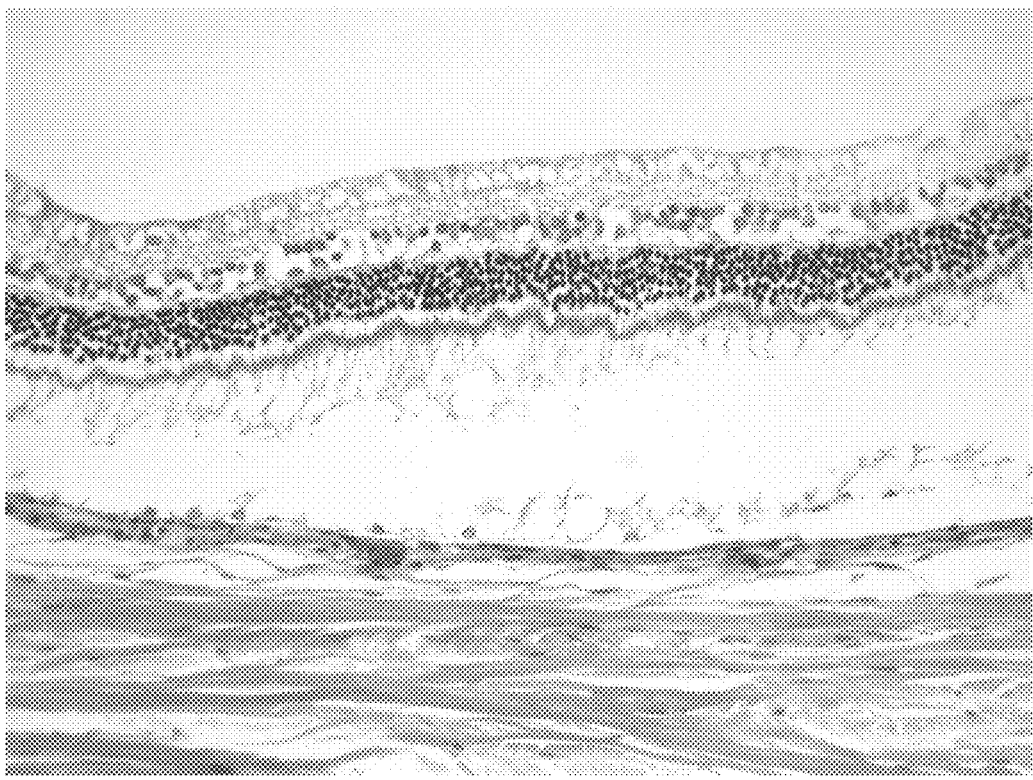
FIG. 14 represents a histopathological slide of rabbit eye tissue thirty days after a posterior segment injection of a formulation of 25% Dex in benzyl benzoate.

Regarding histopathology, three animals were injected with 25 µl of the DB in one eye and 25 µl of the placebo (BB) in the contralateral eye. Another three animals were injected with 50 µl DB in one eye and 50 µl BB in the other eye. They were followed clinically weekly and were sacrificed for histopatholoy at 30 days for the low dose and at 90 days for the high dose. Eyes were fixed in 10% buffered formalin and examined after H & E staining. The anterior segment comprising the cornea, anterior chamber, iris, ciliary body, and lens were normal. The pigment epithelium, Bruch's membrane, and the choroids were all within normal limits. See FIG. 14. There were no obvious differences in the histopathology between the treated and control eyes.

To further examine the in vivo anti-inflammatory effect of DB, 25 µl of 25% DB was injected into the vitreous of one eye of three New Zealand White (NZW) rabbits weighing 3 kg to 3.5 kg. Twenty-four hours later, 2.5 mg of bovine serum albumin (BSA) was injected into both eyes. The animals were examined daily as well as ophthalmologically. Between 10 to 14 days, uveitis with severe fibrinous reaction occurred in the eye unprotected by DB. In the eyes injected with DB, little to no inflammation was detected on examination. Histopathology, the unprotected eye showed chronic and acute inflammatory cells in the uveal tissues as well as in the anterior chamber and the vitreous cavity. In the protected eye, there was minimal evidence of inflammation with few round cell infiltration in the choroids. The cornea, iris, retina and the choroids were histologically intact. See Table 1 below.

TABLE 1

Inflammation in NZW

| NZW | Day 0 | Day 14 |
|---|---|---|
| 1 | | |
| OD | BSA/DB* | 3+ |
| OS | BSA | 0-1+ |
| 2 | | |
| OD | BSA | 3-4+ |
| OS | BSA/DB | Trace |
| 3 | | |
| OD | BSA/DB | 0 |
| OS | BSA | 4+ |

BSA: bovine serum albumin;
DB: 25% dexamethasone/benzylbenzoate
OD: right eye,
OS: left eye;
0-4: severity of posterior segment inflammation, 4+ being maximum Another three NZW rabbits were immunized intravenously (IV) with 10 mg of BSA. Twenty-one days later, following intradermal injection of 0.5 mg BSA/0.1 ml saline, all animals demonstrated a strong (+4) Arthus reaction indicating the animals were systemically immuned to the BSA. On day thirty, one eye of each animal was injected intravitreally with 25 µl of a 25% DB composition, and 24 hours later 0.5 mg BSA/0.1 ml normal saline was injected into both eyes. Severe uveitis developed and persisted in the ensuing seven to ten days in the unprotected eye, while the protected eye was judged to be normal. On day sixty, repeat skin testing showed that the (+4) Arthus reaction remained intact, and reinjection of 0.5 mg BSA/0.1 ml normal saline showed similar protection as observed on day 30. These studies imply that DB has immediate and sustained protective effect in the experimental eye. When these animals were again challenged with 0.5 mg BSA/0.1 ml normal saline at 90 days, uveitis developed in all eyes, but the inflammation in the protected (DB) eye appeared to be less severe. See Table 2 below. Protection against inflammation with 25 µl of DB lasted for sixty days. At ninety days, there may have been an insufficient therapeutic level of Dexamethasone in the eye.

TABLE 2

Inflammation in protected and unprotected NZW eyes.

| NZW | Day 0 | Day 14 | Day 30 | Day 60 | Day 90 |
|---|---|---|---|---|---|
| 1 | | | | | |
| OD | BSA | | 3-4+ | 3-4+ | 3-4+ |
| OS | BSA/DB* | | 0 | 0 | 2-3+ |
| 2 | | | | | |
| OD | BSA | | 4+ | 3-4+ | 3+ |
| OS | BSA/DB | | Trace | 0+ | 2-3+ |
| 3 | | | | | |
| OD | BSA | | 4+ | 4+ | 4+ |
| OS | BSA/DB | | 0-1+ | 0 | 2-4+ |

BSA: bovine serum albumin;
DB: 25% dexamethasone/benzylbenzoate
OD: right eye,
OS: left eye;
0-4: severity of posterior segment inflammation, 4+ being maximum Another three NZW rabbits were immunized similarly IV with 10 mg BSA. Twenty-four hours later, one eye of each animal was injected with 50 µl of 25% DB. At three months (90 days), intradermal skin testing evoked a +4 reaction. One week later, 0.5 mg BSA/0.1 ml normal saline was injected in both eyes of each animal. The protected eye (injected with 50 µl 25% DB) showed little to no clinical uveitis when compared to the contralateral unprotected eye. This indicates that chronic sustained release of Dexamethasone was able to protect the eye up to three months when challenged locally with BSA. See Table 3 below.

TABLE 3

Sustained protection in protected NZW eyes.

| NZW | Day 0 | Day 90 |
|---|---|---|
| 1 | | |
| OD | BSA/DB* | 0-1+ |
| OS | BSA | 4+ |
| 2 | | |
| OD | BSA/DB | 0+ |
| OS | BSA | 3-4+ |
| 3 | | |
| OD | BSA/DB | 0-1+ |
| OS | BSA | 4+ |

BSA: bovine serum albumin;
DB: 25% dexamethasone/benzylbenzoate
OD: right eye,
OS: left eye;
0-4: severity of posterior segment inflammation, 4+ being maximum Example 19

Pharmacokinetics and Metabolism of Injected Formulation Comprising TA

A composition of 25% TA (Triamcinolone Acetonide) by weight in benzyl benzoate (TA/B) was used: 25 µl containing 7.0 mg TA and 50 µl containing 14 mg TA. Benzyl benzo (BB) served as placebo.

Figure 15:
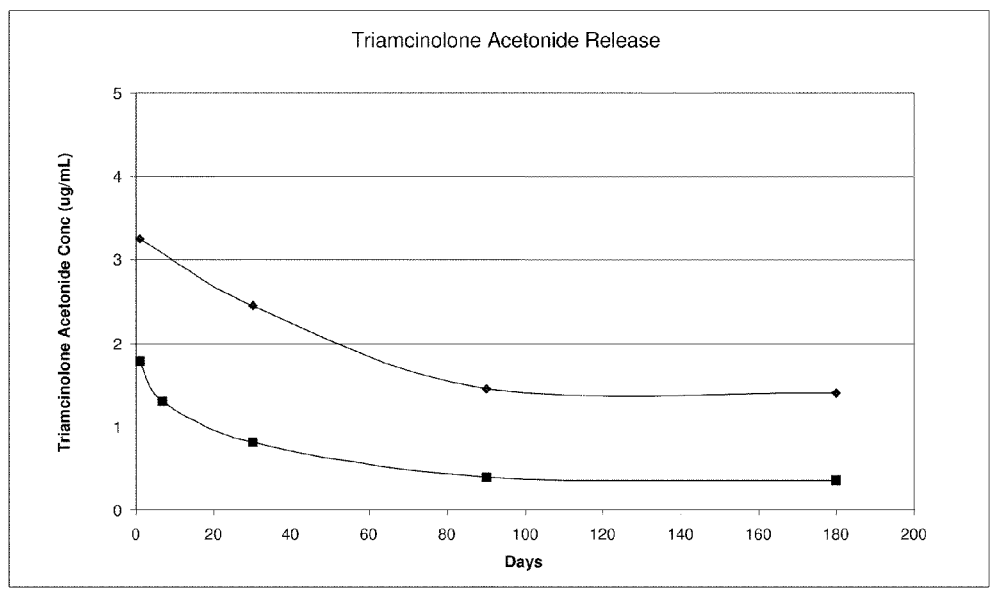
FIG. 15 depicts the vitreous concentration of tramcinolone acetonide (TA) released from a TA:benzyl benzoate composition.

The in vivo release of the TA was studied in twenty-seven rabbits. Twenty-five µl (25 µl) of the composition was injected into the posterior segment of one eye of twelve animals and the contralateral eye received 25 µl of BB. Another twelve animals received 50 µl of the same composition into posterior segment of one eye and 50 µl BB into the second eye. Animals were euthanized at the appropriate time points (each time point n=3) and vitreous humor samples were removed surgically for TA concentration by high-pressure liquid chromatography (HPLC) as described in Example 5. The mean vitreous concentration TA for the 50 µl TA/B at twenty-four hours was 3.25 µg/ml; at 1 month 2.45 µg/ml; at three months 1.45 µg/ml; and at six months 1.56 µg/ml. The mean vitreous TA level over the 6 month period was 2.17 µg/ml. The mean vitreous concentration of TA of the 25 µl TA/B animals was 1.78 µg/ml at twenty-four hours; 1.31 µg/ml at one week; 0.81 µg/ml at one month; 0.4 µg/ml at three months; and 0.36 µg/ml at six months, with a mean of 0.93 µg/ml over a six month period. TA was not detected in any of the control eyes. See FIG. 15. For the 25 µl dose, near zero-order release was been observed in vivo for 270 days (data not shown). For the 50 1 dose, near zero-order release has been observed in vivo for 365 days (data not shown).

Clinically, the twenty-seven animals receiving the BB placebo showed no evidence of inflammation or infection for the entire study. Animals were examined twice weekly both by slit-lamp ophthalmoscopy and fundoscopic examination. No evidence of cataracts, vitreous or retinal abnormality was seen.

Regarding histopathology, six animals were injected with 50 µl of 25% TA/B in the right eye and 50 µl of BB in the other eye. They were followed clinically weekly and were sacrificed for histopathology at 180 days. Eyes were fixed in 10% buffered formalin and examined after H & E staining. The anterior segment comprising the cornea, anterior chamber, iris, ciliary body and lens was normal. Histopathology of the posterior segment (including the vitreous, retina, photoreceptors cells, pigment epithelium, Bruch's membrane and the choroids) was within normal limits. There were no obvious differences in the histopathology between the treated and the control eyes.

Example 20

Solid Implant Comprising Dex

Figure 16:
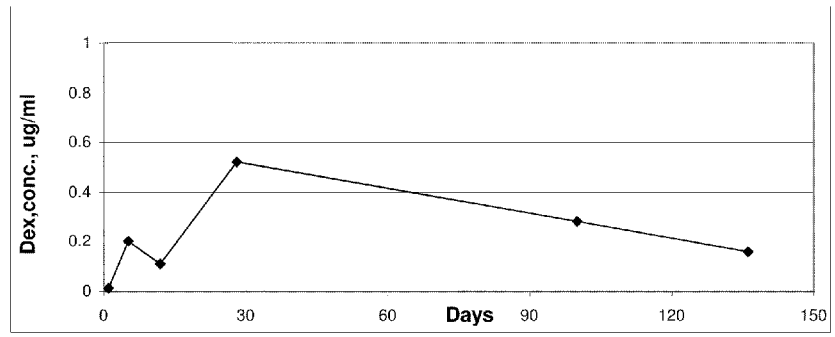
FIG. 16 depicts the in vivo release of Dex released into the aqueous humor from a Dex:dl-alpha tocopherol succinate formulation.

The levels of dexamethasone released from a solid implant was studied in the anterior chamber of a NZW rabbit. A mixture of 50:50 dexamethasone (Upjohn) and dl-alpha tocopherol succinate (Sigma) was extruded through an aperture of 790 μM mm at 25° C. One (1) mgm of this extruded mixture was surgically placed in the right anterior chamber of a 4 kg NZW female rabbit. Sampling of the aqueous humor from the anterior chamber (AC) for HPLC dexamethasone analysis was performed in accordance with the above example. Therapeutic sustained release levels of dexamethasone were observed. See FIG. 16. Clinically, the animal's eye was completely quiescent and the composition was judged to be biocompatible.

Example 21

Figure 17:
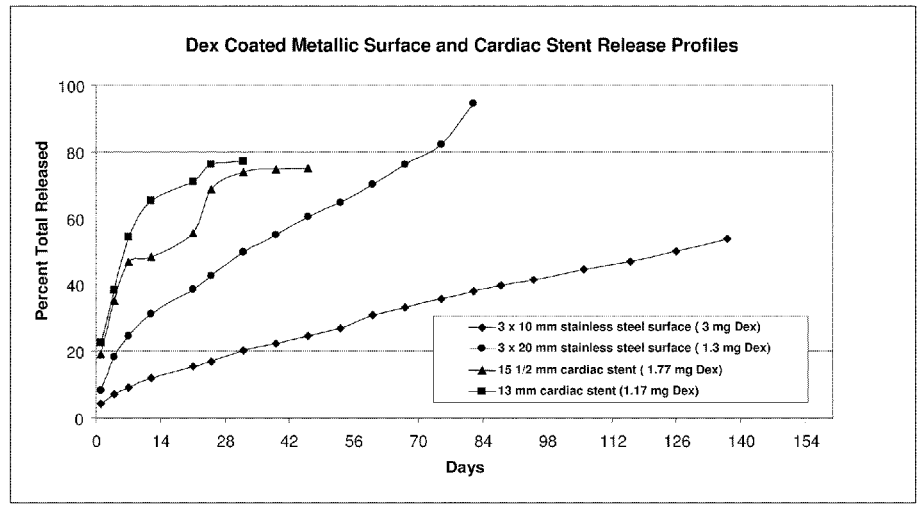
FIG. 17 depicts the dissolution of Dex from a Dex:acetone: tocopherol succinate formulation applied to solid surfaces.

Sustained Release of dexamethasone/dl-alpha Tocopherol Succinate Coating of Stainless Steel Surface and Cardiac Stents A mixture of 2:8:1 (wt) of dexamethasone:acetone:tocopherol succinate coating was applied to two stainless steel tubing surfaces and two commercial cardiac stents. Coating was achieved by dipping and oven drying. Elution of dexamethasone for HPLC analysis was done in a 20 ml distilled water vial and exchange of 75% of the total volume took place per period of assay. See FIG. 17. Tocopherol succinate has been demonstrated to be an effective coating medium on steel surfaces for controlled drug release. The application of this methodology could be extended to various materials and surfaces including wood, glass, various metals, rubber, synthetic surfaces such as teflon, plastics, polyethylene tubings and the like.

Example 22

Formulations Comprising Cyclosporine in Tocopherol Succinate

Figure 18:
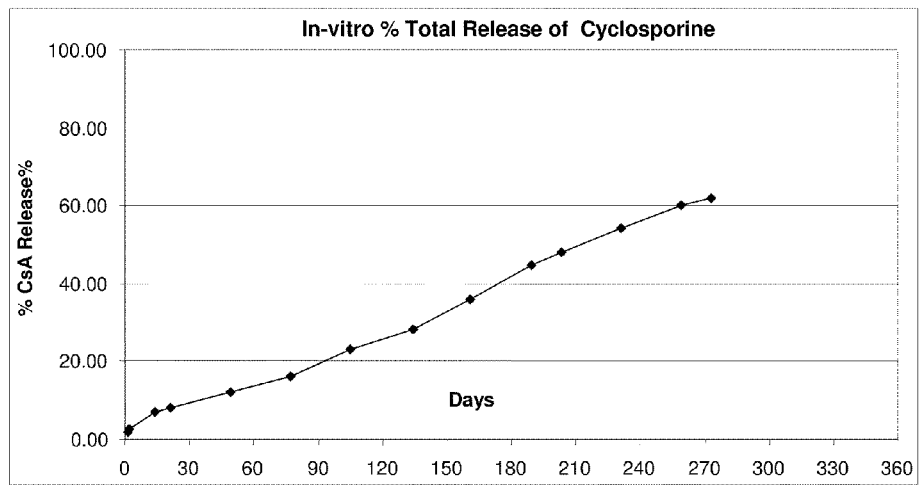
FIG. 18 shows the dissolution profile of cyclosporin from a cyclosporin: tocopherol succinate formulation.

To study the in vitro release of 25:75 dl-alpha tocopherol: Cyclosporin A, cyclosporin was mixed with tocopherol succinate and extruded at 25° C. through an aperture of 790 μM. One mg (1 mg) of the material was placed in 10 ml distilled water vial and aliquots were sampled for dissolution as described above. See FIG. 18. Prolonged sustained release in a linear fashion was observed for about 272 days.

Figure 19:
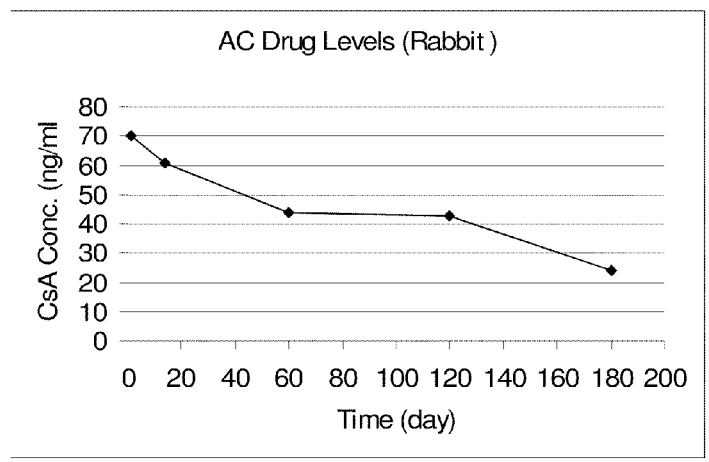
FIG. 19 depicts an in vivo release profile of cyclosporin from a tocopherol succinate:cyclosporin formulation implanted the anterior chamber of a New Zealand White (NZW) rabbit.
Figure 20:
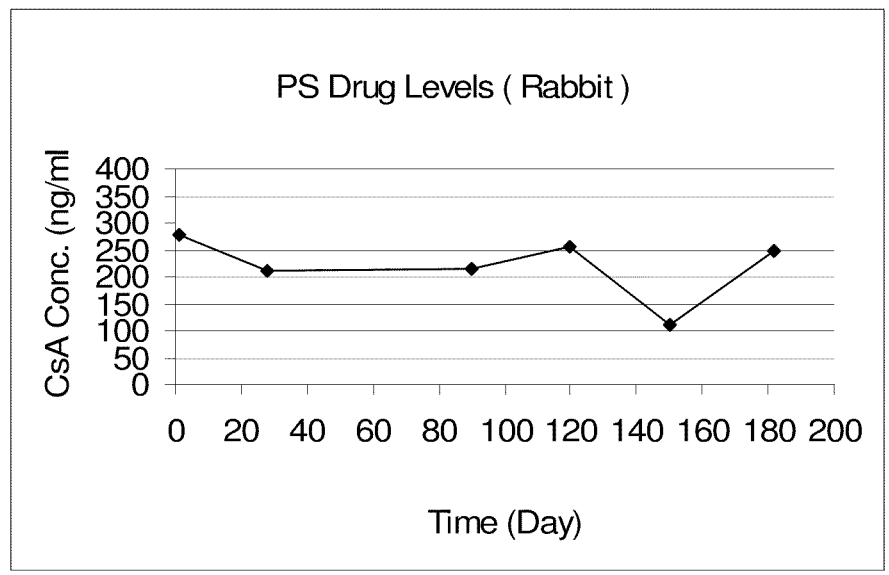
FIG. 20 depicts an in vivo release profile of cyclosporin from a tocopherol succinate:cyclosporin formulation implanted the posterior segment of a NZW rabbit eye.

To study the in vivo release profile, 0.75 mg of the 25:75 tocopherol succinate:cyclosporin was implanted surgically in the right anterior chamber (AC) of the 4.0 kg NZW female rabbit. The AC was tapped at the above time-points for HPLC determination of CsA in the aqueous humor. See FIG. 19. Additionally, 5.0 mg of 25:75 tocopherol succinate:cyclosporine was implanted surgically into the left posterior segment (PS) of a 4 kg NZW female rabbit eye. The vitreous humor in the PS was tapped at the above time-point for CsA HPLC analysis. See FIG. 20.

Figure 21:
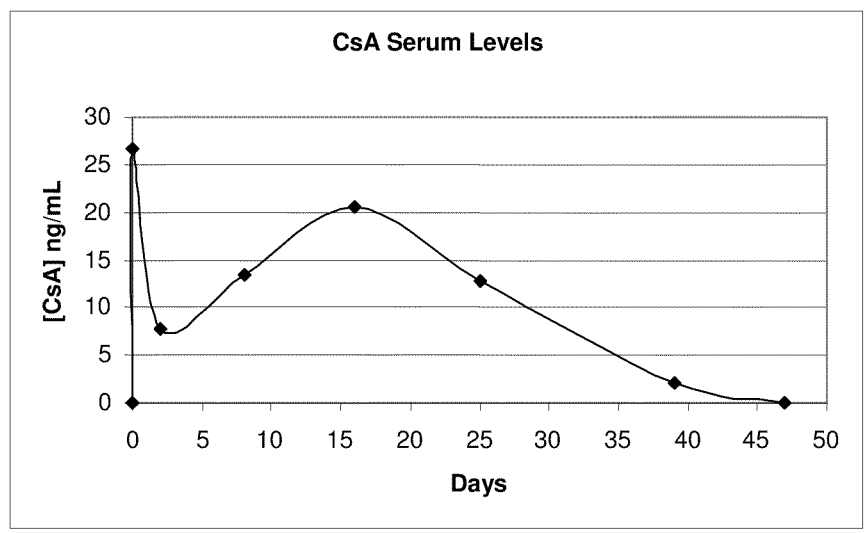
FIG. 21 shows an in vivo release of cyclosporine from a tocopherol succinate:cyclosporin formulation implanted in the peritoneal cavity of a rat.

In another in vivo release study, 30 mg (3×10 mg) of a 25:75 tocopherol succinate:cyclosporin formulation was extruded through a 1 mm aperture. The segments were implanted in the peritoneal cavity of an adult male Sprague-Dawley rat with a trocar through a 3 mm incision after local 0.5% lidocaine infiltration. Cardiac puncture was performed for blood CsA LCMSMS analysis. See FIG. 21.

Implants of cyclosporin:tocopherol succinate were injected by needle trocar in various organs in Sprague-Dawley rats to determine cyclosporin distribution. More specifically, extruded 20:80 tocopherol succinate:cyclosporin of various weights were implanted. After sacrifice and harvest, all tissues were dried in a tissue concentrator for 48 hours, crushed and soaked in 1 ml of MeOH containing 10 ng/ml CsD. Analysis were performed with Mass Spec Liquid Chromatography. CsA was observed as indicated below in Table 4 and Table 5. Abbreviations: ant anterior, post posterior, hem hemisphere.

TABLE 4

Cyclosporin distribution in rat liver and brain.

| | mg dried tissue | ng/ml CsA | ng/mg CsA |
|---|---|---|---|
| Liver #1 Upper Lobe, Sacrificed Day 5, 2 mg 80% CsA in tocopherol succinate was implanted into the right third of the middle lobe* | | | |
| Upper lobe | | | |
| right third | 71.4. mg | 2540 | 35.6 |
| middle third | 119.4 | 191 | 1.6 |
| left third | 88.4 | 184 | 2.1 |
| middle lobe | | | |
| right third* | 83.3 | 2360 | 28.3 |
| left third | 88 | 878 | 10 |
| left third | 49.2 | 2620 | 53.2 |
| blood | na | 0 | na |
| Observation: CsA distribution was detected in both upper and middle lobes when implant was implanted in the middle lobe.* | | | |
| Liver #2 Lower Lobe, Sacrifice 24 hours, 2 mg of implant injected. | | | |
| right fifth | 99.3 | 254 | 2.6 |
| right middle fifth | 59.6 | 144 | 2.4 |
| Implant* | | 138.8 | 2420 |
| left middle fifth | 77.5 | 1710 | 22 |
| left fifth | 53.5 | 278 | 5.2 |
| Observation: Sacrifice at 24 hours showed much higher concentration in the section of the liver containing the implant. | | | |
| Brain #1, Sacrifice 24 hours, 1 mg of the formulation was implanted. | | | |
| left ant hem | 47.2 | 72.1 | 15.3 |
| left post hem | 79.3 | 180 | 2.3 |
| right ant hem* | 52.7 | 1190 | 22.6 |
| right post hem | 60.8 | 385 | 6.3 |
| blood | na | 0 | na |
| Observation: CsA distribution was noted in both hemispheres even though the implant was placed in the right ant hem.* | | | |
| Brain #2, 1 mg formulation implanted in right ant hem.* | | | |
| left ant hem | 42.2 | 478 | 11.3 |
| left post hem | 68.6 | 127 | 1.9 |
| right ant hem* | 73.9 | 401 | 5.4 |
| right post hem | 113.7 | 96 | 0.8 |
| blood | na | 0.29 | na |
| Observation: Similar to brain # 1, the left ant hem showed much higher concentration. | | | |

*Site of implantation.

TABLE 5

Cyclosporin distribution in rat spleen and kidney.

| | mg dried tissue | ng/ml CsA | ng/mg CsA |
|---|---|---|---|
| Spleen, sections right to left, 1 mg implant in section #7.* | | | |
| section #1 | 10.3 | 217 | 21.1 |
| section #2 | 16.2 | 72.5 | 4.5 |
| section #3 | 12.9 | 17.7 | 1.4 |
| section #4 | 24.9 | 62 | 2.5 |

TABLE 5-continued

Cyclosporin distribution in rat spleen and kidney.

| | mg dried tissue | ng/ml CsA | ng/mg CsA |
|---|---|---|---|
| section #5 | 22.5 | 72.9 | 3.2 |
| section #6 | 26.8 | 101 | 3.8 |
| section #7* | 29 | 1800 | 62 |
| blood | na | 0 | na |
| Observation: Distribution appears higher at the opposite pole of the spleen. Kidney, 075 mg implant in lower third. | | | |
| upper third | 156.8 | 314 | 2 |
| middle | 85.5 | 333 | 3.9 |
| lower third* | 106.1 | 165 | 1.6 |
| Observation: CsA distribution throughout kidney. | | | |

*site of implantation.

Example 23

Transdermal Delivery of Insulin

The comparison of injected versus transdermal delivery of several formulation of insulin was studied in a mouse model. One mg of porcine insulin was injected IP (intraperitoneal) into a mouse. A precipitous drop in glucose level was found within one-half hour and developed into hypoglycemia after one hour. Hypoglycemia persisted below perceptible levels and the animals never recovered. One mg of porcine insulin was mixed with 0.1 ml of tocopherol acetate and injected IP, perceptible drop in glucose level was seen up to 3 hours and the animal remained hypoglycemic and did not recover. IP glucose infusion did not reverse the hypoglycemia. One mg of porcine insulin mixed with 0.1 ml of tocopherol acetate was applied topically on the skin of a shaved mouse. A slow decline of the glucose level was seen, with the lowest level determined at 5.5 hours. A return towards pre-treatment levels was seen at 24 hour and 48 hour. Tocopherol IP was able to slow the hypoglycemic effect of insulin. Transdermal insulin w Topcopherol Ac produced reduction in glucose levels with slow recovery to pre-treatment levels after 24-48 hours. Sustained release of transdermally administered insulin was observed.

Figure 22:
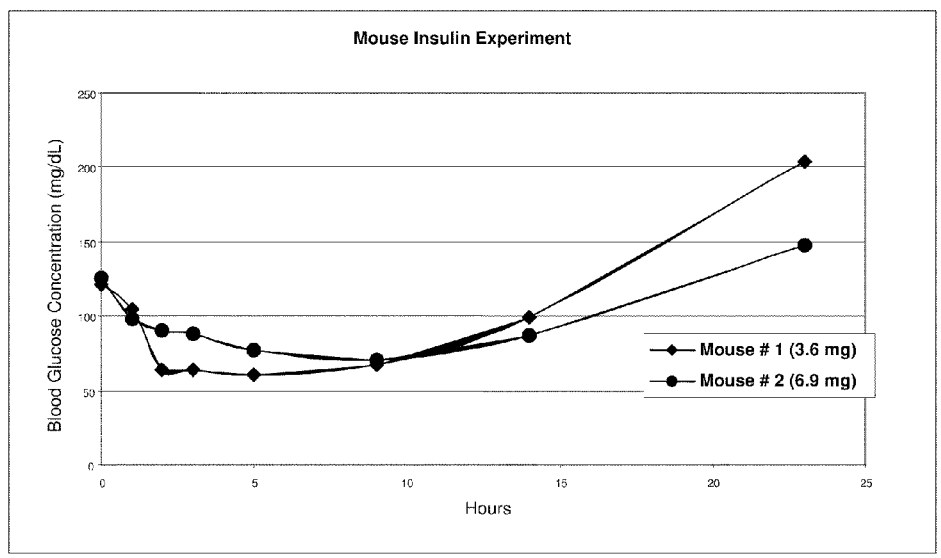
FIG. 22 plots in vivo blood glucose levels in mice treated with a transdermal formulation of insulin in tocopheryl acetate.

Porcine insulin (20 mg) was mixed in 199 mg/ml of tocopheryl acetate and formed a paste (or gel) which and was applied to the backs of shaved albino mice as follows: Mouse #1 was treated with 39.8 mg of insulin/tocopherol acetate paste, equaling 3.6 mg of insulin; mouse #2 was treated with 75.2 mg of insulin/tocopherol acetate paste, equaling 6.9 mg of insulin. Tail blood glucose levels were determined by Home Diagnostics, Inc. True Track smart system at intervals depicted in FIG. 22. A drop in glucose level was seen as early as one-half hour after transdermal application followed by sustained depressed levels for up to fifteen hours. By twenty-four hours, glucose had returned to pre-treatment levels followed by rebound or hyperglycemic concentrations for the next twenty-four hours. Sustained release of transdermal administered insulin has been demonstrated.

Pharmaceutical agents that may be delivered by this platform include insulins, GLP-1s, analgesics, anesthetics, narcotics, angiostatic steroids, anti-inflammatory steroids, angiogenesis inhibitors, nonsteroidal anti-inflammatories, anti-infective agents, anti-fungals, antimalarials, anti-tuberculosis agents, antivirals, alpha androgenergic agonists, beta adrenergic blocking agents, carbonic anhydrase inhibitors, mast cell stabilizers, miotics, prostaglandins, antihistamines, antimicrotubule agents, antineoplastic agents, antiapoptotics, aldose reductase inhibitors, antihypertensives, antioxidants, growth hormone antagonists, vitrectomy agents adenosine receptor antagonists, adenosine delaminate inhibitor, glycosylation antagonists, anti-aging peptides, topoisemerase inhibitors, anti-metabolites, alkylating agents, antiandrigens, anti-oestogens, oncogene activation inhibitors, telomerase inhibitors, antibodies or portions thereof, antisense oligonucleotides, fusion proteins, luteinizing hormone releasing hormones agonists, gonadotropin releasing hormone agonists, tyrosine kinase inhibitors, epidermal growth factor inhibitors, ribonucleotide reductase inhibitors, cytotoxins, IL2 therapeutics, neurotensin antagonists, peripheral sigma ligands, endothelin ETA/receptor antagonists, antihyperglycemics, anti-glaucoma agents, anti-chromatin modifying enzymes, obesity management agents, anemia therapeutics, emesis therapeutics, neutropaenia therapeutics, tumor-induced hypercalcaemia therapeutics, blood anticoagulants, anti-proliferatives, immunosuppressive agents, tissue repair agents, and psychotherapeutic agents.

Example 24

Formulation Effective in Treating Brain Tumors

The following example used a partial tumor resection brain tumor model to investigate whether tissue injury resulted in an accelerated, proliferative index or accelerated tumor growth. It also indicated that suppression of inflammatory cytokines and vascular endothelial growth factors with local sustained-release cortico steroid will alter the rate of recurrence and growth in an experimental mouse tumor model. This experiment tused a resection/recurrent mouse glioblatoma model in ascertaining the effects of dexamethasone on the post-surgical environment following tumor resection.

Figure 23:
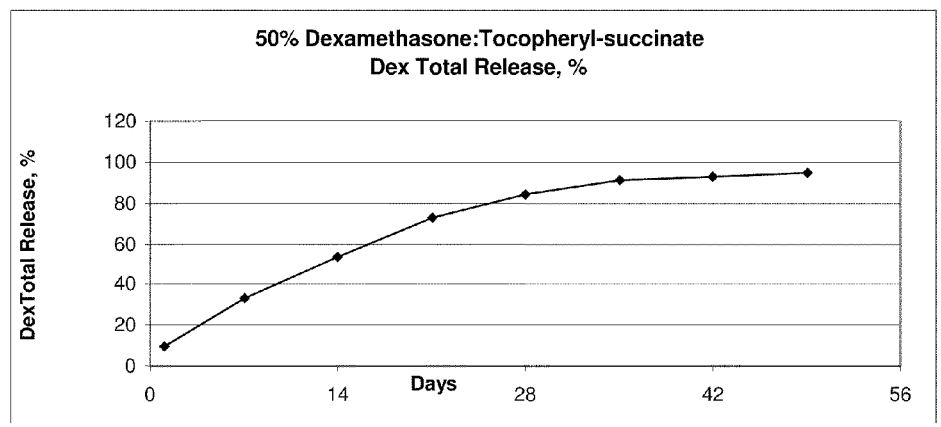
FIG. 23 shows in vitro release of Dex from a pellet of 1.5 mg of 50/50 wt Dex/tocopheryl succinate.

A pellet of 1.5 mg of 50/50 wt. dexamethasone/tocopheryl succinate was prepared in a 1.0 diameter press. The in vitro kinetics are shown in FIG. 23.

Briefly, mice were anesthetized by intramuscular injection of a cocktail of ketamine (22-44 mg/kg), xylazine (2.5 mg/kg), and acepromazine (0.75 mg/kg). Ten thousand GL-26 rat glioblastoma cells were implanted stereotactically into the right basal ganglia of the animal using a mouse stereotactic frame (Kopf Instruments, Tujunga, Calif.). At day 15 after tumor implantation, the animals were scanned in a 1.5 T MRI with a T-1. Contrast medium was give via tail vein injection prior to scanning. At day 18 another imaging was done to confirm the tumor progression. Animals with similar tumor size were selected for the study. Animals underwent craniotomy and tumor resection on day 19 following general anesthesia. The tumor was resected to about 80% completion. The extent of resection was verified by post-operative MRI imaging. Three animals each with similar residual tumor were grouped into resected and resected plus dexamethasone-tocopheryl succinate delivery system. In the treated group sustained-release dexamethasone was placed into the resection cavity. The expansion of the residual tumor was monitored by MR imaging. The growth rate was determined and compared to that of control and resection arms of the study.

Figure 24:
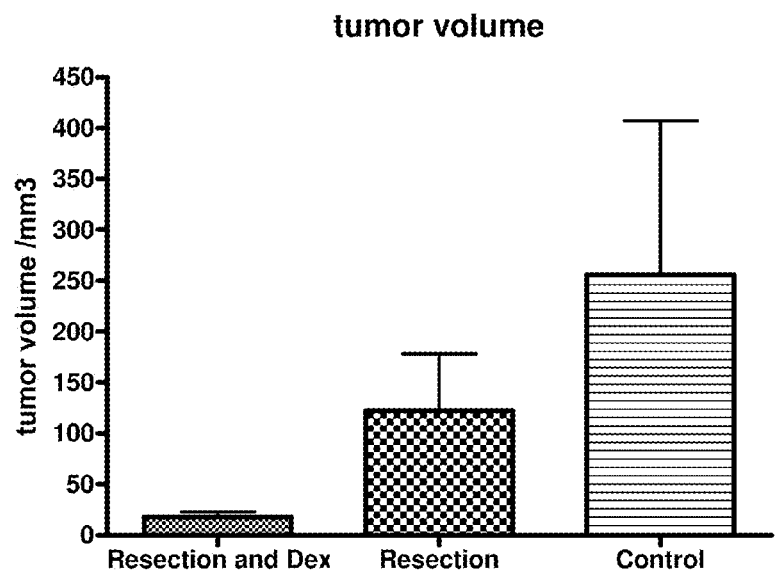
FIG. 24 presents a bar graph reflecting brain tumor volume following either resection, or resection and susquent treatement with Dex.

Animals implanted with G126 mouse glioma cell line will grow to a mean volume of 110 mm$^3$ at day 25. The mean survival is 28 days. In the current experiment there was a significant difference in the volume of the recurrent tumor at day 30 between the resected (122.5 mm$^3$) and the resected group treated with intratumoral sustained-release dexamethasone (18 mm$^3$) and the control (233.5 mm$^3$). See FIG. 24.

These data suggest that dexamethasone delivered locally following resection appears to be effective in altering the rate of recurrence.

Example 25

In Situ Personalized Anti-Cancer Vaccine Production

The use of aldehydes such as formaldehyde to kill or alter the cellular or viral components of pathogens for the formation of vaccines is well known. The Salk polio vaccine is one example. The pathogens are exposed to a carefully measured amount of an aqueous aldehyde solution resulting in the death of the pathogen or chemical alteration of the cellular or viral components to destroy pathogenicity. In many cases the resultant altered cells, viruses, or components are recognized by the body's immune system as foreign resulting in therapeutic antibody production. For the production of a patient-specific anticancer vaccine (PSAV) to a tumor, because the highly reactive aqueous aldehyde solutions are very mobile fluids they would be difficult to confine to the target area if injected into the body; and considerable collateral damage to healthy tissues might occur. Thus, presently the exposure of the target malignant cells to the aldehyde is done outside the body and the resultant attenuated pathogen material is then injected into the body. Excising tumor tissue for extracorporeal vaccine production can be traumatic, and often tumors such as glioblastomas are inoperable. Hence, there remains a need for an improved approach to PSAV techniques.

This embodiment allows for the precision injections of controlled amounts of novel aldehyde, especially formaldehyde, polyoxymethylene prodrug formulations directly into tumors in the body. The precise, controlled nature of these prodrug injections limits cell death or augmentation to tumor tissue only, with little or no collateral damage to healthy tissues. The subsequent release of resultant attenuated tumor cells or augmented cell material into the blood stream induces personalized antibody formation that eradicates any remaining original tumor or daughter tumors that may have metathesized to other sites in the body. This process is classified as producing a patient-specific anticancer vaccine (PSAV).

The novelty of this embodiment is the use of solid and liquid oxymethylene polymers as controlled release prodrugs of the desired aldehydes. Aldehydes have the propensity to homopolymerize to a variety of cyclic trimers and linear oxymethylene or substituted oxymethylene polymers of a wide spectrum of molecular weights. In water, these trimers and polymers slowly revert back to their aldehyde monomers. This property offers the ability to inject with precision these aldehyde prodrugs or their injectable formulations with excipients into tumors in the body to allow for the controlled and/or sustained release of the desired aldehyde into the tumor with little or no damage to healthy tissue. The subsequent release of killed or attenuated tumor cells or cellular material into the blood stream induces immune responses to produce therapeutic antibodies to destroy tumor cells throughout the body.

Some oxymethylene polymers and trimers for this embodiment are, for example: Paraformaldehyde, Trioxane, Oxymethylene polymers of acetaldehyde, Paraldehyde, and Oxymethylene polymers of gluteraldehyde.

These oxymethylene polymers and trimers can be implanted by themselves or as mixtures with excipients into the tumor mass. A desirable, minimally invasive method is by injection through 20 gauge to 36 gauge hypodermic needles of fluid liquid polyoxymethylene/excipient formulations. Excipients are disclosed herein and in U.S. Pub. No. 2006/0073182. Some example excipients useful in the present embodiment include benzyl benzoate, tocopherol acetate, and triethyl O-acetyl citrate. An illustrative but non-limiting example of a formulation would be triethyl O-acetyl citrate containing 5 to 50% by weight of micronized crystals of paraformaldehyde.

Depending upon the size of the target tumor, 1.0 µl to 100 µl of this formulation may be injected into the tumor mass.

Example 26

Omega-3 Fatty Acids and their Esters for Injectable Sustained Drug Release Formulations As noted above, the embodiments thus provide for the novel concept of injections of omega-3 fatty acids and their esters by themselves or as novel and therapeutic formulations with active agents directly into strategic areas of the human or animal bodies to provide for the sustained release of the omega-3 compounds and therapeutic but nontoxic levels of the active agents for periods of months to over a year.

The process of injecting small amounts of these omega-3 fatty acid/ester alone or their formulations containing active agents at the site of the malady is not only maximally effective and efficient but also avoids the waste and potentially increased danger of systemic oral administration. These novel sustained drug release formulations of the omega-3 liquids alone or in combination with the other excipients disclosed herein and in U.S. Pub. No. 2006/0073182 can be injected into a variety of body areas or organs such as but not limited to the breast, brain, pancreas, liver, prostate, lung, etc. An especially promising application is intraocular injection into the anterior or posterior segments of the eye. Among a number of maladies to be treated, as listed herein and in US 2006/0073182, are those of the retina such as macular degeneration, retinitis pigmentosa, proliferative vitreoretinopathy, to name a few. A potentially advantageous property of DHA, EPA, and their esters is their importance in maintaining healthy retinal tissue and their required presence for proper development of neonatal retinal function. See, e.g., Jeffrey et al., 36(9) Lipids 859-71 (2001); SanGiovanni & Chew, 24(1) Prog Retin Eye Res. 87-138 (2005); Bazan, 29(5) Trends Neurosci. 263-71 (2006); King et al., 26(17) J. Neurosci. 4672-80 (2006). Indeed, it is quite possible these beneficial effects of DHA/EPA and their esters in neural development might lead to their injectable formulations being potent adjuvants for successful stem cell implantation and development especially in the retina, brain, spinal cord, and the like. Also these injectable formulations use as adjuvants for successful stem cell development of pancreatic tissue (diabetes), cardiac tissue (coronary therapy), or skin tissue (burn therapy) to name a few await investigation.

Some more specific, but not limiting, examples contemplated for intraocular therapies are for inflammatory maladies of the retinal area. Injection through 25 G to 30 G needles into the posterior segment of 10 µl to 60 µl liquid microspheres of ethyl DHA/ethyl EPA alone or as mixtures containing 10% to 50% by weight of microcrystalline dexamethasone or triamcinolone acetonide. This provides for the maintenance of therapeutic levels of the omega-3 fatty acids or the approximately 0.1 to 1.0 µg/ml therapeutic concentration of the steroids in the area of the retina for periods of months to over a year. In the case of anti-VEGF therapy similar amounts of such agents as ranibizumab or bevacizumab could be employed in a similar manner with the omega-3 excipients.

The extensive list of other beneficial agents employed for the list of a wide variety of maladies are disclosed herein and in U.S. Pub. No. 2006/0073182.

Example 27

Formulations Containing Steroids and Antioxidants

This embodiment relates generally to novel injectable and topically applied formulations containing both steroids and antioxidants. These formulations allow the application of steroids to achieve their intended benefits (anti-inflammation, immune modulation) without initiation of harmful oxidative chemistries. These example formulations are composed of one or more of the steroids listed in Group A combined with one or more of the antioxidants listed in Group B and all dispersed or dissolved in one or more of the delivery vehicles selected from the excipients described herein and listed in Group C and also described in U.S. Pat. Appl. Pub. No. 2006/0073182.

| Group A Steroids | |
|---|---|
| triamcinolone | dexamethasone diethyl aminoacetate |
| triamcinolone acetonide | dexamethasone isonicotinate |
| triamcinolone diacetate | dexamethasone palmitate |
| triamcinolone acetate | prednisone |
| triamcinolone disodium phosphate | prednisolone |
| triamcinolone hemisuccinate | prednisolone acetate |
| triamcinolone benetonide | prednisolone sodium phosphate |
| dexamethasone | methylprednisolone |
| dexamethasone acetate | methylprednisolone acetate |
| dexamethasone disodium phosphate | methylprednisolone sodium succinate |
| dexamethasone 3,3-dimethylbutyrate | paramethasone etrahydrocortexolone |
| cortisone | betamethasone |
| cortisone acetate | betamethasone acetate |
| hydrocortisone | betamethasone disodium phosphate |
| hydrocortisone acetate | |
| tetrahydrocortisol | betamethasone benzoate |
| fludrocortisone | betamethasone valerate |
| fludrocortisone acetate | betamethasone dipropionate |
| fludrocortisone phosphate | betamethasone adamantoate |
| anacortive | beclomethasone |
| anacortive acetate | beclomethasone dipropionate |
| mometasone furoate | diflorasone |
| fluocinolone | diflorasone diacetate |

| Group B Antioxidants | |
|---|---|
| ascorbic acids and salts | retinyl palmitate |
| ascorbyl palmitate | probucol |
| ascorbyl dipalmitate | erythorbic acid |
| ascorbyl stearate | sodium erythorbate |
| ascorbyl-2,6-dibutyrate | α-lipoic acid |
| d-tocopherol (α,β,γ,δ isomers) | isocitrate |
| dl-tocopherol (α,β,γ,δ isomers) | lutein/zeaxanthin/meso-zeaxanthin |
| the acetate, hemisuccinate, nicotinate and succinate-PEG ester derivatives of the above tocopherol isomers | eugenol |
| | isoeugenol |
| | (−)-epicatechin |
| glutathione | (−)-epigallocatechin gallate |
| β-carotine | benzyl alcohol |
| carnitine | benzyl benzoate |
| carnitine acetate | 2,6-di-tertbutyl-4-methoxy phenol |
| trans reveratrol | butylated hydroxytoluene |
| retinoic acid | butylated hydroxyanisole |
| retinyl palmitate | quercetin |
| melatonin | catechin |
| timolol | rutin |

| Group B Antioxidants | |
|---|---|
| luteolin | coenzyme Q |
| kaempferol | fisetin |
| thyroxine | methyl gallate |
| pyrroloquinolone | superoxide dismutase |

| Group C Exipients | |
|---|---|
| d-tocopherol (α, β, γ, δ isomers) | dimethyl sulfone (MSM) |
| dl-tocopherol (α, β, γ, δ isomers) | benzyl benzoate |
| the acetate and esters of C-3 to C-10 straight and branched chain aliphatic acids with the above tocopherol isomers | liquid to semisolid poly-carbonate oligomers, such as those prepared by the polymerization of trimethylene carbonate or the ester exchange polymerization of diethylene carbonate with aliphatic diols or polyoxyalkane diols [poly(di-1,2-propylene glycol carbonate) or poly(tri-1,2-propylene glycol carbonate)] |
| triethyl, tripropyl, or tribuyl esters of O-acetyl, O-propionyl, or O-butyryl citrate | tri-straight and branched chain C-1 to C-10 aliphatic alcohol esters of citric acid |
| omega-3 fatty acids and their ester with C-1 to C-10 straight and branched chain aliphatic alcohols | propylene glycol dibenzoate |
| dipropylene glycol dibenzoate | tripropylene glycol dibenzoate |

As mentioned above, to avoid harmful pro-oxidative chemistries care should be taken not to expose the cells to too high a level of the antioxidants. This may present a problem as formulators develop a one-shot formulation that administers steroids and antioxidants for months to a year or more. The formulation must incorporate enough antioxidants to last this long without releasing pro-oxidative concentrations. This is achieved in this embodiment of the invention by using lipophyllic prodrug forms of the antioxidants such as ascorbyl palmitate, tocopherol acetate, benzyl benzoate, and the like, which slowly release the active, more hydrophyllic form into the cellular environment upon hydrolysis.

Examples of an injectable sustained release formulation of this embodiment include formulations such as:

| | | | |
|---|---|---|---|
| (1) | benzyl benzoate | 60 pts/wt |
| | α-tocopherol acetate | 5 pts/wt |
| | ascorbyl palmitate | 5 pts/wt |
| | triamcinolone acetonate | 40 pts/wt |
| (2) | α-tocopherol acetate | 60 pts/wt |
| | ascorbyl palmitate | 10 pts/wt |
| | dexamethasone | 40 pts/wt |

Example 28

In Vitro Study of Dexamethasone in Triethyl O-Acetyl Citrate (TEAC)

Figure 25:
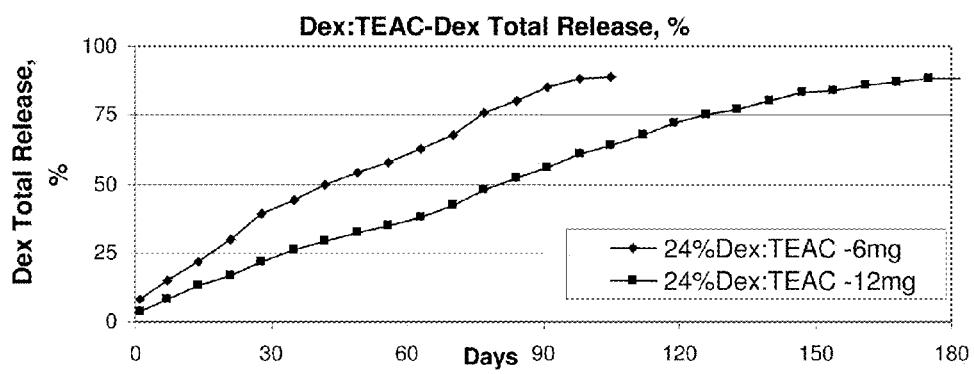
FIG. 25 depicts the percent Dex released in vitro from a formulation of 24% Dex and Triethyl O-Acetyl Citrate (TEAC).
Figure 26:
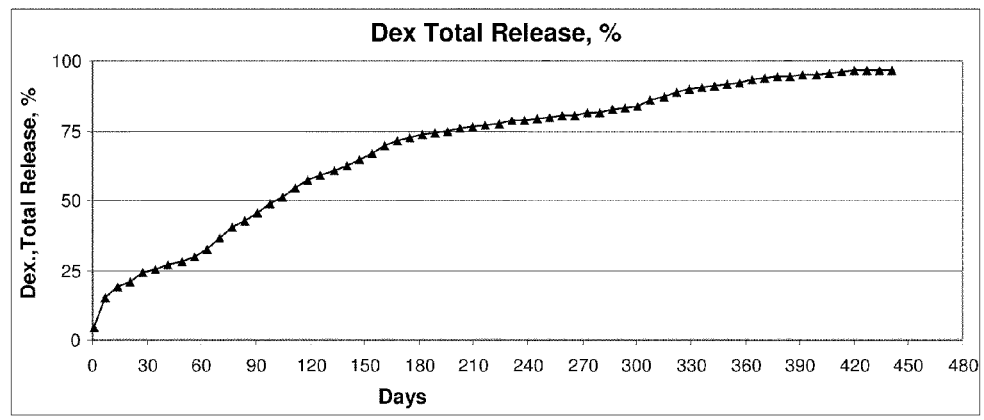
FIG. 26 shows the percent Dex released in vitro from a formulation of 20% Dex and TEAC/Tocopherol Acetate.

To 760 mg of TEAC was added 240 mg of Dexamethasone with ample stirring to form a homogeneous mixture. Six mg (25 µl) and 12 mg (25 µl) microdrops of this mixture were each incubated in 10 ml of 0.9% saline at 37° C. Periodically, 8 ml portions were withdrawn for assaying and replaced with 8 ml of fresh 0.9% saline. The release of Dex from a formulation consisting of 24% Dex in TEAC is depicted in FIG. 25. The release of Dex from a formulation consisting of a 6 mg (25 µl) microdrop of 20% Dex in 1:1 TEAC/Tocopherol Acetate is reflected in FIG. 26. In summary, these results indicate that adding Tocopherol Acetate to the TEAC excipient can extend the sustained release of therapeutic levels of Dex up to 450 days.

Example 29

In Vivo Study of Sustained Release of Active Agents from TEAC Formulations

Figure 27:
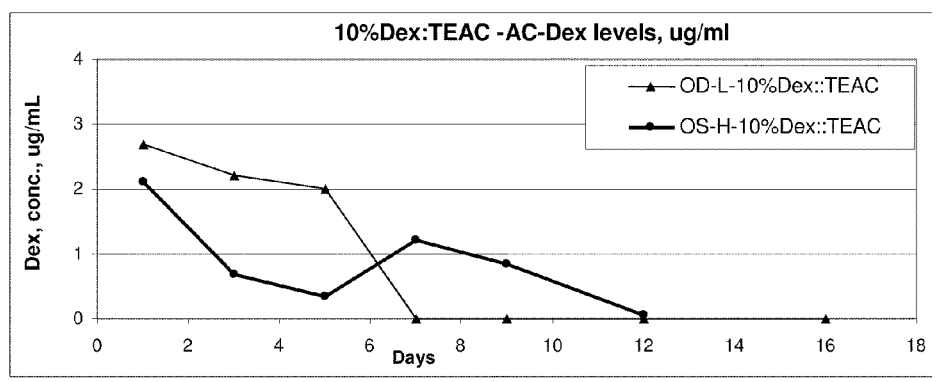
FIG. 27 illustrates the percent Dex released in vivo from a formulation of 10% Dex and TEAC injected into the rabbit eye anterior chamber (AC).

A microdrop of a mixture of 10% Dex in TEAC containing 200 µg of Dex was injected into the anterior chamber (AC) of the right eye of a rabbit with a 30 G needle. Similarly, a microdrop of the mixture containing 400 µg Dexamethasone was injected into the AC of the left eye of a rabbit. As illustrated in FIG. 27, the duration of therapeutic levels of Dexamethasone was seen to be twice as long in the left AC.

Figure 28:
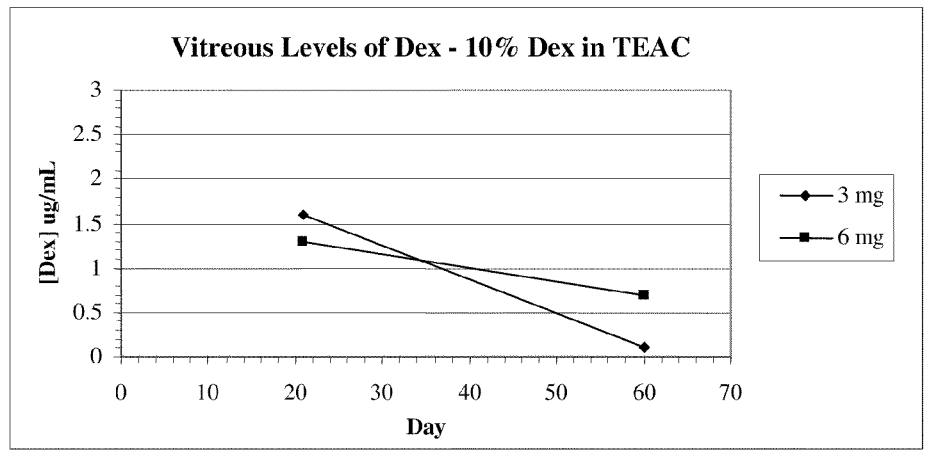
FIG. 28 presents the percent Dex released in vivo from a formulation of 10% Dex and TEAC injected into the rabbit eye vitreous chamber/posterior segment.

A 10% Dex in TEAC formulation was injected into a rabbit vitreous chamber/posterior segment (VC/PS). As shown in FIG. 28, sustained therapeutic intravitreal levels of Dex were maintained over sixty days following injection of 3 mg or 6 mg microdrops of a 10% Dex in TEAC mixture into the VC/PS.

Figure 29:
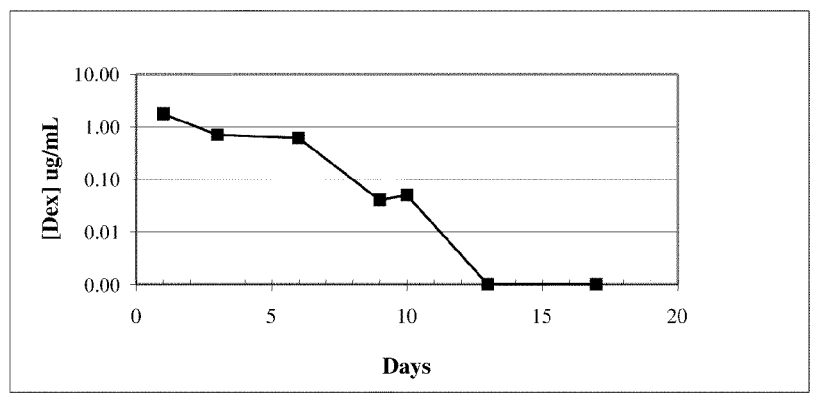
FIG. 29 depicts the kinetics of Dex released in vivo from 80 μg of Dex in a formulation of 20% Dex and TEAC injected into the rabbit eye AC.

A portion of the formulation amounting to 80 µg of Dex was injected with a 30 gauge needle into the anterior chamber of a NZW rabbit and the kinetics measured by HPLC. Therapeutic levels were observed over a twelve-day period, as depicted in FIG. 29.

Figure 30:
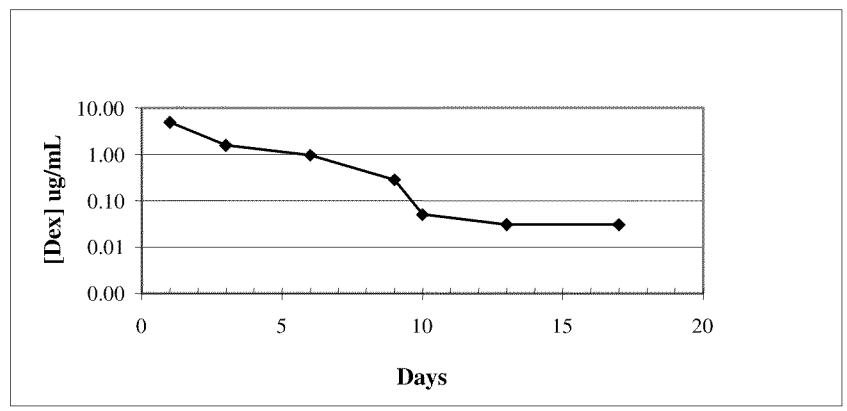
FIG. 30 depicts the kinetics of Dex released in vivo from 900 μg of Dex in a formulation of 20% Dex and TEAC injected into the rabbit eye AC.

A portion of the of the formulation amounting to 900 µg of Dex was administered into the anterior chamber of a NZW rabbit with a 30 gauge needle and kinetics were measured by HPLC. Therapeutic levels were observed over an eighteen-day period, as illustrated in FIG. 30.

Figure 31:
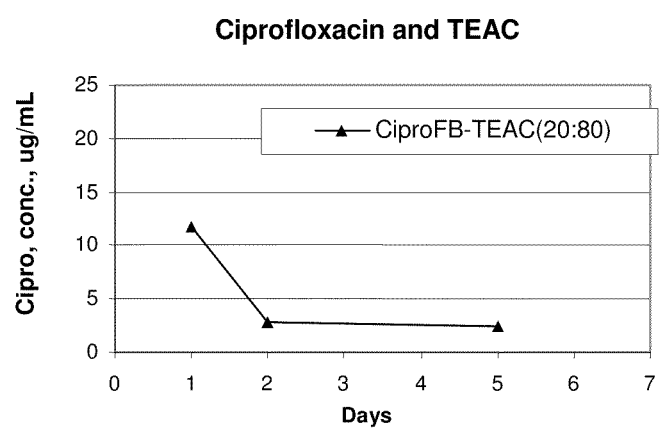
FIG. 31 shows the in vivo release of Ciprofloxacin from a 20% Ciprofloxacin/TEAC formulation injected into the AC of a rabbit eye.

A microdrop of a mixture of 20% Ciprofloxacin free base (FB) in TEAC, containing 300 µg of Ciprofloxacin FB, was injected into the AC of a rabbit eye. A therapeutic level of 2.44 µg/ml was maintained for up to five days, as shown in FIG. 31.

Example 30

In Vivo Release of Cyclosporin from Formulations Placed in the Eye

It has been reported (see, e.g., U.S. Pat. No. 5,294,604) that periocular administrations of cyclosporin A (CsA) are used to treat ocular diseases involving serious intraocular inflammatory processes requiring immunosuppression for sustained periods. Such diseases include endogenous uveitis, Behcet's Disease, corneal transplantation, vernal keratoconjunctivitis, ligneous keratoconjunctivitis, dry eye syndrome, anterior uveitis and onchocerciasis. The present embodiment provides for the intraocular injections of CsA formulations with novel excipients allowing for the sustained release of therapeutic, non-toxic levels of CsA, useful as therapies for such diseases. This Example reveals the reduction to practice of the use of these novel CsA formulations.

Figure 32:
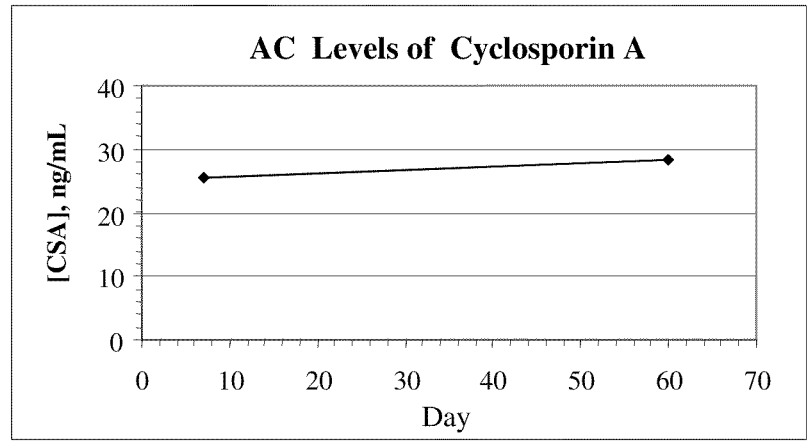
FIG. 32 presents the in vivo release of Cyclosporin A (CsA) from a CsA/tocopherol formulation injected into the AC of a rabbit eye.

Three (3.0) mg of a formulation containing a 40:60 mixture of cyclosporin A (CsA) in tocopherol acetate was injected into the anterior chamber of a 4.0-4.5 kg NZW rabbit. Aqueous humor samples were obtained and assayed for CsA via liquid chromatography and mass spectrometry. A release profile is depicted in FIG. 32.

Figure 33:
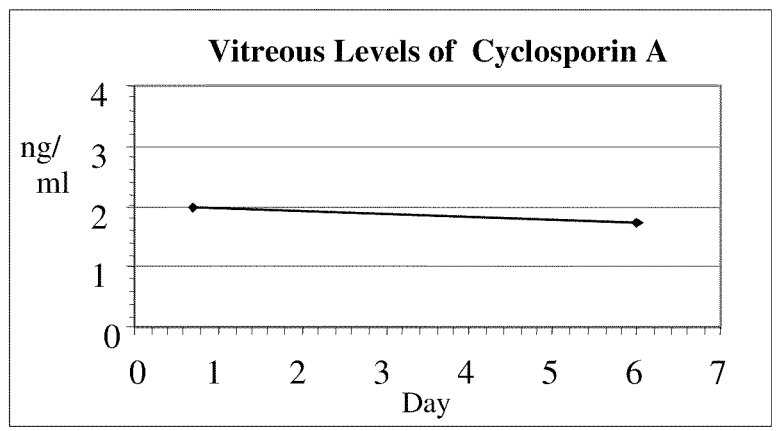
FIG. 33 presents the in vivo release of Cyclosporin A (CsA) from a CsA/TEAC formulation injected into the vitreous of a rabbit eye.
Figure 34:
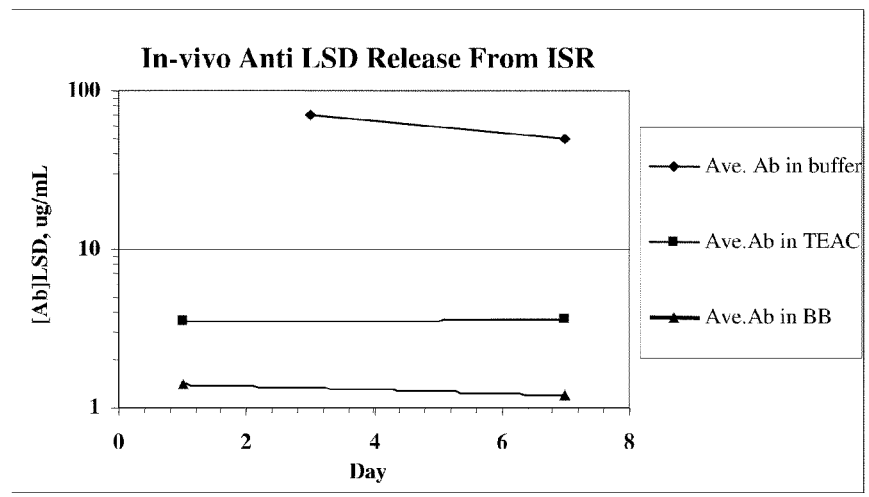
FIG. 34 illustrates the in vivo release of active monoclonal antibody (Mab) from three different formulations tested in the vitreous cavity of rabbit eyes.
Figure 35:
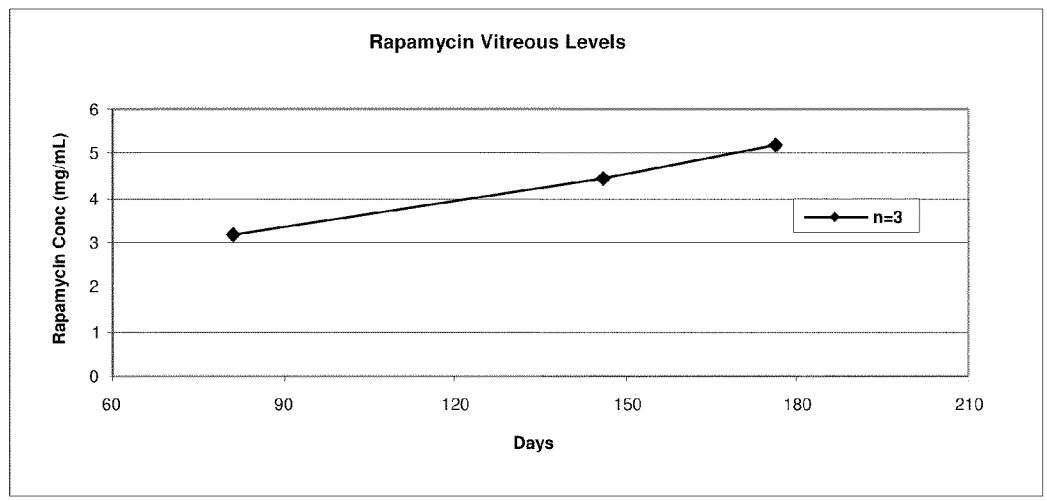
FIG. 35 reflects the intraocular sustained release of rapamycin from rapamycin:TEAC formulation injected into the vitreous cavity of rabbit eyes.

Approximately 14.0 mg of CsA (contained in a 25:75 mixture of CsA in triethyl acetyl citrate) was injected into the vitreous of a 4.0-4.5 kg NZW rabbit. Vitreous samples were obtained and assayed for CsA as described above. A release profile is depicted in FIG. 33.

Example 31

Sustained Release and Stability of Monoclonal Antibody-Containing Formulations

Three formulations containing 0.25 mg monoclonal antibody (Mab) against LSD were each injected into the vitreous cavity of 4 New Zealand White rabbits (ave. 4-4.5 kg). The first formulation the Mab was suspended in PBS buffer, the second and third containing lyophilized Mab in 25 μl of either Triethyl AcetylCitrate (TEAC) or Benzyl Benzoate (BB) respectively. Fifty (50) μl of vitreous were sampled from each animal as shown in Table 6 following intravitreal injections, and assayed for the Mab LSD activity in the standard microtiter ELISA method (Biostride, Redwood City, Calif.).

TABLE 6

| Day | Ave. Ab in PBS | Ave. Ab in TEAC | Ave. Ab in BB |
|---|---|---|---|
| 1 | | 3.5 | 1.4 |
| 3 | 71.5 | | |
| 7 | 49.5 | 3.6 | 1.2 |

The data, shown in FIG. 34, suggest that the half-life of the Mab in PBS is between three to five days: the Mab concentration on day three was 71.5 μg/ml and day seven was 49.5 μg/ml. In contrast, the Mab concentration released from the TEAC formulation on days one and seven were 3.5 μg/ml and 3.6 μg/ml, respectively. The Mab concentration released from the BB formulation on days one and seven were 1.4 μg/ml and 1.2 μg/ml, respectively. Comparable data interpretation on day seven suggests that controlled sustained release of Mab in the rabbit vitreous cavity can be achieved with TEAC and BB. The controlled level was 13.7× (49.5/3.6) more effective in TEAC than in PBS alone, and 41.25× (49.5/1.2) more effective in BB than in PBS alone. Controlled-sustained release of the Mab in TEAC and BB is apparent in this study, and the half-life of Mab in TEAC and BB could be well beyond seven days. The specificity of these assays suggests strongly that the integrity of the Mab was not affected in the formulary with TEAC and BB. In conclusion, the formulations of the present invention provide for the sustained release of sensitive polypeptides without denaturing their function.

Example 32

In Vivo Release of Rapamycin from TEAC Formulations

Five (5.0) mg rapamycin contained in a 10:90 rapamycin: TEAC mixture were injected into the vitreous cavity of one eye in three 4.0-4.5 kg. NZW rabbits. Vitreous sampling was performed in each animal, and the concentration of released Rapamycin determined by liquid chromatography and mass spectrometry. Results are depicted in FIG. 35, indicating that this formulation allowed the release of Rapamycin for over five months.

Example 33

Formulations for the In Vivo Release of Ketorolac Acid

Ketorolac acid and/or other nonsteroidal anti-inflammatory drugs (NSAIDs) are a different class of antiinflammatory drugs used widely in medicine and in the eye. They are less potent than corticosteroids and have fewer or less-severe side effects on the eye (such as glaucoma, cataracts which are common complications of corticosteroid use in the eye). Additionally, they may be used topically or in intraocular injection with or without sustained release parameters. There are early clinical findings indicating that non-sustained-release use of NSAID can be helpful in chronic macular edema. Hence, a sustained-release formulation may prove beneficial.

Figure 36:
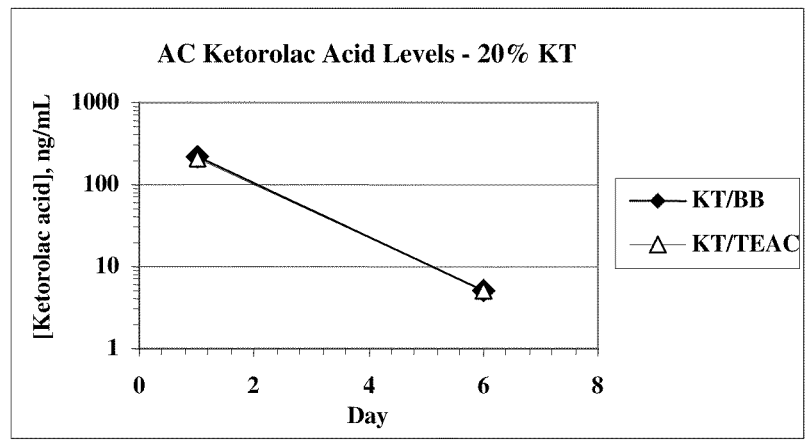
FIG. 36 shows the sustained release of ketorolac acid from a formulation of ketorolac acid:benzyl benzoate injected into the anterior chamber of the rabbit eye.

Eight-hundred (800) μg of ketorolac acid (♦) contained in a 20:80 ketorolac acid:BB mixture and 700 μg of ketorolac acid (Δ) contained in a 20:80 ketorolac acid:TEAC mixture were injected into the anterior chamber in one eye of each of two 4.0-4.5 kg NZW rabbits. Sampling of the aqueous humor for ketorolac determination by HPLC was performed, and the results are shown in FIG. 36.

Figure 37:
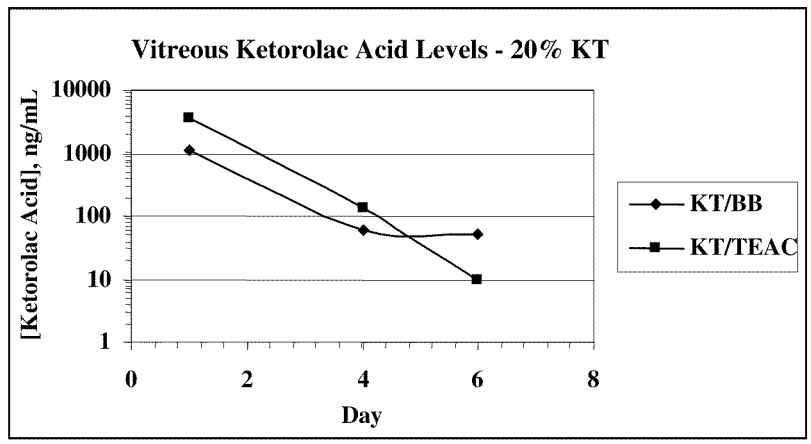
FIG. 37 shows the sustained release of ketorolac acid into the vitreous from either a formulation of ketorolac acid:benzyl benzoate or ketorolac acid:TEAC injected into the vitrous of the rabbit eye

Five (5.0) mg (25 μl) of ketorolac acid (♦) contained in a 20:80 ketorolac acid:BB mixture and 5 mg (25 μl) of ketorolac acid (■) contained in 20:80 ketorolac acid:TEAC mixture were injected into the vitreous cavity in one eye each of two 4.0-4.5 kg NZW rabbits. Sampling of the vitreous humor for ketorolac acid concentration was performed, and the results of the determination by HPLC are shown in FIG. 37.

Modifications of the above described modes for carrying out the invention that are obvious to those of ordinary skill in the surgical, pharmaceutical, or related arts are intended to be within the scope of the appended claims

What is claimed is:

1. A method of delivering the sustained release of an active agent to the eye of a subject comprising:
    administering, by injecting into the subconjunctiva, periocular space, retrobulbar in the orbit, episclera, intracornea, intrasclera, anterior chamber, anterior segment, posterior chamber, posterior segment, vitreous cavity, subretinal space, suprachorodial segment or intraretinal area of the eye, an injectable liquid pharmaceutical composition comprising:
    at least one excipient selected from the group consisting of tocopherol isomers and their esters, and tocotrienol isomers and their esters, wherein the amount of the excipient is sufficient to evenly dissolve or disperse the entire amount of the active agent in the composition;
    wherein upon initial injection the composition maintains its integrity as a single bolus; and
    wherein said excipient releases the active agent from the composition for a continuous and sustained period of at least about 60 days.

2. The method of claim 1, further comprising repeating said administering no sooner than after about 90 days.

3. The method of claim 1, wherein the subject is suffering a malady of the eye selected from the group consisting of allergic and infectious conjunctivitis, uveitis of the anterior and posterior segments, infectious endophthalmitis of the anterior segment and posterior segment, dry-eye syndrome, post-surgical inflammation and infection of the anterior and posterior segments, angle-closure glaucoma, open-angle glaucoma, post-surgical glaucoma, exophthalmos, scleritis, episcleritis, Grave's disease, pseudotumor of the orbit, lymphoma of the orbit, tumors of the orbit, orbital cellulitis, blepharitis, intraocular tumors, retinoblastoma, malignant melanoma, retinal fibrosis, vitreous substitute and vitreous replacement, iris neovascularization from cataract surgery, macular edema in central retinal vein occlusion, cellular transplantation, cystoid macular edema, pseudophakic cystoid macular edema, diabetic macular edema, diffuse diabetic macular edema, pre-phthisical ocular hypotomy, proliferative vitreoretinopathy, proliferative diabetic retinopathy, macular degeneration, extensive exudative retinal detachment, diabetic retinal edema, retinitis pigmentosa, ischemic ophthalmopathy, chronic focal immunologic and chemical corneal graft reaction, neovascular glaucoma, pars plana vitrectomy, sympathetic ophthalmia, intermediate uveitis, chronic uveitis, intraocular infection, endophthalmitis, Irvine-Gass syndrome, conditions of inflammatory and immunological nature, sequelae of surgical complications, acquired and hereditary ocular conditions, Tay-Sach's disease, Niemann-Pick's disease, cystinosis, corneal dystrophies, and multiple myeloma.

\* \* \* \* \*